United States Patent
Ginty et al.

(10) Patent No.: US 12,084,451 B2
(45) Date of Patent: *Sep. 10, 2024

(54) COMPOSITIONS AND METHODS FOR REDUCING TACTILE DYSFUNCTION, ANXIETY, AND SOCIAL IMPAIRMENT

(71) Applicant: President and Fellows of Harvard College, Cambridge, MA (US)

(72) Inventors: David D. Ginty, Cambridge, MA (US); Lauren L. Orefice, Cambridge, MA (US); Jinbo Lee, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 73 days.

This patent is subject to a terminal disclaimer.

(21) Appl. No.: 17/894,864

(22) Filed: Aug. 24, 2022

(65) Prior Publication Data
US 2023/0051850 A1    Feb. 16, 2023

Related U.S. Application Data

(63) Continuation of application No. 17/058,403, filed as application No. PCT/US2019/034390 on May 29, 2019, now Pat. No. 11,434,244.

(60) Provisional application No. 62/677,367, filed on May 29, 2018.

(51) Int. Cl.
A61K 31/437    (2006.01)
A61P 25/04     (2006.01)
C07D 471/04    (2006.01)
C07D 487/04    (2006.01)

(52) U.S. Cl.
CPC ............ *C07D 487/04* (2013.01); *A61P 25/04* (2018.01); *C07D 471/04* (2013.01)

(58) Field of Classification Search
CPC ..... C07D 471/04; A61K 31/437; A61P 25/00; A61P 25/04; A61P 25/22; A61P 29/00
USPC .......................................... 546/121; 514/300
See application file for complete search history.

(56) References Cited

U.S. PATENT DOCUMENTS

| | | |
|---|---|---|
| 3,243,427 A | 3/1966 | Recder et al. |
| 3,516,988 A | 6/1970 | Schmitt |
| 3,862,149 A | 1/1975 | Cortel et al. |
| 4,065,451 A | 12/1977 | McCaully et al. |
| 4,122,265 A | 10/1978 | Jaunin |
| 4,382,938 A | 5/1983 | Kaplan et al. |
| 4,460,592 A | 7/1984 | Kaplan et al. |
| 4,492,695 A | 1/1985 | Kaplan et al. |
| 4,820,834 A | 4/1989 | Evans et al. |
| 4,879,293 A | 11/1989 | Hiraga et al. |
| 5,618,824 A | 4/1997 | Schmidt et al. |
| 5,776,930 A | 7/1998 | Lynch, Jr. et al. |
| 5,786,357 A | 7/1998 | Young et al. |
| 6,927,290 B2 | 8/2005 | Miki et al. |
| 7,456,173 B2 | 11/2008 | Jerussi et al. |
| 8,980,887 B2 | 3/2015 | Yang et al. |
| 9,586,890 B2 | 3/2017 | Statsyuk et al. |
| 11,434,244 B2 | 9/2022 | Ginty et al. |
| 11,547,706 B2 | 1/2023 | Orefice et al. |
| 2006/0084806 A1 | 4/2006 | Sridharan et al. |
| 2007/0015810 A1 | 1/2007 | Cuberes |
| 2010/0150944 A1 | 6/2010 | Hilbush et al. |
| 2011/0046090 A1 | 2/2011 | Barlow et al. |
| 2012/0095217 A1 | 4/2012 | Ritter et al. |
| 2014/0066504 A1 | 3/2014 | Hochman |
| 2015/0051151 A1 | 2/2015 | Eisenbach-Schwartz et al. |
| 2015/0203486 A1 | 7/2015 | Bently et al. |
| 2015/0313913 A1 | 11/2015 | Catterall et al. |
| 2016/0193169 A1 | 7/2016 | Hoffman |
| 2017/0197967 A1 | 7/2017 | Pasricha et al. |
| 2020/0179374 A1 | 6/2020 | Orefice et al. |
| 2021/0128508 A1 | 5/2021 | Hoffman et al. |
| 2021/0206714 A1 | 7/2021 | Ginty et al. |
| 2021/0206771 A1 | 7/2021 | Ginty et al. |
| 2022/0162173 A1 | 5/2022 | Ginty et al. |
| 2022/0233133 A1 | 7/2022 | Ginty et al. |
| 2023/0031479 A1 | 2/2023 | Orefice et al. |

FOREIGN PATENT DOCUMENTS

| | | |
|---|---|---|
| CN | 103933036 A | 7/2014 |
| EP | 0167919 A2 | 1/1986 |
| WO | WO 1996/031210 A1 | 4/1996 |
| WO | WO 97/49690 A1 | 12/1997 |
| WO | WO 1999/051594 A1 | 10/1999 |
| WO | WO 2002/028831 A1 | 4/2002 |
| WO | WO 03/051274 A2 | 6/2003 |
| WO | WO 2004/106310 A1 | 12/2004 |
| WO | WO 2008/003044 A2 | 1/2008 |
| WO | WO 2008/022396 A1 | 2/2008 |

(Continued)

OTHER PUBLICATIONS

Partial Supplementary European Search Report, mailed Jan. 24, 2020, in connection with Application No. EP 17811036.7.
European Search Report, mailed Jun. 24, 2020, in connection with Application No. EP 17811036.7.
Invitation to Pay Additional Fees, mailed Sep. 11, 2017, in connection with Application No. PCT/US2017/036621.
International Search Report and Written Opinion, mailed Nov. 9, 2017, in connection with Application No. Application No. PCT/US2017/036621.
International Preliminary Report on Patentability, mailed Oct. 29, 2018, in connection with Application No. PCT/US2017/036621.
Extended European Search Report for Application No. 19806972.6, mailed Feb. 9, 2022.

(Continued)

*Primary Examiner* — Charanjit Aulakh
(74) *Attorney, Agent, or Firm* — Wolf, Greenfield & Sacks, P.C.

(57) ABSTRACT

The present invention features novel peripherally-restricted non-benzodiazipene analogs with reduced blood brain barrier permeability and methods of use thereof for reducing tactile dysfunction, social impairment, and anxiety in a subject diagnosed with Autism Spectrum Disorder, Rett syndrome, Phelan McDermid syndrome, or Fragile X syndrome, or for treating touch over-reactivity, pain, or mechanical allodynia.

20 Claims, 11 Drawing Sheets

(56) References Cited

FOREIGN PATENT DOCUMENTS

| WO | WO 2010/017047 A1 | 2/2010 |
| --- | --- | --- |
| WO | WO 2013/154712 A1 | 10/2013 |
| WO | WO 2014/100438 A1 | 6/2014 |
| WO | WO 2014/123909 A1 | 8/2014 |
| WO | WO 2014/138791 A1 | 9/2014 |
| WO | WO 2015/013715 A2 | 1/2015 |
| WO | WO 2015/052076 A1 | 4/2015 |
| WO | WO 2017/214442 A1 | 12/2017 |
| WO | WO 2018/114663 A1 | 6/2018 |
| WO | WO 2019/103658 A2 | 5/2019 |
| WO | WO 2020/237043 A1 | 11/2020 |

OTHER PUBLICATIONS

International Search Report and Written Opinion, mailed Jul. 25, 2019, in connection with Application No. PCT/US2019/033581.
International Preliminary Report on Patentability, mailedDec. 3, 2020, in connection with Application No. PCT/US2019/033581.
Partial European Search Report, mailed Sep. 16, 2021, in connection with Application No. 19810786.4.
Extended European Search Report, mailed Dec. 20, 2021, in connection with Application No. 19810786.4.
Invitation to Pay Additional Fees, mailed Jul. 19, 2019, in connection with Application No. PCT/US2019/034390.
International Search Report and Written Opinion, mailed Sep. 19, 2019, in connection with Application No. PCT/US2019/034390.
International Preliminary Report on Patentability, mailed Dec. 10, 2020, in connection with Application No. PCT/US2019/034390.
Extended European Search Report for Application No. 20779891.9, mailed Nov. 21, 2022.
Invitation to Pay Additional Fees, mailed Jun. 4, 2020, in connection with Application No. PCT/US2020/024564.
International Search Report aand Written Opinion, mailed Jul. 28, 2020, in connection with Application No. PCT/US2020/024564.
International Preliminary Report on Patentability, mailed Oct. 7, 2021, in connection with Application No. PCT/US2020/024564.
International Search Report aand Written Opinion, mailed Aug. 17, 2020, in connection with Application No. PCT/US2020/033984.
International Preliminary Report on Patentability, mailed Dec. 2, 2021, in connection with Application No. PCT/US2020/033984.
[No Author Listed] Caplus Registry No. 1616667-55-0. Carbamic acid, N,N-diethyl-, 6-(5-chloro-2-pyridinyl)-6,7-dihydro-7-oxo-5H-pyrrolo[3,4-b]pyrazin-5-yl ester entered STN: Jul. 23, 2014.
[No Author Listed] Caplus Registry No. 952499-50-2. [1,2-a]pyridine-3-acetamide, 6,8-dichloro-2-(4-chlorophenyl)-N-[2-[(7-nitro-2,1,3-benzoxadiazol-4-yl)amino]ethyl]-N-(phenylmethyl)- Entered STN: Nov. 6, 2007.
[No Author Listed] Caplus Registry No. 952499-71-7. Carbamic acid, N-[2-[[2-[6,8-dichloro-2-(4-chlorophenyl)imidazo[1,2-a]pyridin-3-yl]acetyl](phenylmethyl)amino]ethyl]-, 1,1-dimethylethyl ester. Entered STN: Nov. 6, 2007.
[No Author Listed] Caplus Registry No. 952499-78-4. 1,2-a]pyridine-3-acetamide, N-(2-aminoethyl)-6,8-dichloro-2-(4-chlorophenyl)-N-(phenylmethyl). Entered STN: Nov. 6, 2007.
[No Author Listed] PubChem. 4-Methyl-1-{[2-(4-chlorophenyl)-imidazo[1,2-a]pyridin-3-yl]-methylcarbonyl}-piperazine. Accessed Jul. 11, 2019; created Feb. 8, 2017; modified Jul. 10, 2019. https://pubchem.ncbi.nlm.nih.gov/compound/13068199. 7 pages.
[No Author Listed] PubChem. Compound Summary for SID 319566201. Available Date Dec. 8, 2016; [Retrieved on Jul. 2, 2019]. Retrieved from the internet. https://pubchem.ncbi.nlm.nih.gov/substance/319566201.
[No Author Listed] Pubmed-CID: 13068199. Create Date: Feb. 8, 2007. pp. 1-7.
[No Author Listed] Pubmed-CID: 19842214. Create Date: Dec. 5, 2007. pp. 1- 7.
[No Author Listed] Pubmed-CID: 4506. Create Date: Mar. 25, 2005. pp. 1-47.
[No Author Listed] Pubmed-CID: 614001. Create Date: Mar. 27, 2005. pp. 1-11.
[No Author Listed], Annex to ESOP (EP19810786). Jan. 1, 2021. 84 pages.
[No Author Listed], CAS RN: 2098817-47-9. 2017. 3 pages.
Abrahams et al., Advances in autism genetics: on the threshold of a new neurobiology. Nat Rev Genet. May 2008;9(5):341-55. doi: 10.1038/nrg2346.
Agudo et al., Achieving regio- and enantioselectivity of P450-catalyzed oxidative CH activation of small functionalized molecules by structure-guided directed evolution. Chembiochem. Jul. 9, 2012;13(10):1465-73. doi: 10.1002/cbic.201200244. Epub Jun. 18, 2012.
Akyol et al., Generating somatic mosaicism with a Cre recombinase-microsatellite sequence transgene. Nat Methods. Mar. 2008;5(3):231-3.
Amaral et al., The amygdala and autism: implications from non-human primate studies. Genes Brain Behav. Oct. 2003;2(5):295-302.
Amaral, The amygdala, social behavior, and danger detection. Ann N Y Acad Sci. Dec. 2003;1000(1):337-47.
Anagnostou et al., Intranasal oxytocin versus placebo in the treatment of adults with autism spectrum disorders: a randomized controlled trial. Mol Autism. Dec. 2012;3(1):16.
Antoine et al., Increased Excitation-Inhibition Ratio Stabilizes Synapse and Circuit Excitability in Four Autism Mouse Models. Neuron. Feb. 20, 2019;101(4):648-61.
Bader et al., Neurophysiological findings in the Rett syndrome, I: EMG, conduction velocity, EEG and somatosensory-evoked potential studies. Brain Dev. Jan. 1, 1989;11(2):102-9.
Baio et al., Prevalence of Autism Spectrum Disorder Among Children Aged 8 Years—Autism and Developmental Disabilities Monitoring Network, 11 Sites, United States, 2014. MMWR Surveill Summ. Apr. 27, 2018; 67(6): 1-23.
Banerjee et al., Impairment of cortical GABAergic synaptic transmission in an environmental rat model of autism. Int J Neuropsychopharmacol. Jul. 2013;16(6):1309-18. doi: 10.1017/S1461145712001216. Epub Dec. 11, 2012.
Berge et al., Pharmaceutical salts. J Pharm Sci. Jan. 1977;66(1):1-19.
Bhattacherjee et al., Neuronal cytoskeletal gene dysregulation and mechanical hypersensitivity in a rat model of Rett syndrome. Proceedings of the National Academy of Sciences. Aug. 15, 2017; 114(33): E6952-E6961.
Boitano et al., Structure activity studies of a novel cytotoxic benzodiazepine. Bioorg Med Chem Lett. Oct. 6, 2003;13(19):3327-30. doi: 10.1016/s0960-894x(03)00683-8.
Bowery et al., Isoguvacine, isonipecotic acid, muscimol and N-methyl isoguvacine on the GABA receptor in rat sympathetic ganglia. Experientia. Sep. 15, 1978;34(9):1193-5. doi: 10.1007/BF01922953.
Bowery et al., Characteristics of GABAB receptor binding sites on rat whole brain synaptic membranes. Br J Pharmacol. Jan. 1983; 78(1): 191-206.
Boyle et al., The behavioral phenotype of FMR1 mutations. Am J Med Genet C Semin Med Genet. Nov. 15, 2010; 154(4): 469-76.
Braat et al., The GABAA Receptor as a Therapeutic Target for Neurodevelopmental Disorders. Neuron. Jun. 3, 2015;86(5):1119-30.
Braff et al., Human studies of prepulse inhibition of startle: normal subjects, patient groups, and pharmacological studies. Psychopharmacology (Berl.). Jul. 2001;156(2-3):234-58. doi: 10.1007/s002130100810.
Brandt et al., Impaired peripheral somatosensory function in children with Prader- Willi syndrome. Neuropediatrics. Jun. 1998; 29(30): 124-6.
Carlton et al., Peripheral GABA(A) receptors: evidence for peripheral primary afferent depolarization. Neuroscience. Jul. 1, 1999; 93(2): 713-22.
Cascio et al., Tactile Perception in Adults with Autism: a Multidimensional Psychophysical Study. J Autism Dev Disord. Jan. 2008;38(1):127-37. doi: 10.1007/s10803-007-0370-8. Epub Apr. 6, 2007.

(56) References Cited

OTHER PUBLICATIONS

Cascio, Somatosensory processing in neurodevelopmental disorders. J Neurodev Disord. Jun. 2010;2(2):62-9.
Cellot et al., GABAergic signaling as therapeutic target for autism spectrum disorders. Front Pediatr. Jul. 8, 2014;2:70.
Chen et al., Presynaptic GABAergic inhibition regulated by BDNF contributes to neuropathic pain induction. Nature communications. Oct. 30, 2014; 5: 5331.
Cheng et al., Relationship between the inhibition constant (KI) and the concentration of inhibitor which causes 50 per cent inhibition (150) of an enzymatic reaction. Biochem. Pharmacol. Dec. 1973;22(23):3099-3108.
Choi et al., The maternal interleukin-17a pathway in mice promotes autism-like phenotypes in offspring. Science. Feb. 26, 2016; 351(6276): 933-9.
Coury et al., Use of psychotropic medication in children and adolescents with autism spectrum disorders. Pediatrics. Nov. 1, 2012; 130(Suppl 2): S69-76.
Crozier et al., MrgD activation inhibits KCNQ/M-currents and contributes to enhanced neuronal excitability. The Journal of neuroscience : the official journal of the Society for Neuroscience. Apr. 18, 2007; 27(16): 4492-6.
Dalai et al., Exploring selectivity requirements for peripheral versus central benzodiazepine receptor binding affinity: QSAR modeling of 2-phenylimidazo[1,2-a]pyridine acetamides using topological and physicochemical descriptors. Indian J Biochem Biophys. Apr. 2006;43(2):105-18.
Dawes et al., Immune or Genetic-Mediated Disruption of CASPR2 Causes Pain Hypersensitivity Due to Enhanced Primary Afferent Excitability. Neuron. Feb. 21, 2018; 97(4): 806-22.
Denora et al., 2-Phenyl-imidazo[1,2-a]pyridine compounds containing hydrophilic groups as potent and selective ligands for peripheral benzodiazepine receptors: synthesis, binding affinity and electrophysiological studies. J Med Chem. Nov. 13, 2008;51(21):6876-88. doi: 10.1021/jm8006728. Epub Oct. 4, 2008.
Dorrn et al., Developmental sensory experience balances cortical excitation and inhibition. Nature. Jun. 2010; 465(7300): 932-6.
Downs et al., Linking MECP2 and pain sensitivity: the example of Rett syndrome. Am J Med Genet A. May 2010; 152(5): 1197- 205.
Drasbek et al., THIP, a hypnotic and antinociceptive drug, enhances an extrasynaptic GABAA receptor-mediated conductance in mouse neocortex. Cereb Cortex. Aug. 2006;16(8):1134-41. doi: 10.1093/cercor/bhj055. Epub Oct. 12, 2005.
Du et al., Local GABAergic signaling within sensory ganglia controls peripheral nociceptive transmission. J Clin Invest. May 1, 2017; 127(5): 1741-56.
Enna et al., The role of GABA in the mediation and perception of pain. Adv Pharmacol. Jan. 1, 2006; 54: 1-27.
Erickson et al., STX209 (arbaclofen) for autism spectrum disorders: an 8-week open-label study. J Autism Dev Disord. Apr. 1, 2014; 44(4): 958-64.
Fier et al., Synthesis and late-stage functionalization of complex molecules through C—H fluorination and nucleophilic aromatic substitution. J Am Chem Soc. Jul. 16, 2014;136(28):10139-47. doi: 10.1021/ja5049303. Epub Jul. 1, 2014.
Filice et al. Reduction in parvalbumin expression not loss of the parvalbumin-expressing GABA interneuron subpopulation in genetic parvalbumin and shank mouse models of autism. Mol Brain. Dec. 2016; 9: 10.
Flegel et al., RNA- Seq Analysis of Human Trigeminal and Dorsal Root Ganglia with a Focus on Chemoreceptors. PLoS One. Jun. 12, 2015; 10(6): e0128951.
Fukuda et al., Delayed maturation of neuronal architecture and synaptogenesis in cerebral cortex of Mecp2-deficient mice. J Neuropathol Exp Neurol. Jun. 1, 2005; 64(6): 537-44.
Gebhardt et al., Maturation of prepulse inhibition (PPI) in childhood: Maturation of PPI in childhood. Psychophysiology. Apr. 2012;49(4):484-8. doi: 10.1111/j.1469-8986.2011.01323.x. Epub Dec. 16, 2011.
Golombok et al., Cognitive impairment in long-term benzodiazepine users. Psychol Med. May 1988; 18(2): 365-74.
Groeneveld et al., Measuring blood-brain barrier penetration using the NeuroCart, a CNS test battery. Drug Discov Today Technol. Jun. 1, 2016; 20: 27-34.
Guastella et al. The effects of a course of intranasal oxytocin on social behaviors in youth diagnosed with autism spectrum disorders: a randomized controlled trial. J Child Psychol Psychiatry. Apr. 2015; 56(4): 444-52.
Gudex, Adverse effects of benzodiazepines. Soc Sci Med. Jan. 1, 1991; 33(5): 587-96.
Guetzoyan et al., Flow chemistry synthesis of zolpidem, alpidem and other GABA agonists and their iological evaluation through the use of in-line frontal affinity chromatography. Chemical Science. 2013; 4(2): 764-69.
Gupta et al., Quantitative structure-activity relationship studies on some nonbenzodiazepine series of compounds acting at the benzodiazepine receptor. Bioorg Med Chem. Nov. 1998;6(11):2213-8. doi: 10.1016/s0968-0896(98)00169-2.
Guy et al., A mouse Mecp2-null mutation causes neurological symptoms that mimic Rett syndrome. Nat Genet. Mar. 2001;27(3):322-6.
Haas et al., Peripheral nerve findings in Rett syndrome. J Child Neurol. Jan. 1988; 3(1_Suppl): S25-30.
Hadjikhani et al., Bumetanide for autism: more eye contact, less amygdala activation. Sci Rep. Feb. 26, 2018; 8(1): 3602.
Hagerman et al., Neuropathy as a presenting feature in fragile X-associated tremor/ataxia syndrome. Am J Med Genet A. Oct. 1, 2007; 143(19): 2256-60.
Han et al. SHANK3 Deficiency Impairs Heat Hyperalgesia and TRPV1 Signaling in Primary Sensory Neurons. Neuron. Dec. 2, 20161; 92(6): 1279-93.
Hanack et al., GABA blocks pathological but not acute TRPV1 pain signals. Cell. Feb. 12, 2015; 160(4): 759-770.
Hanson et al., Structural requirements for eszopiclone and zolpidem binding to the gamma-aminobutyric acid type-A (GABAA) receptor are different. J Med Chem. Nov. 27, 2008;51(22):7243-52. doi: 10.1021/jm800889m.
Hasegawa et al., Analyzing somatosensory axon projections with the sensory neuron-specific Advillin gene. The Journal of neuroscience : the official journal of the Society for Neuroscience. Dec. 26, 2007; 27(52): 14404-14.
Hashemi et al., The Number of Parvalbumin-Expressing Interneurons Is Decreased in the Medial Prefrontal Cortex in Autism. Cereb Cortex. Mar. 1, 2017; 27(3): 1931-43.
He et al., Critical period inhibition of NKCC1 rectifies synapse plasticity in the somatosensory cortex and restores adult tactile response maps in fragile X mice. Mol Psychiatry. Nov. 2019; 24(11):1732-47.
Hill et al.,3H-baclofen and 3H-GABA bind to bicuculline-insensitive GABA B sites in rat brain. Nature. Mar. 1981; 290(5802): 149-152.
Hoehn-Saric et al., Effects of THIP on chronic anxiety. Psychopharmacology (Berl). 1983;80(4):338-41. doi: 10.1007/BF00432116.
Howes et al., Autism spectrum disorder: Consensus guidelines on assessment, treatment and research from the British Association for Psychopharmacology. J Psychopharmacol. Jan. 2018; 32(1): 3- 29.
Hubel et al., The period of susceptibility to the physiological effects of unilateral eye closure in kittens. The Journal of physiology. Feb. 1, 1970; 206(2): 419-36.
Janak et al., From circuits to behaviour in the amygdala. Nature. Jan. 2015; 517(7534): 284-92.
Jaramillo et al., Novel Shank3 mutant exhibits behaviors with face validity for autism and altered striatal and hippocampal function. Autism Res. Jan. 2017; 10(1): 42-65.
Jellinger et al., Neuropathology of Rett syndrome. Acta Neuropathol. Mar. 1, 1988; 76(2):142-58.
Jevtovic-Todorovic et al., Early exposure to common anesthetic agents causes widespread neurodegeneration in the developing rat brain and persistent learning deficits. The Journal of neuroscience: the official journal of the Society for Neuroscience. Feb. 1, 2003; 23(3): 876-82.

(56) References Cited

OTHER PUBLICATIONS

Jiao et al. A key mechanism underlying sensory experience-dependent maturation of neocortical GABAergic circuits in vivo. Proceedings of the National Academy of Sciences. Jul. 19, 2011; 108(29): 12131-6.

Kanner, Autistic disturbances of affective contact. Nerv Child. 1943; 2: 217-250.

Khalfa et al., Peripheral auditory asymmetry in infantile autism. Eur J Neurosci. Feb. 2001; 13(3): 628-32.

King et al., Lack of efficacy of citalopram in children with autism spectrum disorders and high levels of repetitive behavior: citalopram ineffective in children with autism. Arch Gen Psychiatry. Jun. 1, 2009; 66(6): 583-90.

Kodish et al., Pharmacotherapy for anxiety disorders in children and adolescents. Dialogues in clinical neuroscience. Dec. 2011; 13(4): 439-452.

Kohl et al., Prepulse Inhibition of the Acoustic Startle Reflex in High Functioning Autism. Plos One. Mar. 18, 2014;9(3):e92372. doi: 10.1371/journal.pone.0092372. eCollection 2014.

Konig et al., Integrator or coincidence detector? The role of the cortical neuron revisited. Trends Neurosci. Apr. 1, 1996; 19(4): 130-7.

Krishnan et al., MeCP2 regulates the timing of critical period plasticity that shapes functional connectivity in primary visual cortex. Proceedings of the National Academy of Sciences. Aug. 25, 2015; 112(34): E4782-91.

Krogsgaard-Larsen et al., A new class of GABA agonist. Nature. 1977; 268: 53-55.

Krogsgaard-Larsen et al., Structure-activity studies on the inhibition of GABA binding to rat brain membranes by muscimol and related compounds. J Neurochem. Jun. 1978; 30(6): 1377-82.

Krogsgaard-Larsen et al., THIP, isoguvacine, isoguvacine oxide, and related GABA agonists. Adv Biochem Psychopharmacol. 1981; 29: 69-76.

Kuznetsov et al., Synthesis of cyclic I1-5,7 amino alcohols with cholinolytic properties. Zhurnal Obshchei Khimii [Russian Journal of Organic Chemistry]. Jan. 1, 1959; 29: 2421-2428.

Laquintana et al., N-Benzyl-2-(6,8-dichloro-2-(4-chlorophenyl)imidazo[1,2-a]pyridin-3-yl)-N-(6-(7-nitrobenzo[c][1,2,5]oxadiazol-4-ylamino)hexyl)acetamide as a New Fluorescent Probe for Peripheral Benzodiazepine Receptor and Microglial Cell Visualization†. Bioconjugate Chem. 2007;18(5):1397-1407.

Lau et al., Temporal control of gene deletion in sensory ganglia using a tamoxifen-inducible Advillin-Cre-ERT2 recombinase mouse. Mol Pain. Dec. 21, 2011; 7: 1744-8069.

Lemonnier et al., Effects of bumetanide on neurobehavioral function in children and adolescents with autism spectrum disorders. Transl Psychiatry. Mar. 2017; 7(3): e1056.

Levy et al., The effect of the GABA antagonists bicuculline and picrotoxin on primary afferent terminal excitability. Brain research. Aug. 11, 1972; 43(1): 171-80.

Lopez-Mendoza et al., Visible light/Ir(III) photocatalytic initiation of xanthate-based radical-chain reactions: Xanthate group transfer and oxidative addition to aromatic systems. Tetrahedron. Apr. 2018; 74(38):5494-5502.

Lozano et al., Modulation of the GABAergic pathway for the treatment of fragile X syndrome. Neuropsychiatr Dis Treat. Sep. 16, 2014;10:1769-79. doi: 10.2147/NDT.S42919. eCollection 2014.

Lyst et al., Rett syndrome mutations abolish the interaction of MeCP2 with the NCoR/SMRT co-repressor. Nature neuroscience. Jul. 2013; 16(7): 898-902.

Maddox et al., The Accuracy of the ADOS-2 in Identifying Autism among Adults with Complex Psychiatric Conditions. J Autism Dev Disord. Sep. 2017;47(9):2703-2709. doi: 10.1007/s10803-017-3188-z.

Madsen et al., Increased Prepulse Inhibition and Sensitization of the Startle Reflex in Autistic Children: Sensorimotor gating in autistic children. Autism Res. Feb. 2014;7(1):94-103. doi: 10.1002/aur. 1337. Epub Oct. 4, 2013.

Mammen et al., Infant Avoidance during a Tactile Task Predicts Autism Spectrum Behaviors in Toddlerhood. Infant Ment Health J. Nov. 2015; 36(6): 575-87.

Marin, Interneuron dysfunction in psychiatric disorders. Nat Rev Neurosci. Feb. 2012; 13(2): 107-120.

Mazurek et al., Anxiety, sensory over-responsivity, and gastrointestinal problems in children with autism spectrum disorders. J Abnorm Child Psychol. Jan. 1, 2013; 41(1): 165-76.

Mei et al., Adult restoration of Shank3 expression rescues selective autistic-like phenotypes. Nature. Feb. 2016; 530(7591): 481-4.

Nadeau et al., Treatment of comorbid anxiety and autism spectrum disorders. Neuropsychiatry. Dec. 2011;1(6):567-78.

Nelson et al., Excitatory/Inhibitory Balance and Circuit Homeostasis in Autism Spectrum Disorders. Neuron. Aug. 19, 2015;87(4): 684-98.

Obradovic et al., Silencing the alpha2 subunit of gamma-aminobutyric acid type A receptors in rat dorsal root ganglia reveals its major role in antinociception posttraumatic nerve injury. Anesthesiology. Sep. 1, 2015; 123(3): 654-67.

Oginsky et al., Hyperexcitability of Mesencephalic Trigeminal Neurons and Reorganization of Ion Channel Expression in a Rett Syndrome Model. J Cell Physiol. May 2017; 232(5): 1151-64.

Olmos-Serrano et al., The GABA(A) receptor agonist THIP ameliorates specific behavioral deficits in the mouse model of fragile X syndrome. Dev Neurosci. 2011;33(5):395-403. doi: 10.1159/000332884. Epub Nov. 8, 2011.

Orefice et al., Peripheral Mechanosensory Neuron Dysfunction Underlies Tactile and Behavioral Deficits in Mouse Models of ASDs. Cell. Jul. 14, 2016; 166(2): 299-313.

Orefice et al., Targeting Peripheral Somatosensory Neurons to Improve Tactile-Related Phenotypes in ASD Models. Cell. Aug. 8, 2019;178(4):867-886.e24. doi: 10.1016/j.cell.2019.07.024.

Orefice, Peripheral Somatosensory Neuron Dysfunction: Emerging Roles in Autism Spectrum Disorders. Neuroscience. Oct. 1, 2020;445:120-129. doi: 10.1016/j.neuroscience.2020.01.039. Epub Feb. 6, 2020.

Page et al.,GABA(B) receptors inhibit mechanosensitivity of primary afferent endings. The Journal of neuroscience : the official journal of the Society for Neuroscience. Oct. 1, 1999; 19(19): 8597-8602.

Pajouhesh et al., Medicinal chemical properties of successful central nervous system drugs. NeuroRx. Oct. 1, 2005; 2(4): 541-553.

Pardridge, Drug transport across the blood-brain barrier. J Cereb Blood Flow Metab. Nov. 2012;32(11):1959-72. doi: 10.1038/jcbfm.2012.126. Epub Aug. 29, 2012.

Paulson et al., Blood-brain barrier transfer and cerebral uptake of antiepileptic drugs. Clin Pharmacol Ther. Oct. 1982;32(4):466-77. doi: 10.1038/clpt.1982.190.

Peca et al., Shank3 mutant mice display autistic-like behaviours and striatal dysfunction. Nature. Apr. 2011;472(7344): 437-442.

Peixoto et al., Early hyperactivity and precocious maturation of corticostriatal circuits in Shank3B(-/-) mice. Nature neuroscience. May 2016; 19(5): 716-24.

Perche et al., Early Retinal Defects in Fmr1(-/y) Mice: Toward a Critical Role of Visual Dys-Sensitivity in the Fragile X Syndrome Phenotype? Front Cell Neurosci. Apr. 6, 2018; 12: 96.

Phelan et al., The 22q13.3 Deletion Syndrome (Phelan-McDermid Syndrome). Mol Syndromol. 2011; 2(3-5): 186-201.

Price et al., Fragile X mental retardation protein (FMRP) and the spinal sensory system. Results Probl Cell Differ. 2012; 54, 41-59.

Ray et al., Comparative transcriptome profiling of the human and mouse dorsal root ganglia: an RNA-seq-based resource for pain and sensory neuroscience research. Pain. Jul. 2018; 159(7): 1325-1345.

Roland et al., Quinazolines et benzodiazepines-1,4. LX1) Imidazo[5,1-c]benzodiazepines-1,4. 1973; 56(7):2569-2583. Helvetica Chimica Acta. Retrieved from the Internet: URL: https://api.wiley.com/onlinelibrary/tdm/v1/articles/10.1002%2Fhlca.19730560742>.

Romermann et al., Multiple blood-brain barrier transport mechanisms limit bumetanide accumulation, and therapeutic potential, in the mammalian brain. Neuropharmacology. May 1, 2017; 117: 182-94.

(56) References Cited

OTHER PUBLICATIONS

Roy et al., QSAR modeling of peripheral versus central benzodiazepine receptor binding affinity of 2-phenylimidazo[1,2-a]pyridineacetamides using optimal descriptors calculated with Smiles. Qsar Comb Sci. 2007; 26(4): 460-468.
Rudolph et al., Beyond classical benzodiazepines: novel therapeutic potential of GABAA receptor subtypes. Nat Rev Drug Discov. Sep. 2011; 10(9): 685-97.
Salamon, Conners Scale for ADHD Assessment. WebMD. Jul. 12, 2020. available at https://www.webmd.com/add-adhd/childhood-adhd/conners-rating-scale#:text=The%20Conners%20rating%20scale%20is,%2C%20home%20life%2C%20and%20relationships. 2 pages.
Samanta et al., Search for Structural Requirements of 2-Phenylimidazo[1,2-a]pyridineacetamide Analogs to Improve Affinity and Selectivity towards Central and/or Peripheral Benzodiazepine Receptors. Internet Electronic Journal of Molecular Design. Jul. 2007; 6(7): 183-99.
Schultz et al., Sensory hypersensitivity predicts repetitive behaviours in autistic and typically-developing children. Autism : the international journal of research and practice. May 2019; 23(4): 1028-41.
Shank et al., Ion and temperature effects on the binding of gamma-aminobutyrate to its receptors and the high-affinity transport system. J. Neurochem. Jun. 1990;54(6):2007-15.
Silverman et al., Behavioural phenotyping assays for mouse models of autism. Nat Rev Neurosci. Jul. 2010; 11(7):490-502. doi: 10.1038/nrn2851.
Simons et al., Early experience of tactile stimulation influences organization of somatic sensory cortex. Nature. Apr. 1987; 326(6114): 694-7.
Sohal et al., Parvalbumin neurons and gamma rhythms enhance cortical circuit performance. Nature. Jun. 2009; 459(7247): 698-702.
Swerdlow et al., Sensorimotor gating of the startle reflex: what we said 25 years ago, what has happened since then, and what comes next. J Psychopharmacol. Nov. 2016;30(11):1072-1081. doi: 10.1177/0269881116661075. Epub Aug. 16, 2016.
Tata et al., Lack of cognitive recovery following withdrawal from long-term benzodiazepine use. Psychol Med. Feb. 1994; 24(1): 203-13.
Tomassy et al. Developmental abnormalities of cortical interneurons precede symptoms onset in a mouse model of Rett syndrome. J Neurochem. Oct. 2014; 131(1): 115-27.
Tomchek et al., Sensory processing in children with and without autism: a comparative study using the short sensory profile. Am J Occup Ther. Mar. 1, 2007; 61(2): 190-200.
Torres et al., Autism: the micro-movement perspective. Front Integr Neurosci. Jul. 24, 2013;7: 32.
Trapani et al., Structure-activity relationships and effects on neuroactive steroid synthesis in a series of 2-phenylimidazo[1,2-a]pyridineacetamide peripheral benzodiazepine receptors ligands. J Med Chem. Jan. 13, 2005;48(1):292-305. doi: 10.1021/jm049610q.
Trapani et al., Synthesis and binding affinity of 2-phenylimidazo[1,2-alpha]pyridine derivatives for both central and peripheral benzodiazepine receptors. A new series of high-affinity and selective ligands for the peripheral type. J Med Chem. Sep. 12, 1997;40(19):3109-18. doi: 10.1021/jm970112+.
Tuccinardi et al., A virtual screening study of the 18 kDa translocator protein using pharmacophore models combined with 3D-QSAR studies. ChemMedChem. Oct. 2009;4(10):1686-94. doi: 10.1002/cmdc.200900254.
Usoskin et al., Unbiased classification of sensory neuron types by large-scale single-cell RNA sequencing. Nature neuroscience. Jan. 2015; 18(1): 145-53.
Veenstra-Danderweele et al., Arbaclofen in Children and Adolescents with Autism Spectrum Disorder: A Randomized, Controlled, Phase 2 Trial. Neuropsychopharmacology. Jun. 2017; 42(7): 1390-8.
Voos et al., Autistic traits are associated with diminished neural response to affective touch. Soc Cogn Affect Neurosci. Apr. 2013;8(4):378-86. doi: 10.1093/scan/nss009. Epub Jan. 20, 2012.
Wang et al., Striatopallidal dysfunction underlies repetitive behavior in Shank3-deficient model of autism. The Journal of Clinical Investigation. May 1, 2017; 127(5): 1978-90.
Waszczak et al., GABAergic actions of THIP in vivo and vitro: a comparison with muscimol and GABA. Eur J Pharmacol. Jul. 11, 1980;65(1):21-9. doi: 10.1016/0014-2999(80)90204-6.
Watanabe et al., Disruption of the epilepsy KCNQ2 gene results in neural hyperexcitability. J Neurochem. Jul. 2000; 75(1): 28-33.
Wiesel et al., Extent of recovery from the effects of visual deprivation in kittens. Journal of neurophysiology. Nov. 1, 1965; 28(6): 1060-72.
Wiggins et al., Brief report: sensory abnormalities as distinguishing symptoms of autism spectrum disorders in young children. J Autism Dev Disord. Jul. 1, 2009; 39(7): 1087- 91.
Womelsdorf et al., Dynamic circuit motifs underlying rhythmic gain control, gating and integration. Nature neuroscience. Aug. 2014; 17(8): 1031-9.
Wright, Cognition and behavior: Sensory sensitivity tied to autism, Oct. 10, 2012, available at https://www.spectrumnews.org/news/cognition-and-behavior-sensory-sensitivity-tied-to-autism/.
Yatawara et al., The effect of oxytocin nasal spray on social interaction deficits observed in young children with autism: a randomized clinical crossover trial. Mol Psychiatry. Sep. 2016; 21(9): 1225-31.
Yi et al., Autism- associated SHANK3 haploinsufficiency causes Ih channelopathy in human neurons. Science. May 6, 2016; 352(6286): aaf2669.
Zeilhofer et al., Fast synaptic inhibition in spinal sensory processing and pain control. Physiological reviews. Jan. 2012; 92(1): 193-235.
Zheng et al., Suppression of KCNQ/M (Kv7) potassium channels in dorsal root ganglion neurons contributes to the development of bone cancer pain in a rat model. Pain. Mar. 1, 2013; 154(3): 434-48.
Zikopoulos et al., Altered neural connectivity in excitatory and inhibitory cortical circuits in autism. Front Hum Neurosci. Sep. 27, 2013; 7: 609.
Extended European Search Report for Application No. 20810565.0, mailed Jun. 29, 2023.
No Author Listed, Pubchem CID 3393. Flurazepam compound summary. Entered Mar. 25, 2005. 81 pages.
No Author Listed, Caplus Chemical Abstracts Service for U.S. Pat. No. 9,586,890. 2017. 3 pages.
Ogata et al., 5-Aryl-1,5-dihydro-2H-1,4-benzodiazepin-2-one derivatives as antianxiety agents. J Med Chem. Jun. 1977;20(6):776-81. doi: 10.1021/jm00216a008.
Pavlovsky et al., Synthesis and anticonvulsant activity of 3- alkoxy-1,2-dihydro-3H-1,4-benzodiazepin-2-ones. Pharmaceutical Chemistry Journal. 2012; 46(9): 540-545. DOI: 10.1007/s11094-012-0842-9.

Key

Wash, 60s   30µM GABA, 2s

Test conc 1-7, 2s

|  | Allosteric Modulation | | | | Agonist Activity | |
| --- | --- | --- | --- | --- | --- | --- |
| Compound | hGABAA a1b3g2 EC50(uM) | Mean Maximum Effect (% of Control) | hGABAA a2b3g2 EC50(uM) | Mean Maximum Effect (% of Control) | hGABAA a1b3g2 EC50(uM) | hGABAA a2b3g2 EC50(uM) |
| Isoguvacine | - | - | - | - | 23.3 | 18.7 |
| GABA | - | - | - | - | 3.2 | 3.3 |
| 1* | 0.654 | 282 | 3 | 181 | - | - |
| 2* | 0.446 | 354 | 2 | 248 | - | - |
| 3* | 0.081 | 331 | 1.1 | 240 | - | - |
| 4* | 2.47 | 170 | 5.8 | 126 | - | - |
| 5** | 3.16 | 136 | 8.7 | 126 | - | - |
| 6* | - | 130 | - | 122 | - | - |
| 36 | - | - | 1.2 | 180.1 | - | - |
| 37 | - | - | 9.6 | 192.8 | - | - |
| 38 | - | - | 3.5 | 209.9 | - | - |
| 39 | - | - | 1.7 | 208 | - | - |
| 34 | - | - | - | 139.9 | - | - |
| 35 | - | - | - | 143.8 | - | - |

* HCl salt; ** TFA salt

FIG. 12

COMPOSITIONS AND METHODS FOR REDUCING TACTILE DYSFUNCTION, ANXIETY, AND SOCIAL IMPAIRMENT

REFERENCE TO RELATED APPLICATIONS

This application is a continuation of and claims priority under 35 U.S.C. § 120 to U.S. Ser. No. 17/058,403, filed Nov. 24, 2020, which is a national stage filing under 35 U.S.C. § 371 of international PCT application, PCT/US2019/034390, filed May 29, 2019, which claims priority under 35 U.S.C. § 119(e) to U.S. Ser. No. 62/677,367, filed on May 29, 2018, each of which is incorporated herein by reference in its entirety.

STATEMENT AS TO FEDERALLY SPONSORED RESEARCH

This invention was made with government support under NS097344 and NS101057 awarded by the National Institutes of Health. The government has certain rights in the invention.

BACKGROUND OF THE INVENTION

Autism spectrum disorder (ASD) is a highly prevalent class of neurodevelopmental disorders characterized by impairments in social communication and interactions, as well as restricted and repetitive behaviors. Rates of ASD diagnoses are increasing, and the CDC identifies one in every 59 children in the United States as having ASD. In the United States alone, it is estimated that the ASD-related healthcare costs exceed 230 billion dollars per year, or 1.4 million per individual with ASD over their lifetime. A majority of ASD patients (60.9%) report altered tactile sensitivity in both glabrous (smooth) and hairy skin, and altered sensitivity to vibration and thermal pain. As with idiopathic or non-syndromic ASD, pervasive developmental disorders that cause syndromic forms of ASD are also associated with disrupted somatosensation. For example, abnormalities in tactile perception are observed in patients with Phelan McDermid Syndrome (PMS) and Fragile X syndrome, which are both highly associated with ASD and are caused by mutations in Shank3 and Fmr1, respectively. Similarly, tactile hypersensitivity is common in patients with Rett syndrome (RTT), which is caused by mutations in the X-linked methyl-CpG-binding protein 2 (Mecp2) gene. There is an inverse correlation between the presence of ASD traits in human subjects and their neural responses to C-low-threshold mechanoreceptor (LTMR)-targeted affective touch. Currently, there are no FDA-approved treatments for ASD. Thus, a critical need exists for novel therapeutic approaches to treat ASD and related disorders such as Rett syndrome, Phelan McDermid Syndrome, and Fragile X syndrome.

SUMMARY OF THE INVENTION

In one aspect, provided herein is compound having the structure of Formula (I):

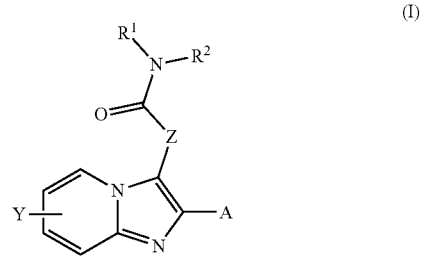

wherein
A is optionally substituted $C_{6-10}$ aryl or optionally substituted heteroaryl;
Y is hydrogen, deuterium, halogen, or optionally substituted $C_{1-4}$ alkyl;
Z is oxygen, $NR^3$, or $CR^3R^4$;
$R^1$ is optionally substituted alkylcarboxylic acid, optionally substituted alkylcarboxylic acid ester, optionally substituted alkylcarboxylic acid amide, optionally substituted $C_{1-6}$ alkylamino, optionally substituted heteroalkyl, or optionally substituted $C_{1-6}$ alkyl with at least one $C_{3-7}$ heterocycle comprising 1-3 nitrogen atoms, 1-2 oxygen atoms, or combinations thereof;
$R^2$ is optionally substituted $C_{1-6}$ alkyl, optionally substituted heteroalkyl, or optionally substituted $C_{3-6}$ cycloalkyl;
or $R^1$ and $R^2$ together form an optionally substituted $C_{3-6}$ cycloalkyl or optionally substituted $C_{3-6}$ heterocycle; and
each of $R^3$ and $R^4$ is, independently, hydrogen, deuterium, or optionally substituted $C_{1-6}$ alkyl;
or a pharmaceutically acceptable salt thereof.

In certain embodiments, the compound of Formula (I) has the structure of Formula (III):

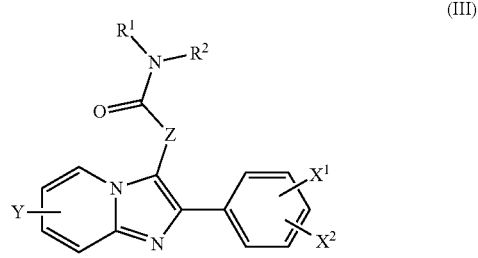

wherein
each of $X^1$ and $X^2$ is, independently, hydrogen, deuterium, halogen, $C_{1-4}$ alkoxy, $C_{1-6}$ alkyl, $CF_3$, $CH_3S$, $CH_3SO_2$, $NR^5R^6$, or $NO_2$; and each of $R^5$ and $R^6$ is, independently, hydrogen, deuterium, optionally substituted $C_{1-6}$ alkyl, optionally substituted $C_{3-6}$ cycloalkyl, acyl, carbamate, sulfonamide, or urea;
or a pharmaceutically acceptable salt thereof.

In certain embodiments, the compound of Formula (III) has the structure of Formula (V):

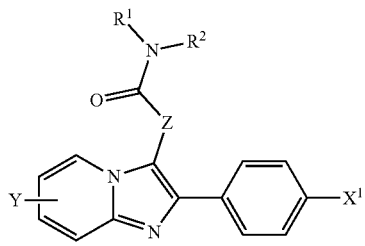

(V)

wherein
- $X^1$ is hydrogen, deuterium, halogen, $C_{1-4}$ alkoxy, $C_{1-6}$ alkyl, $CF_3$, $CH_3S$, $CH_3SO_2$, or $NO_2$;
- Y is hydrogen, deuterium, halogen, or $C_{1-4}$ alkyl;
- $R^2$ is optionally substituted $C_{1-6}$ alkyl; or
- $R^1$ and $R^2$ together form an optionally substituted $C_{3-6}$ cycloalkyl or optionally substituted $C_{3-6}$ heterocycle;

or a pharmaceutically acceptable salt thereof.

In certain embodiments, the compound of Formula (III) has the structure of Formula (VII):

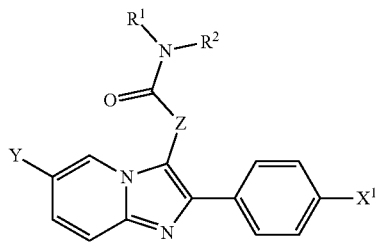

(VII)

wherein
- Z is oxygen, NH, or $CH_2$;
- $R^1$ is optionally substituted $C_{1-6}$ alkylamino; and
- $R^2$ is optionally substituted $C_{1-6}$ alkyl;

or a pharmaceutically acceptable salt thereof.

In another aspect, provided herein is a compound of Formula (II):

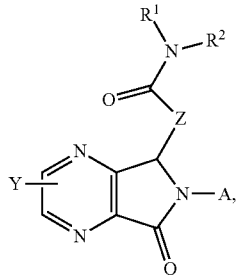

(II)

wherein
- A is optionally substituted $C_{6-10}$ aryl or optionally substituted heteroaryl;
- Y is hydrogen, deuterium, halogen, or optionally substituted $C_{1-4}$ alkyl;
- Z is oxygen, $NR^3$, or $CR^3R^4$;
- $R^1$ is optionally substituted alkylcarboxylic acid, optionally substituted alkylcarboxylic acid ester, optionally substituted alkylcarboxylic acid amide, optionally substituted $C_{1-6}$ alkylamino, or optionally substituted $C_{1-6}$ alkyl with at least one $C_{3-7}$ heterocycle comprising 1-3 nitrogen atoms, 1-2 oxygen atoms, or combinations thereof;
- $R^2$ is optionally substituted $C_{1-6}$ alkyl or optionally substituted $C_{3-6}$ cycloalkyl;
- or $R^1$ and $R^2$ together form an optionally substituted $C_{3-6}$ cycloalkyl or optionally substituted $C_{3-6}$ heterocycle; and
- each of $R^3$ and $R^4$ is, independently, hydrogen, deuterium, or optionally substituted $C_{1-6}$ alkyl;

or a pharmaceutically acceptable salt thereof.

In certain embodiments, the compound of Formula (II) has the structure of Formula (IIa) or Formula (IIb):

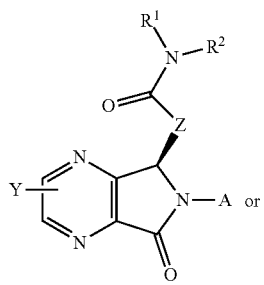

(IIa)

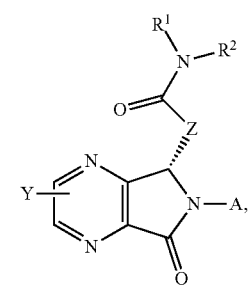

(IIb)

or a pharmaceutically acceptable salt thereof.

In certain embodiments, the compound of Formula (II) has the structure of Formula (IV):

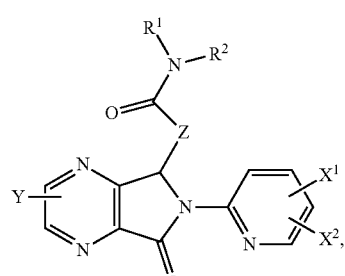

(IV)

wherein
- each of $X^1$ and $X^2$ is, independently, hydrogen, deuterium, halogen, $C_{1-4}$ alkoxy, $C_{1-6}$ alkyl, $CF_3$, $NR^5R^6$, or $NO_2$; and
- each of $R^5$ and $R^6$ is, independently, hydrogen, deuterium, optionally substituted $C_{1-6}$ alkyl, optionally substituted $C_{3-6}$ cycloalkyl, acyl, carbamate, sulfonamide, or urea;

or a pharmaceutically acceptable salt thereof.

In certain embodiments, the compound of Formula (IV) has the structure of Formula (IVa) or Formula (IVb):

(IVa)

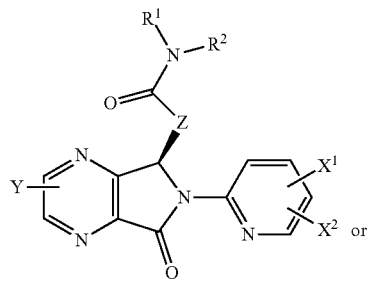

(IVb)

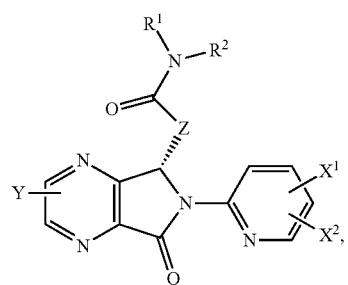

or a pharmaceutically acceptable salt thereof.

In certain embodiments, the compound of Formula (II) has the structure of Formula (VI):

(VI)

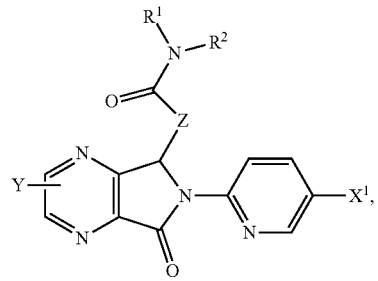

wherein
  $X^1$ is hydrogen, deuterium, halogen, $C_{1-4}$ alkoxy, $C_{1-6}$ alkyl, $CF_3$, $CH_3S$, $CH_3SO_2$, or $NO_2$;
  Y is hydrogen, deuterium, halogen, or $C_{1-4}$ alkyl;
  $R^2$ is optionally substituted $C_{1-6}$ alkyl; or
  $R^1$ and $R^2$ together form an optionally substituted $C_{3-6}$ cycloalkyl or optionally substituted $C_{3-6}$ heterocycle;
or a pharmaceutically acceptable salt thereof.

In certain embodiments, the compound of Formula (VI) has the structure of Formula (VIa) or Formula (VIb):

(VIa)

(VIb)

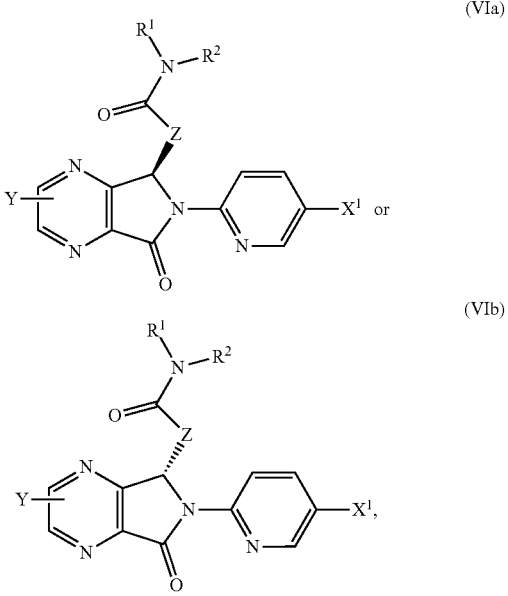

or a pharmaceutically acceptable salt thereof.

In certain embodiments, the compound of Formula (VI) has the structure of Formula (VIII):

(VIII)

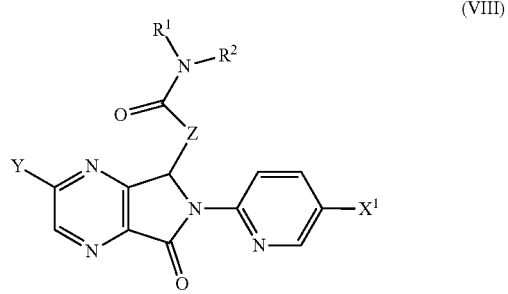

wherein
  Z is oxygen, NH, or $CH_2$;
  $R^1$ is optionally substituted $C_{1-6}$ alkylamino; and
  $R^2$ is optionally substituted $C_{1-6}$ alkyl;
or a pharmaceutically acceptable salt thereof.

In certain embodiments, the compound of Formula (VIII) has the structure of Formula (VIIIa) or Formula (VIIIb):

(VIIIa)

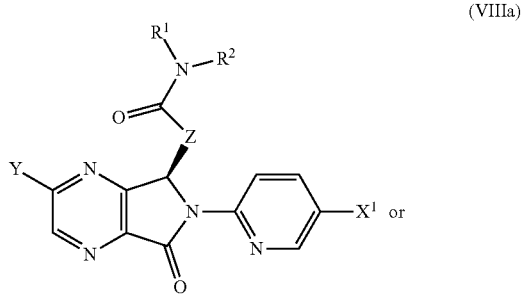

-continued

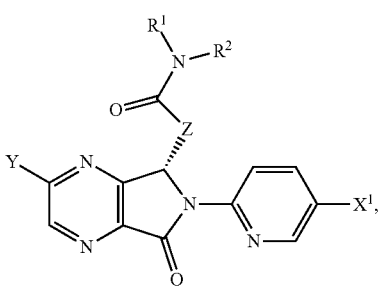
(VIIIb)

or a pharmaceutically acceptable salt thereof.

In certain specific embodiments of any of the preceding aspects and embodiments:

A is optionally substituted $C_{6-10}$ aryl; or A is optionally substituted heteroaryl;

$X^1$ is hydrogen, halogen, or $C_{1-6}$ alkyl; $X^1$ is hydrogen; $X^1$ is halogen; $X^1$ is chlorine; $X^1$ is $C_{1-6}$ alkyl; or $X^1$ is $CH_3$;

$X^2$ is hydrogen;

Y is hydrogen, halogen, or $C_{1-4}$ alkyl; Y is hydrogen; Y is halogen; Y is chlorine; Y is $C_{1-4}$ alkyl; or Y is $CH_3$;

Z is oxygen; or Z is $CH_2$; and/or $R^1$ is

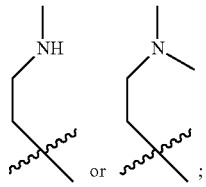

$R^1$ comprises a carboxylic acid or carboxylate moiety;

$R^1$ is optionally substituted $C_{2-4}$ alkylamino, and $R^2$ is optionally substituted $C_{1-3}$ alkyl; or $R^1$ and $R^2$ together form an optionally substituted $C_{3-6}$ cycloalkyl or optionally substituted $C_{3-6}$ heterocycle, optionally wherein the $C_{3-6}$ cycloalkyl or $C_{3-6}$ heterocycle is substituted with an alkylcarboxylic acid, an alkylcarboxylic acid ester, or an alkylcarboxylic acid amide.

In another aspect, provided herein is a pharmaceutical composition comprising a compound of any of the above embodiments (e.g., the compounds of any one of Formulas I-XIII; e.g., the compounds of Table 1, or a pharmaceutically acceptable salt thereof) and a pharmaceutically acceptable excipient.

In another aspect, the invention features a method of reducing tactile dysfunction in a human subject diagnosed with Autism Spectrum Disorder (ASD), Rett syndrome (RTT), Phelan McDermid syndrome (PMS), or Fragile X syndrome by administering to the subject a compound of any of the above embodiments (e.g., the compounds of any one of Formulas I-XIII; e.g., the compounds of Table 1, or a pharmaceutically acceptable salt thereof) in an amount and for a duration sufficient to reduce the tactile dysfunction.

In another aspect, the invention features a method of reducing anxiety or social impairment in a subject (e.g., a human) diagnosed with ASD, RTT, PMS, or Fragile X syndrome by administering to the subject a compound of any of the above embodiments (e.g., the compounds of any one of Formulas I-XIII; e.g., the compounds of Table 1, or a pharmaceutically acceptable salt thereof) in an amount and for a duration sufficient to reduce the anxiety or social impairment.

In another aspect, the provided herein is a method of treating touch over-reactivity and/or pain and/or mechanical allodynia in a human subject in need thereof, comprising administering to the subject a compound of any of the above embodiments (e.g., the compounds of any one of Formulas I-XIII; e.g., the compounds of Table 1, or a pharmaceutically acceptable salt thereof) in an amount and for a duration sufficient to reduce the touch over-reactivity and/or pain and/or mechanical allodynia.

Definitions

As used herein, the terms "Autism Spectrum Disorder" or "ASD" refer to a heterogeneous group of neurodevelopmental disorders as classified in the fifth revision of the American Psychiatric Association's Diagnostic and Statistical Manual of Mental Disorders 5th edition (DSM-5). The DSM-5 redefined the autism spectrum to encompass the prior (DSM-IV-TR) diagnosis of autism, Asperger syndrome, pervasive developmental disorder not otherwise specified, childhood disintegrative disorder, and Rett syndrome. The autism spectrum disorders are characterized by social deficits and communication difficulties, stereotyped or repetitive behaviors and interests, and in some cases, cognitive delays. For example, an ASD is defined in the DSM-5 as exhibiting (i) deficits in social communication and interaction not caused by general developmental delays (must exhibit three criteria including deficits in social-emotional reciprocity, deficits in nonverbal communication, and deficits in creating and maintaining relationships appropriate to developmental level), (ii) demonstration of restricted and repetitive patterns of behavior, interest or activities (must exhibit two of the following four criteria: repetitive speech, repetitive motor movements or repetitive use of objects, adherence to routines, ritualized patterns of verbal or nonverbal, or strong resistance to change, fixated interests that are abnormally intense of focus, and over or under reactivity to sensory input or abnormal interest in sensory aspects of environment), (iii) symptoms must be present in early childhood, and (iv) symptoms collectively limit and hinder everyday functioning. The term "ASD" is also contemplated herein to include Dravet's syndrome and autistic-like behavior in non-human animals.

As used herein, the terms "Rett syndrome" or "RTT" refer to an X-linked disorder that affects approximately one in ten-thousand girls. Patients go through four stages: Stage I) Following a period of apparently normal development from birth, the child begins to display social and communication deficits, similar to those seen in other autism spectrum disorders, between six and eighteen months of age. The child shows delays in their developmental milestones, particularly for motor ability, such as sitting and crawling. Stage II) Beginning between one and four years of age, the child goes through a period of regression in which they lose speech and motor abilities, developing stereotypical midline hand movements and gait impairments. Breathing irregularities, including apnea and hyperventilation also develop during this stage. Autistic symptoms are still prevalent at this stage. Stage III) Between age two and ten, the period of regression ends and symptoms plateau. Social and communication skills may show small improvements during this plateau period, which may last for most of the patients' lives. Stage IV) Motor ability and muscle deterioration continues. Many girls develop severe scoliosis and lose the ability to walk.

As used herein, the terms "Phelan McDermid syndrome" or "PMS" refer to rare genetic condition caused by a deletion or other structural change of the terminal end of chromosome 22 in the 22q13 region or a disease-causing mutation of the Shank3 gene. Although the range and severity of symptoms may vary, PMS is generally thought to be characterized by neonatal hypotonia (low muscle tone in the newborn), normal growth, absent to severely delayed speech, moderate to profound developmental delay, and minor dysmorphic features. People who have PMS often show symptoms in very early childhood, sometimes at birth and within the first six months of life.

As used herein, the term "Fragile X syndrome" refers to an X chromosome-linked condition that is characterized by a visible constriction near the end of the X chromosome, at locus q27.3 that causes intellectual disability, behavioral and learning challenges and various physical characteristics Fragile X syndrome is the most common inherited form of mental retardation and developmental disability. Males with Fragile X syndrome usually have mental retardation and often exhibit characteristic physical features and behavior. Fragile X syndrome is characterized by behavior similar to autism and attention deficit disorder, obsessive-compulsive tendencies, hyperactivity, slow development of motor skills and anxiety fear disorder. When these disabilities are severe and occur simultaneously, the condition is sometimes described as autism, and may be associated with any degree of intelligence. Other characteristics are a likable, happy, friendly personality with a limited number of autistic-like features such as hand-flapping, finding direct eye contact unpleasant, and some speech and language problems. Physical features may include large ears, long face, soft skin and large testicles (called "macroorchidism") in post-pubertal males. Connective tissue problems may include ear infections, flat feet, high arched palate, double-jointed fingers and hyper-flexible joints.

As used herein, the term "tactile dysfunction" refers to exhibiting symptoms such as withdrawing when being touched, refusing to eat certain "textured" foods and/or to wear certain types of clothing, complaining about having hair or face washed, avoiding getting hands dirty (e.g., glue, sand, mud, finger-paint), and using finger tips rather than whole hands to manipulate objects. Tactile dysfunction may lead to a misperception of touch and/or pain (hyper- or hyposensitive) and may lead to self-imposed isolation, general irritability, distractibility, and hyperactivity.

As used herein, the term "anxiety" refers to emotions characterized by feelings of tension, worried thoughts and physical changes like increased blood pressure. Anxiety can be characterized by having recurring intrusive thoughts or concerns, avoiding certain situations (e.g., social situations) out of worry, and physical symptoms such as sweating, trembling, dizziness, or a rapid heartbeat.

As used herein, the term "social impairment" refers to a distinct dissociation from and lack of involvement in relations with other people. It can occur with various mental and developmental disorders, such as autism. Social impairment may occur when an individual acts in a less positive way or performs worse when they are around others as compared to when alone. Nonverbal behaviors associated with social impairment can include deficits in eye contact, facial expression, and gestures that are used to help regulate social interaction. Often there is a failure to develop age-appropriate friendships. Social impairment can also include a lack of spontaneous seeking to share achievements or interests with other individuals. A person with social impairment may exhibit a deficit in social reciprocity with individuals, decreased awareness of others, lack of empathy, and lack of awareness of the needs of others.

As used herein, the terms "blood brain barrier" and "BBB" refer to a transvascular permeability barrier that tightly controls entry of substances into the brain. The capillaries that perfuse the brain are lined with special endothelial cells that lack fenestrations and are sealed by endothelial tight junctions. The tight endothelium provides a physical barrier that together with metabolic barriers forms the basis of the BBB.

As used herein, the term "reduced permeability" refers to peripherally acting compositions of the compounds described herein that have decreased (e.g., by 10%, 20%, 30%, 40%, 50%, 60%, 70%, 80%, 90%, or 100%) ability to cross the blood brain barrier.

As used herein, the term "reducing" refers to decreasing (e.g., by 1%, 2%, 3%, 4%, 5%, 6%, 7%, 8%, 9%, 10%, 20%, 30%, 40%, 50%, 60%, 70%, 80%, 90%, 95%, 97%, 99%, or about 100%) the side effects or symptoms (e.g., tactile sensitivity, social impairment, or anxiety) of patients diagnosed with ASD, RTT, PMS, or Fragile X syndrome.

As used herein, the terms "treatment" or "treating" refer to reducing, decreasing, decreasing the risk of progression, or decreasing the side effects of (e.g., by 1%, 2%, 3%, 4%, 5%, 6%, 7%, 8%, 9%, 10%, 20%, 30%, 40%, 50%, 60%, 70%, 80%, 90%, 95%, 97%, 99%, or about 100%) a particular disease or condition (e.g., tactile dysfunction, anxiety, and social impairment, e.g., ASD, RTT, PMS, and Fragile X syndrome). Reducing, decreasing, decreasing the risk of progression, or decreasing the side effects of are relative to a subject who did not receive treatment, e.g., a control, a baseline, or a known control level or measurement.

As used herein, the terms "effective amount" or "therapeutically effective amount" refers to an amount of a compound of the invention sufficient to produce a desired result, for example, reducing (e.g., by 10%, 20%, 30%, 40%, 50%, 60%, 70%, 80%, 90%, or 100%) tactile dysfunction, social impairment, or anxiety in a subject upon administration of a composition containing a compound described herein. The increase or reduction related to administration of an effective amount of a compound may be calculated relative to levels or symptoms, as applicable, in a subject that has not been administered a compound of the invention or relative to the subject prior to administration of a compound of the invention. The increase or reduction may also be calculated relative to a control or baseline average.

As used herein, the term "subject," refers to any animal (e.g., a mammal, e.g., a human). A subject to be treated according to the methods described herein may be one who has been diagnosed with a developmental disorder (e.g., ASD, RTT, PMS, and Fragile X syndrome) as having such a condition or one at risk of developing the condition. Diagnosis may be performed by any method or technique known in the art. One skilled in the art will understand that a subject to be treated according to the present invention may have been subjected to standard tests or may have been identified, without examination, as one at high risk due to the presence of one or more risk factors. In certain particular embodiments, the subject is a human. In certain particular embodiments, the subject is an adult. In certain particular embodiments, the subject is an adolescent. In other particular embodiments, the subject is a child. In certain embodiments, the child is less than 12 years of age. In certain embodiments, the child is less than 10 years of age. In certain embodiments, the child is less than 8 years of age. In certain embodiments, the child is less than 6 years of age. In certain embodiments, the child is less than 4 years of age. In certain embodiments, the child is less than 2 years of age. In certain embodiments, the child is 2-4 years of age. In certain embodiments, the child is 4-6 years of age. In certain embodiments, the child is 6-8 years of age. In certain embodiments, the child is 8-10 years of age. In certain embodiments, the child is greater than 12 years of age.

As used herein, the term "pharmaceutical composition," refers to a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); for intrathecal administration (e.g., as a sterile preservative-free composition in a solvent system suitable for intrathecal use); or in any other formulation described herein.

As used herein, the terms "pharmaceutically acceptable excipient" or "pharmaceutically acceptable carrier," refer to any ingredient in a pharmaceutical composition other than compounds described herein (e.g., a vehicle capable of suspending or dissolving the active agent) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene, calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

As used herein, the term "pharmaceutically acceptable salt," refers to those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, gluceptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. In certain particular embodiments, a compound described herein is provided as a hydrochloride salt.

The term "Log P" is the partition coefficient reflecting the relative solubility of a drug in octanol versus water. The higher the value, the lower the water solubility. Generally a reduction in the Log P is associated with reduced permeability across the blood brain barrier. Log P can be predicted from the structure of a compound described herein using standard physiochemical prediction software.

The term "polar surface area (PSA)" refers to the polar surface area of a molecule and is a reflection of the polarity of the molecule. Generally, higher PSA is associated with reduced permeability across the blood brain barrier. PSA can be predicted from the structure of a compound described herein using standard physiochemical prediction software.

The term "freely rotatable bonds (FRBs)" refer to the number of freely rotatable bonds a compound has. A greater number of freely rotatable bonds generally correlates with lower blood brain permeability. FRBs can be determined from the structure of a compound described herein using standard physiochemical prediction software.

The term "acyl," as used herein, represents a hydrogen or an alkyl group, as defined herein that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-6}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., 2-methylpentyl, 3-methylpentyl, 2,2-dimethylbutyl, 2,3-dimethylbutyl, and n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-10}$ alkyl (such as substituted $C_{1-6}$ alkyl, e.g., —$CH_2F$, —$CHF_2$, —$CF_3$ or benzyl (Bn)). An alkylene is a divalent alkyl group.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl. In certain more particular embodiments, the heteroalkyl comprises polyethylene glycol. Polyethylene glycol may have 2 or more ethylene glycol repeat units, e.g., about 2, 4, 6, 10, 12, 14, 16, 18, 20, 22, 24, 26, 28, or 30 ethylene glycol repeat units.

The term "alkylamino," as used herein, refers to a heteroalkyl group, as defined herein, in which one or more of the constituent carbon atoms have been replaced by nitrogen. In some embodiments, the heteroalkyl group can be further substituted with 1, 2, 3, or 4 substituent groups as described herein for alkyl groups. Examples of alkylamino groups are methylamino and ethylamino.

The term "amino," as used herein, represents —$N(R^{N1})_2$, wherein each $R^{N1}$ is, independently, H, OH, $NO_2$, $N(R_{N2})_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $RN^1$ combine to form an alkylene or heteroalkylene, and wherein each $R^{N2}$ is, independently, H, alkyl, or aryl. The amino groups of the invention can be an unsubstituted amino (i.e., —$NH_2$) or a substituted amino (i.e., —$N(R^{N1})_2$).

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, indenyl, and the like, and may be optionally substituted with 1, 2, 3, 4, or 5 substituents independently selected from the group consisting of: (1) $C_1$-$C_7$ acyl (e.g., carboxyaldehyde); (2) $C_1$-$C_{20}$ alkyl (e.g., $C_1$-$C_6$ alkyl, $C_1$-$C_6$ alkoxy-$C_1$-$C_6$ alkyl, $C_1$-$C_6$ alkylsulfinyl-$C_1$-$C_6$ alkyl, amino-$C_1$-$C_6$ alkyl, azido-$C_1$-$C_6$ alkyl, (carboxyaldehyde)-$C_1$-$C_6$ alkyl, halo-$C_1$-$C_6$ alkyl (e.g., perfluoroalkyl), optionally substituted hydroxyl-$C_1$-$C_6$ alkyl, nitro-$C_1$-$C_6$ alkyl, or $C_1$-$C_6$ thioalkoxy-$C_1$-$C_6$ alkyl); (3) $C_1$-$C_{20}$ alkoxy (e.g., $C_1$-$C_6$ alkoxy, such as perfluoroalkoxy); (4) $C_1$-$C_6$ alkylsulfinyl; (5) $C_6$-$C_{10}$ aryl; (6) amino; (7) $C_1$-$C_6$ alk-$C_6$-$C_{10}$ aryl; (8) azido; (9) $C_{3-8}$ cycloalkyl; (10) $C_1$-$C_6$ alk-$C_{3-8}$ cycloalkyl; (11) halo; (12) $C_1$-$C_{12}$ heterocyclyl (e.g., $C_1$-$C_{12}$ heteroaryl); (13) ($C_1$-$C_{12}$ heterocyclyl)oxy; (14) optionally substituted hydroxyl; (15) nitro; (16) $C_1$-$C_{20}$ thioalkoxy (e.g., $C_1$-$C_6$ thioalkoxy); (17) —$(CH_2)_qCO_2R^{A'}$, where q is an integer from zero to four, and $R^{A'}$ is selected from the group consisting of (a) $C_1$-$C_6$ alkyl, (b) $C_6$-$C_{10}$ aryl, (c) hydrogen, and (d) $C_1$-$C_6$ alk-$C_6$-$C_{10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_1$-$C_6$ alkyl, (c) $C_6$-$C_{10}$ aryl, and (d) $C_1$-$C_6$ alk-$C_6$-$C_{10}$ aryl; (19) —$(CH_2)_qSO_2R^{D'}$, where q is an integer from zero to four and where $R^{D'}$ is selected from the group consisting of (a) alkyl, (b) $C_6$-$C_{10}$ aryl, and (c) alk-$C_6$-$C_{10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_1$-$C_6$ alkyl, (c) $C_6$-$C_{10}$ aryl, and (d) $C_1$-$C_6$ alk-$C_6$-$C_{10}$ aryl; (21) optionally substituted thiol; (22) $C_6$-$C_{10}$ aryloxy; (23) $C_{3-8}$ cycloalkoxy; (24) $C_6$-$C_{10}$ aryl-$C_1$-$C_6$ alkoxy; (25) $C_1$-$C_6$ alk-$C_1$-$C_{12}$ heterocyclyl (e.g., $C_1$-$C_6$ alk-$C_1$-$C_{12}$ heteroaryl); (26) $C_2$-$C_{20}$ alkenyl; (27) $C_2$-$C_{20}$ alkynyl; and (28) nitrile groups (e.g., cyano). In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "heteroaryl," as used herein, represents a radical of a 5-14 membered monocyclic or polycyclic (e.g., bicyclic, tricyclic) 4n+2 aromatic ring system (e.g., having 6, 10, or 14 ☐ electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group be monovalent or may have more than one point of attachment to another moiety (e.g., it may be divalent, trivalent, etc), although the valency may be specified directly in the name of the group. For example, "triazoldiyl" refers to a divalent triazolyl moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "cycloalkyl," as used herein, represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicycle heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like. The cycloalkyl groups of this invention can be optionally substituted with: (1) $C_1$-$C_7$ acyl (e.g., carboxyaldehyde); (2) $C_1$-$C_{20}$ alkyl (e.g., $C_1$-$C_6$ alkyl, $C_1$-$C_6$ alkoxy-$C_1$-$C_6$ alkyl, $C_1$-$C_6$ alkylsulfinyl-$C_1$-$C_6$ alkyl, amino-$C_1$-$C_6$ alkyl, azido-$C_1$-$C_6$ alkyl, (carboxyaldehyde)-$C_1$-$C_6$ alkyl, halo-$C_1$-$C_6$ alkyl (e.g., perfluoroalkyl), optionally substituted hydroxyl-$C_1$-$C_6$ alkyl, nitro-$C_1$-$C_6$ alkyl, or $C_1$-$C_6$ thioalkoxy-$C_1$-$C_6$ alkyl); (3) $C_1$-$C_{20}$ alkoxy (e.g., $C_1$-$C_6$ alkoxy, such as perfluoroalkoxy); (4) $C_1$-$C_6$ alkylsulfinyl; (5) $C_6$-$C_{10}$ aryl; (6) amino; (7) $C_1$-$C_6$ alk-$C_6$-$C_{10}$ aryl; (8) azido; (9) $C_{3-8}$ cycloalkyl; (10) $C_1$-$C_6$ alk-$C_{3-8}$ cycloalkyl; (11) halo; (12) $C_1$-$C_{12}$ heterocyclyl (e.g., $C_1$-$C_{12}$ heteroaryl); (13) ($C_1$-$C_{12}$ heterocyclyl)oxy; (14) optionally substituted hydroxyl; (15) nitro; (16) $C_1$-$C_{20}$ thioalkoxy (e.g., $C_1$-$C_6$ thioalkoxy); (17) —$(CH_2)_qCO_2R^{A'}$, where q is an integer from zero to four, and $R^{A'}$ is selected from the group consisting of (a) $C_1$-$C_6$ alkyl, (b) $C_6$-$C_{10}$ aryl, (c) hydrogen, and (d) $C_1$-$C_6$ alk-$C_6$-$C_{10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_6$-$C_{10}$ alkyl, (c) $C_6$-$C_{10}$ aryl, and (d) $C_1$-$C_6$ alk-$C_6$-$C_{10}$ aryl; (19) —$(CH_2)_qSO_2R^{D'}$, where q is an integer from zero to four and where $R^{D'}$ is selected from the group consisting of (a) $C_6$-$C_{10}$ alkyl, (b) $C_6$-$C_{10}$ aryl, and (c) $C_1$-$C_6$ alk-$C_6$-$C_{10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_6$-$C_{10}$ alkyl, (c) $C_6$-$C_{10}$ aryl, and (d) $C_1$-$C_6$ alk-$C_6$-$C_{10}$ aryl; (21) optionally substituted thiol; (22) $C_6$-$C_{10}$ aryloxy; (23) $C_{3-8}$ cycloalkoxy; (24) $C_6$-$C_{10}$ aryl-$C_1$-$C_6$ alkoxy; (25) $C_1$-$C_6$ alkl-$C_1$-$C_{12}$ heterocyclyl (e.g., $C_1$-$C_6$ alk-$C_1$-$C_{12}$ heteroaryl); (26) oxo; (27) $C_2$-$C_{20}$ alkenyl; and (28) $C_2$-$C_{20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "halogen," as used herein, refers to bromine, chlorine, iodine, or fluorine.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999). N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "O-protecting group," as used herein, represents those groups intended to protect an oxygen containing (e.g., phenol, optionally substituted hydroxyl, or carbonyl) group against undesirable reactions during synthetic procedures. Commonly used O-protecting groups are disclosed in Greene, "Protective Groups in Organic Synthesis," 3$^{rd}$ Edition (John Wiley & Sons, New York, 1999), which is incorporated herein by reference. Exemplary O-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, pivaloyl, and the like; optionally substituted arylcarbonyl groups, such as benzoyl; silyl groups, such as trimethylsilyl (TMS), tert-butyldimethylsilyl (TBDMS), tri-iso-propylsilyloxymethyl (TOM), triisopropylsilyl (TIPS), and the like; ether-forming groups with the optionally substituted hydroxyl, such methyl, methoxymethyl, tetrahydropyranyl, benzyl, p-methoxybenzyl, trityl, and the like; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethyl hexyloxycarbonyl, cyclohexyloxycarbonyl, methyloxycarbonyl, and the like; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, 3-methyl-2-butenoxycarbonyl, and the like; haloalkoxycarbonyls, such as 2-chloroethoxycarbonyl, 2-chloroethoxycarbonyl, 2,2,2-trichloroethoxycarbonyl, and the like; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxy-carbonyl, fluorenylmethyloxycarbonyl, and the like; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, 2-chloro-4-nitrophenoxy-carbonyl, and the like); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, 1,3-dioxolane, and the like; acylal groups; and dithiane groups, such as 1,3-dithianes, 1,3-dioptionally substituted thiolane, and the like); carboxylic acid-protecting groups (e.g., ester groups, such as methyl ester, benzyl ester, t-butyl ester, orthoesters, and the like; and oxazoline groups.

The term "urea," as used herein, refers to a carbamide with two —NR$^1$R$^2$ groups joined by a carbonyl. R$_1$ and R$_2$ can be optionally substituted C$_{1-6}$ alkyl, hydrogen, or deuterium.

The term "carbamate," as used herein, refers to a chemical group of R$^1$—O—CO—NR$^2$R$^3$ wherein R$^1$, R$^2$, and R$^3$ can be any chemical group, such as optionally substituted C$_{1-6}$ alkyl.

The term "sulfonamide," as used herein, refers to a chemical group of —S(=O)$_2$—NH$_2$.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: aryl (e.g., substituted and unsubstituted phenyl), carbocyclyl (e.g., substituted and unsubstituted cycloalkyl), halogen (e.g., fluoro), hydroxyl, heteroalkyl (e.g., substituted and unsubstituted methoxy, ethoxy, or thioalkoxy), heteroaryl, heterocyclyl, amino (e.g., NH$_2$ or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Those skilled in the art will appreciate that certain compounds described herein can exist in one or more different isomeric (e.g., stereoisomers, geometric isomers, tautomers) and/or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination.

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99% or 99.9%) by weight relative to the other stereoisomers. When a single enantiomer is named or depicted by structure, the depicted or named enantiomer is at least 60%, 70%, 80%, 90%, 99% or 99.9% by weight optically pure. When a single diastereomer is named or depicted by structure, the depicted or named diastereomer is at least 60%, 70%, 80%, 90%, 99% or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99% or 99.9% by mole fraction pure relative to the other stereoisomers. When a single enantiomer is named or depicted by structure, the depicted or named enantiomer is at least 60%, 70%, 80%, 90%, 99% or 99.9% by mole fraction pure. When a single diastereomer is named or depicted by structure, the depicted or named diastereomer is at least 60%, 70%, 80%, 90%, 99% or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion, e.g., the interconversion illustrated in the scheme below:

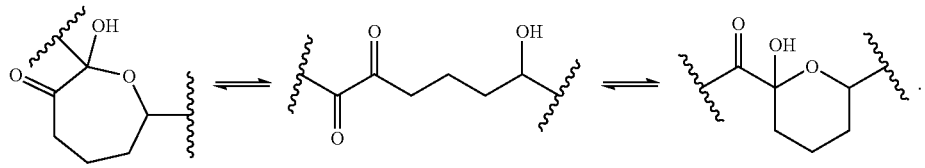 [SMILES: *C1CCCC(=O)C(*)(O)O1 ; *C(=O)C(=O)CCCC(*)O ; *C(=O)C1(O)CCCC(*)O1]

Those skilled in the art will appreciate that, in some embodiments, isotopes of compounds described herein may be prepared and/or utilized in accordance with the present invention. "Isotopes" refers to atoms having the same atomic number but different mass numbers resulting from a different number of neutrons in the nuclei. For example, isotopes of hydrogen include tritium and deuterium. In some embodiments, an isotopic substitution (e.g., substitution of hydrogen with deuterium) may alter the physiciochemical properties of the molecules, such as metabolism and/or the rate of racemization of a chiral center.

As is known in the art, many chemical entities (in particular many organic molecules and/or many small molecules) can adopt a variety of different solid forms such as, for example, amorphous forms and/or crystalline forms (e.g., polymorphs, hydrates, solvates, etc). In some embodiments, such entities may be utilized in any form, including in any solid form. In some embodiments, such entities are utilized in a particular form, for example in a particular solid form.

In some embodiments, compounds described and/or depicted herein may be provided and/or utilized in salt form.

In certain embodiments, compounds described and/or depicted herein may be provided and/or utilized in hydrate or solvate form.

At various places in the present specification, substituents of compounds of the present disclosure are disclosed in groups or in ranges. It is specifically intended that the present disclosure include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. Furthermore, where a compound includes a plurality of positions at which substitutes are disclosed in groups or in ranges, unless otherwise indicated, the present disclosure is intended to cover individual compounds and groups of compounds (e.g., genera and subgenera) containing each and every individual subcombination of members at each position.

Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional. As used herein, the term "optionally substituted X" (e.g., optionally substituted alkyl) means that X can be substituted with any substituent, e.g., any of the substituents described herein.

BRIEF DESCRIPTION OF THE DRAWINGS

FIG. 12 is a table showing data for allosteric modulation and agonist activity.

DETAILED DESCRIPTION

Figure 1:
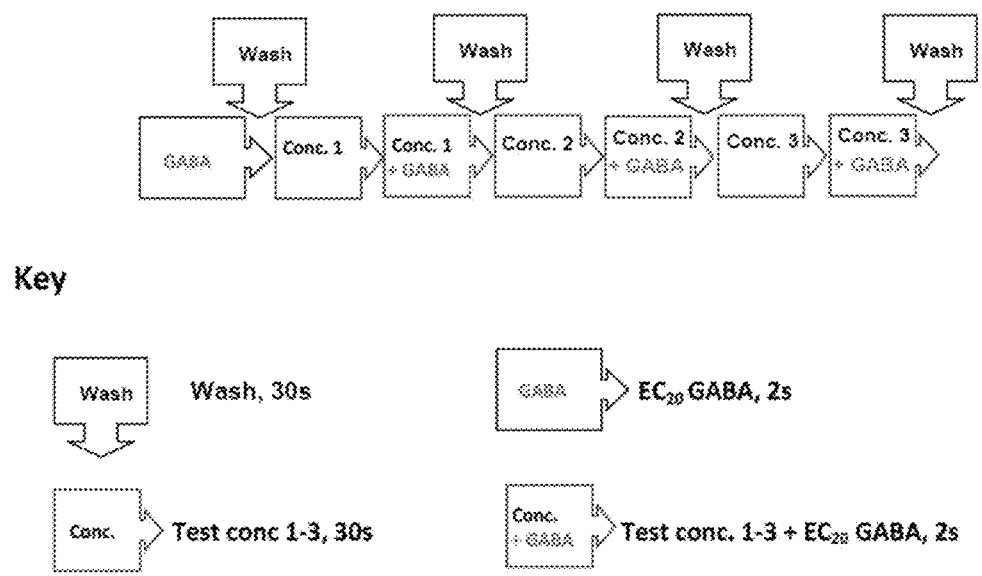
FIG. 1 shows the procedure for the GABAA IonFlux HT PAM Assay.

A range of mouse genetic models of Autism Spectrum Disorder (ASD) combined with behavioral testing, synaptic analyses, and electrophysiology were used to define both the etiology of aberrant tactile sensitivity in ASD and the contribution of somatosensory dysfunction to the expression of ASD-like traits. It was found that mutations in genes associated with both syndromic and non-syndromic forms of ASD cause tactile dysfunction, and that the Rett Syndrome (RTT)-, Phelan McDermid syndrome (PMS)-, and ASD-associated genes Mecp2, Shank3, and Gabrb3 function cell autonomously in peripheral somatosensory neurons for normal tactile behaviors. Abnormalities in tactile perception are observed in patients with Phelan McDermid Syndrome (PMS) and Fragile X syndrome, which are both highly associated with ASD and are caused by mutations in Shank3 and Fmr1, respectively. Similarly, tactile hypersensitivity is common in patients with Rett syndrome (RTT), which is caused by mutations in the X-linked methyl-CpG-binding protein 2 (Mecp2) gene. Tactile dysfunction associated with Mecp2 and Gabrb3 ASD models is caused by a deficiency of the 83 subunit of the $GABA_A$ receptor (GABRB3) and $GABA_A$ receptor-mediated presynaptic inhibition (PSI) of somatosensory inputs to the CNS. Shank3 mutant DRG neurons, which are associated with PMS, on the other hand, exhibit hyperexcitability. These somatosensory deficits during development contribute to aberrant social behaviors as well as anxiety-like behaviors in adulthood. The findings indicated that somatosensory neuron dysfunction underlies aberrant tactile perception in ASD, RTT, PMS, and Fragile X syndrome and that functional insufficiency of GABAA receptors or hyperactivity of peripheral sensory neurons cause tactile processing deficiency during development, which leads to anxiety-like behavior and social interaction deficits in adult mice. Thus, peripheral sensory neurons represent exciting, untested therapeutic targets for ASD, RTT, PMS, and Fragile X syndrome.

It has been found that deficits in peripheral sensory neurons, and not neurons in the brain, account for touch hypersensitivity in mouse models of ASD. Moreover, it has been found that touch hypersensitivity during development causes anxiety and social interaction deficits in adulthood. These findings raise the exciting possibility that $GABA_A$ receptor agonists, which attenuate the activity of peripheral mechanosensory neurons, may be useful for treating tactile hypersensitivity and thus anxiety and social impairments in ASD patients. Treating young children with $GABA_A$ receptor agonists has traditionally been avoided because of undesirable side effects of these drugs in children. Indeed, there is great reluctance on the part of physicians to use FDA-approved $GABA_A$ receptor agonists and positive allosteric modulators because of undesirable side effects, including sedation, and serious complications associated with interference with brain development. Therefore, peripherally-restricted $GABA_A$ receptor agonists, compounds that do not cross the blood-brain barrier, were used to treat tactile dysfunction and core ASD behaviors. Importantly, peripherally-restricted $GABA_A$ receptor agonists should not promote undesirable side effects observed with all currently used, FDA-approved $GABA_A$ receptor agonists that act in the brain. It has been shown that the peripherally-restricted $GABA_A$ receptor agonist, isoguvacine, improves tactile hypersensitivity, anxiety-like behaviors and social impairments in three animal models of ASD we have tested (Mecp2, Shank3, and Fmr1 mutant mice).

Accordingly, the present invention features novel peripherally-restricted $GABA_A$ receptor agonists with reduced blood brain barrier (BBB) permeability and methods of use thereof for reducing tactile dysfunction, social impairment, and/or anxiety in a subject diagnosed with ASD, RTT, PMS, or Fragile X syndrome.

Small Molecule Agents

Gamma-aminobutyrate (GABA) is synthesized primarily by the enzyme glutamate decarboxylase (GAD), which catalyzes the conversion of the excitatory neurotransmitter glutamate to GABA. GABA mediates a wide range of physiological functions, both in the CNS and in external tissues and organs, via binding to GABA receptor subtypes, $GABA_A$ and $GABA_B$. The most abundant subtype of $GABA_A$ receptors are ionotropic receptors comprised of multiple subunits that form ligand-gated chloride ion channels. The $GABA_A$ receptor subunits have been identified (alpha, beta, gamma, delta, epsilon, pi, and theta subunits), and each subunit is encoded by a separate gene. In addition, many subunits have multiple isoforms and/or splice variants, giving rise to a large degree of structural diversity.

Peripherally restricted $GABA_A$ agonists are compounds that target the $GABA_A$ receptor in the peripheral nervous system and have reduced blood brain barrier permeability. These compounds can be administered to a subject with ASD, RTT, PMS, or Fragile X syndrome to reduce tactile dysfunction, social impairment, and anxiety. Suitable compounds include $GABA_A$ agonists and positive allosteric modulators.

$GABA_A$ PAMs, such as the compounds described herein, can be modified such that they retain $GABA_A$ activity but can no longer penetrate the blood brain barrier, or such that they have reduced ability to permeate the blood brain barrier. Such compounds are "peripherally restricted," i.e., they are restricted to the peripheral nervous system. Critically, the peripherally restricted compounds disclosed herein maintain functionality as $GABA_A$ PAMs. The compounds disclosed herein have structures and physiochemical properties that maintain or improve their therapeutic activity, but limit their exposure to the CNS. In some embodiments, the compounds disclosed herein have physiochemical properties, such as Log P (water-octanol partition coefficient) values, polar surface area (PSA) and/or freely rotatable bonds (FRBs), which limit the ability of the compounds to penetrate the blood brain barrier and enter the CNS.

Peripherally restricted $GABA_A$ PAMs cannot penetrate the blood brain barrier, or have reduced blood brain barrier permeability, and target $GABA_A$ receptors in the peripheral nervous system. Such compounds can be administered to a subject with ASD, RTT, PMS, or Fragile X syndrome to reduce tactile dysfunction, social impairment, and anxiety, while avoiding unwanted central effects such as sedation.

The present disclosure provides novel small molecule agonists that modulate the $GABA_A$ receptor. A compound or pharmaceutically acceptable salt thereof of any one of Formulas I-XIII (e.g., Compounds 1-39) may be administered to a subject to reduce social impairment, anxiety, or tactile dysfunction in patients diagnosed with ASD, RTT, PMS, or Fragile X syndrome. Exemplary compounds that may be used in the compositions and methods described herein are listed in Table 1.

TABLE 1

| Compounds | |
|---|---|
| Compound | Structure |
| 1 | [structure image] |
| 2 | [structure image] |

TABLE 1-continued

Compounds

| Compound | Structure |
|---|---|
| 3 | 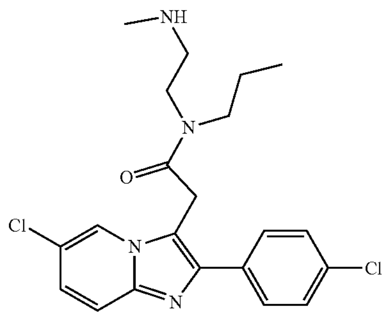 [SMILES: CCCN(CCNC)C(=O)Cc1c(-c2ccc(Cl)cc2)nc2ccc(Cl)cn12] |
| 4 | 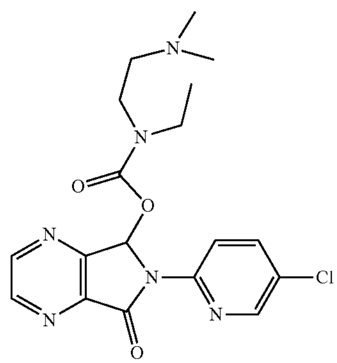 [SMILES: CCN(CCN(C)C)C(=O)OC1c2nccnc2C(=O)N1c1ccc(Cl)cn1] |
| 4a | 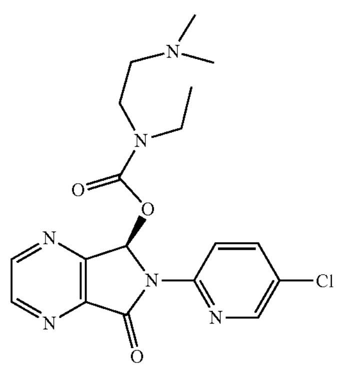 [SMILES: CCN(CCN(C)C)C(=O)O[C@@H]1c2nccnc2C(=O)N1c1ccc(Cl)cn1] |
| 4b | 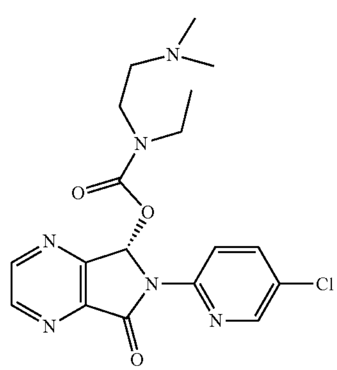 [SMILES: CCN(CCN(C)C)C(=O)O[C@H]1c2nccnc2C(=O)N1c1ccc(Cl)cn1] |
| 5 | |
| 5a | |
| 5b | |
| 6 | |

TABLE 1-continued
Compounds
| Compound | Structure |
|---|---|
| 6a | 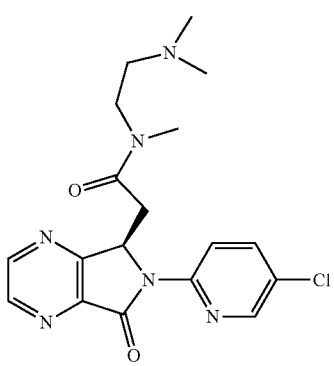 [SMILES: CN(C)CCN(C)C(=O)C[C@@H]1c2nccnc2C(=O)N1c1ccc(Cl)cn1] |
| 6b | 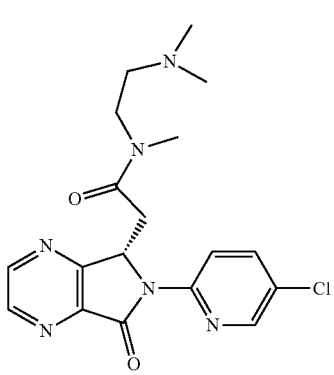 [SMILES: CN(C)CCN(C)C(=O)C[C@H]1c2nccnc2C(=O)N1c1ccc(Cl)cn1] |
| 7 | 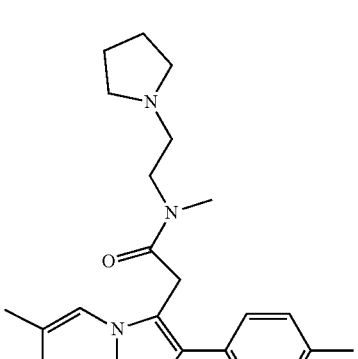 |
| 8 | 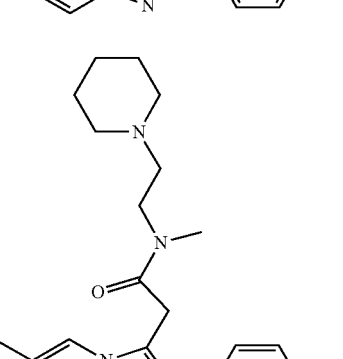 |
| 9 | 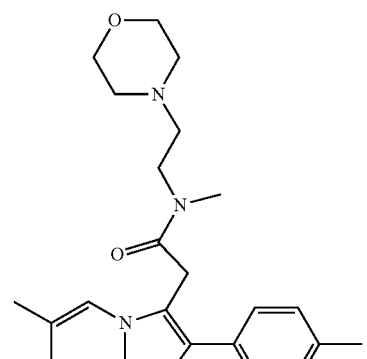 |
| 10 | 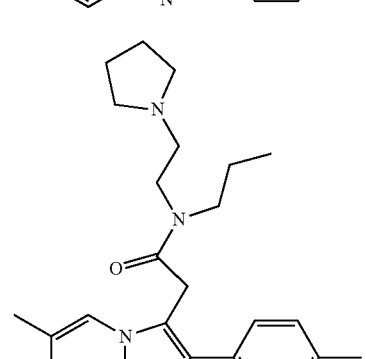 |
| 11 | 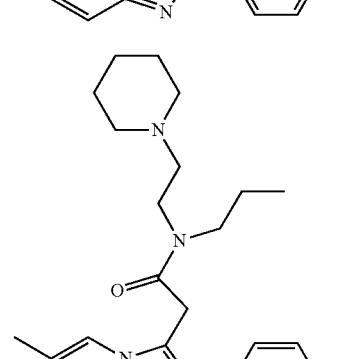 |
| 12 | 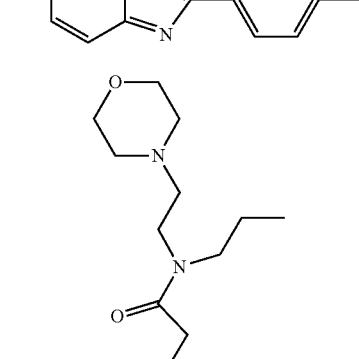 |

TABLE 1-continued

Compounds

| Compound | Structure |
|---|---|
| 13 | (structure) |
| 14 | (structure) |
| 15 | (structure) |
| 16 | (structure) |
| 17 | (structure) |
| 18 | (structure) |
| 19 | (structure) |
| 20 | (structure) |

TABLE 1-continued

| Compound | Structure |
|---|---|
| 21 | (morpholinoethyl-N-propyl amide of 6-chloro-2-(4-chlorophenyl)imidazo[1,2-a]pyridine-3-acetic acid) |
| 22 | (4-methylpiperazinyl amide of 6-chloro-2-(4-chlorophenyl)imidazo[1,2-a]pyridine-3-acetic acid) |
| 23 | (3,4-dimethylpiperazinyl amide of 6-chloro-2-(4-chlorophenyl)imidazo[1,2-a]pyridine-3-acetic acid) |
| 24 | (3,3,4-trimethylpiperazinyl amide of 6-chloro-2-(4-chlorophenyl)imidazo[1,2-a]pyridine-3-acetic acid) |
| 25 | (pyrrolidinylethyl-N-ethyl carbamate of 6-(5-chloropyridin-2-yl)-7-oxo-6,7-dihydro-5H-pyrrolo[3,4-b]pyrazin-5-ol) |
| 25a | ((S)-pyrrolidinylethyl-N-ethyl carbamate of 6-(5-chloropyridin-2-yl)-7-oxo-6,7-dihydro-5H-pyrrolo[3,4-b]pyrazin-5-ol) |
| 25b | ((R)-pyrrolidinylethyl-N-ethyl carbamate of 6-(5-chloropyridin-2-yl)-7-oxo-6,7-dihydro-5H-pyrrolo[3,4-b]pyrazin-5-ol) |

TABLE 1-continued
Compounds
| Compound | Structure |
|---|---|
| 26 | 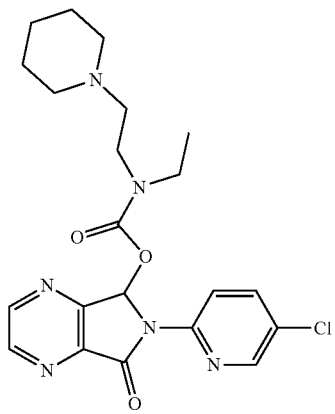 [SMILES: CCN(CCN1CCCCC1)C(=O)OC1c2nccnc2C(=O)N1c1ccc(Cl)cn1] |
| 26a | 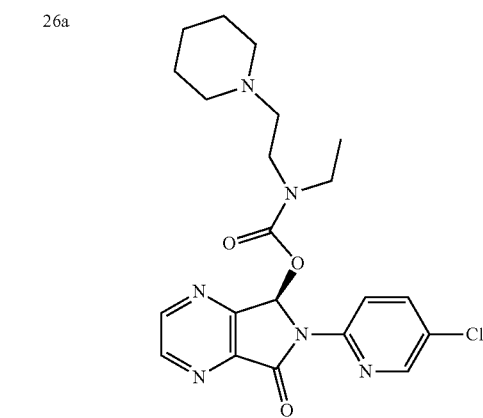 |
| 26b | 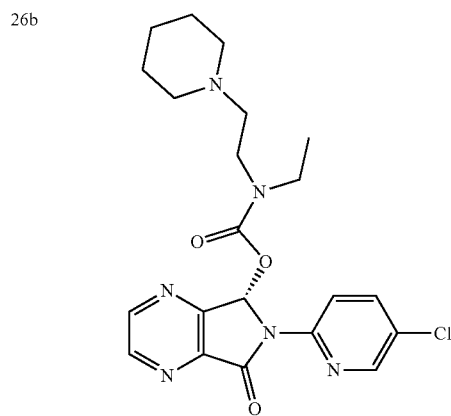 |
TABLE 1-continued
Compounds
| Compound | Structure |
|---|---|
| 27 | 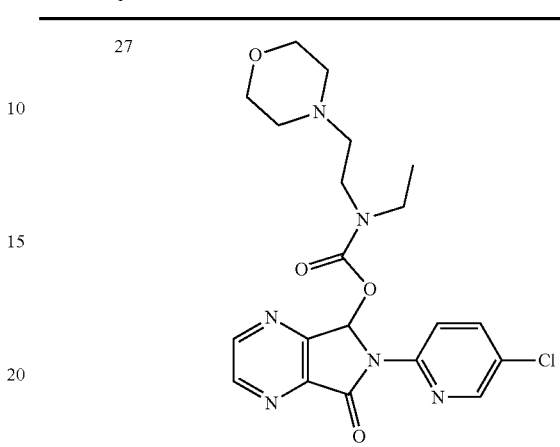 |
| 27a | 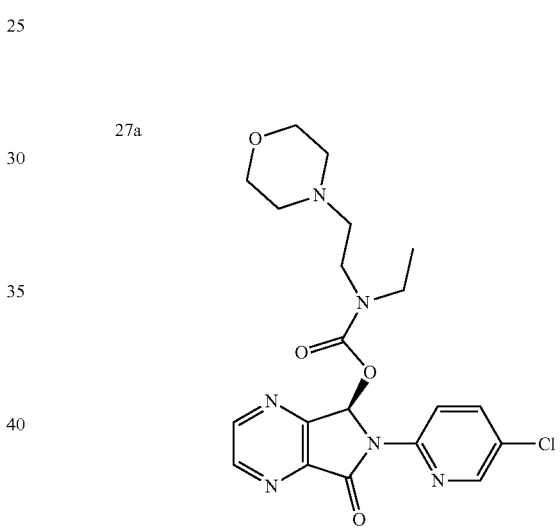 |
| 27b | 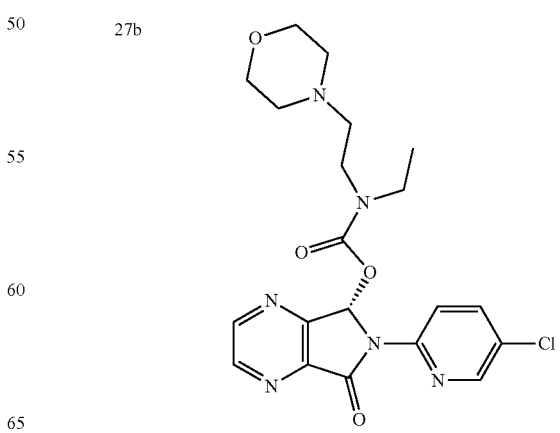 |

TABLE 1-continued
Compounds
| Compound | Structure |
|---|---|
| 28 | 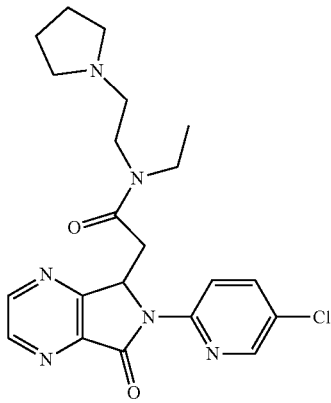 [SMILES: CCN(CCN1CCCC1)C(=O)CC1c2nccnc2C(=O)N1c1ccc(Cl)cn1] |
| 28a | 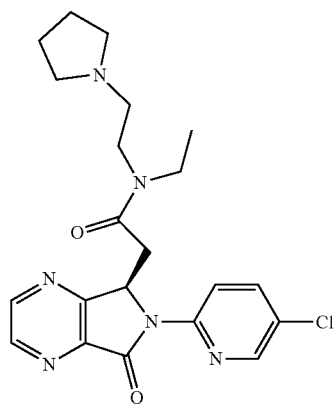 [SMILES: CCN(CCN1CCCC1)C(=O)C[C@@H]1c2nccnc2C(=O)N1c1ccc(Cl)cn1] |
| 28b | 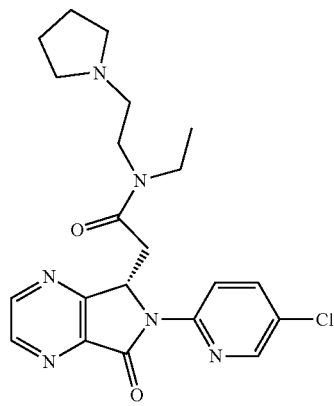 [SMILES: CCN(CCN1CCCC1)C(=O)C[C@H]1c2nccnc2C(=O)N1c1ccc(Cl)cn1] |
TABLE 1-continued
Compounds
| Compound | Structure |
|---|---|
| 29 | 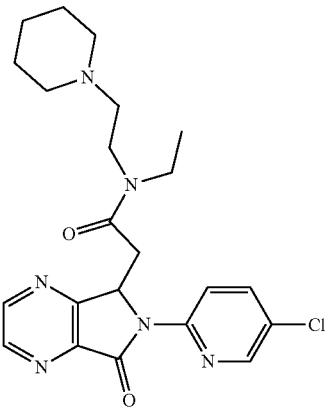 [SMILES: CCN(CCN1CCCCC1)C(=O)CC1c2nccnc2C(=O)N1c1ccc(Cl)cn1] |
| 29a | 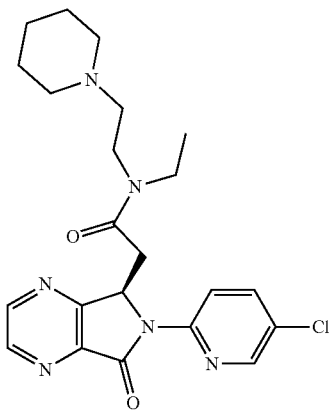 [SMILES: CCN(CCN1CCCCC1)C(=O)C[C@@H]1c2nccnc2C(=O)N1c1ccc(Cl)cn1] |
| 29b | 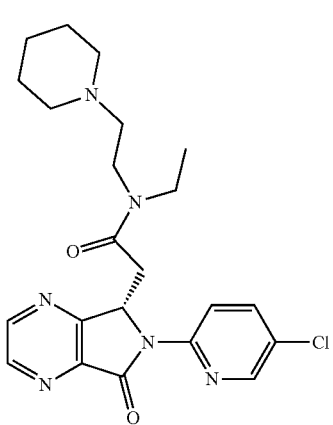 [SMILES: CCN(CCN1CCCCC1)C(=O)C[C@H]1c2nccnc2C(=O)N1c1ccc(Cl)cn1] |

TABLE 1-continued
Compounds
| Compound | Structure |
|---|---|
| 30 | 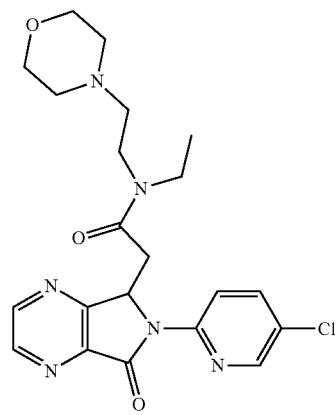 [SMILES: CCN(CCN1CCOCC1)C(=O)CC1c2nccnc2C(=O)N1c1ccc(Cl)cn1] |
| 30a | 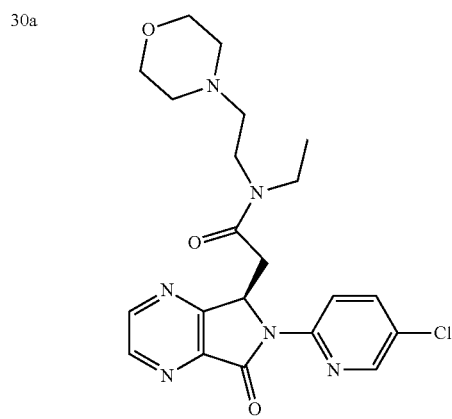 |
| 30b | 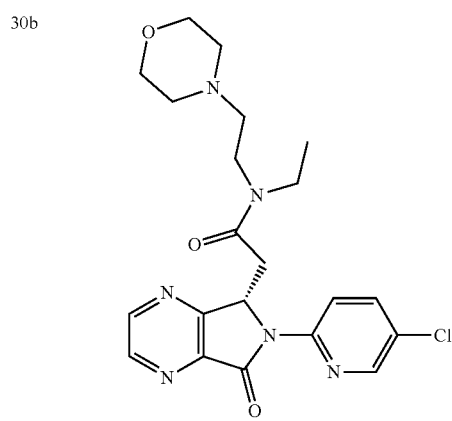 |
| 31 | 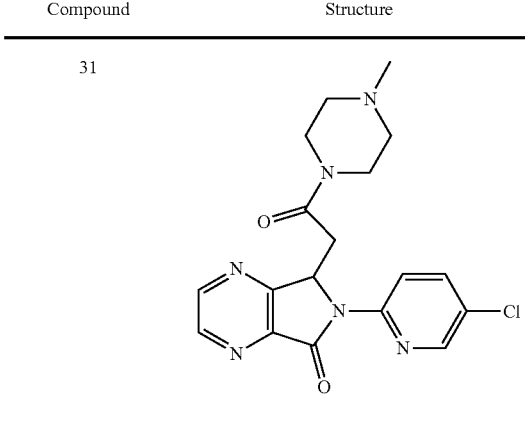 |
| 31a | 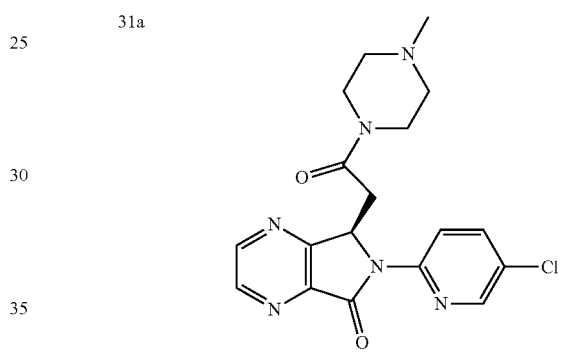 |
| 31b | 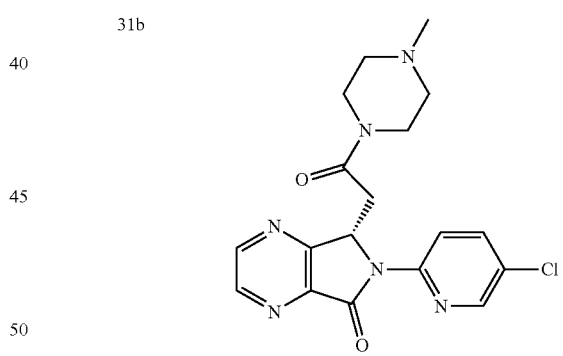 |
| 32 | 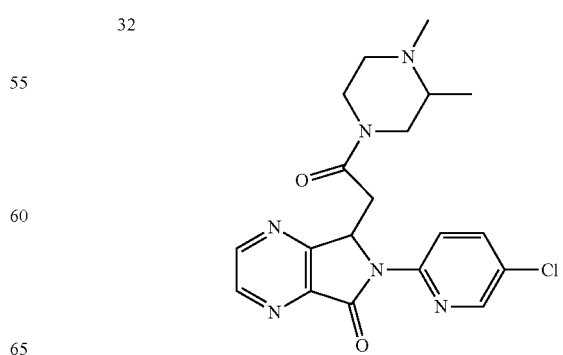 |

TABLE 1-continued

Compounds

| Compound | Structure |
|---|---|
| 32a | (chemical structure) |
| 32b | (chemical structure) |
| 33 | (chemical structure) |
| 33a | (chemical structure) |
| 33b | (chemical structure) |
| 34 | (chemical structure) |
| 35 | (chemical structure) |
| 36 | (chemical structure) |

TABLE 1-continued
| Compounds | |
|---|---|
| Compound | Structure |
| 37 | 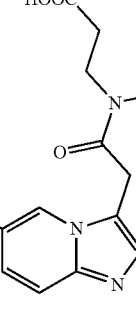 |
| 38 | 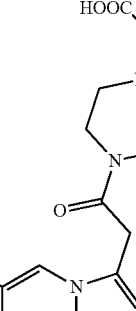 |
| 39 | 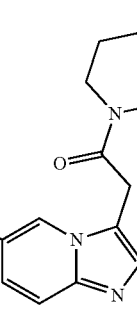 |
Provided herein are compounds of Formulae (I), (II), (IIa), (IIb), (III), (IV), (IVa), (IVb), (V), (VI), (VIa), (VIb), (VII), (VIII), (VIIIa), (VIIIb), (IX), (X), (XI), (XII), (XIII), (XIa), (XIb), (XIIa), (XIIb), (XIIIa), and (XIIIb).
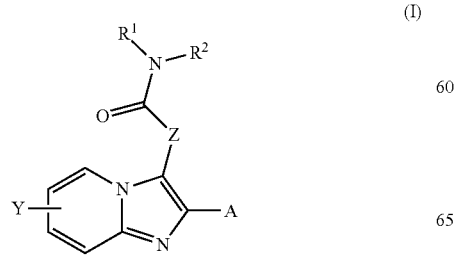
(I)
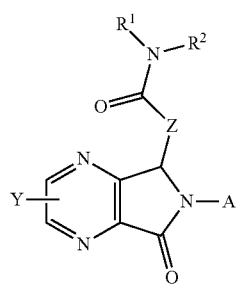
(II)
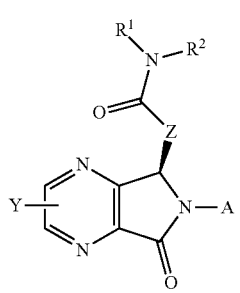
(IIa)
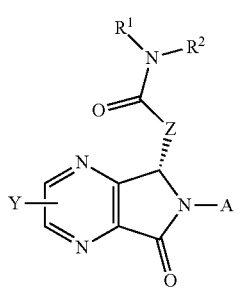
(IIb)
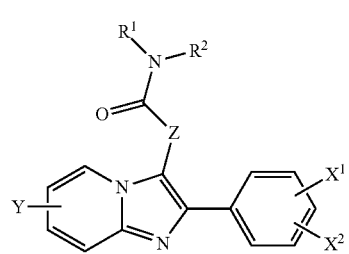
(III)
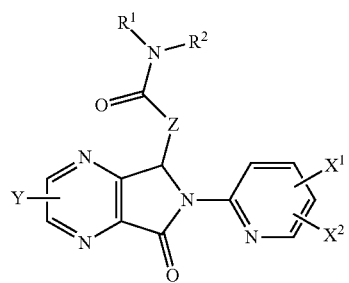
(IV)

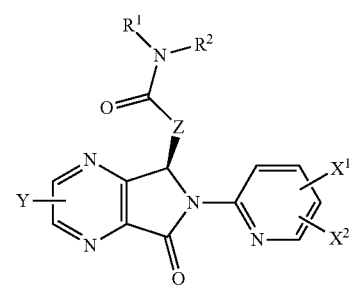
(IVa)
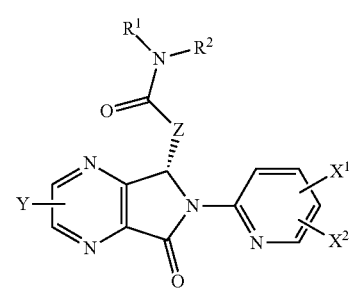
(IVb)
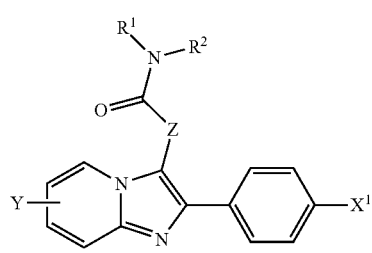
(V)
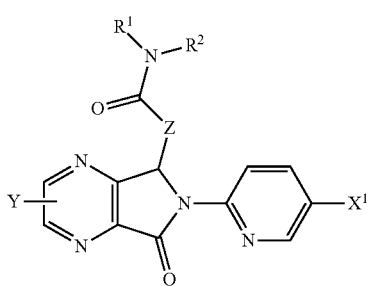
(VI)
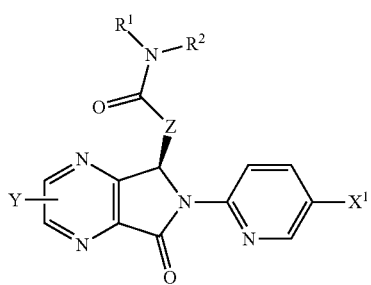
(VIa)
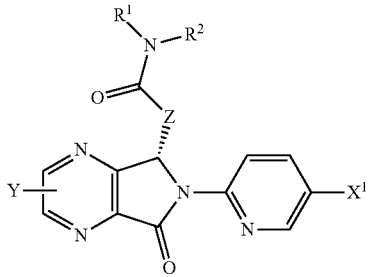
(VIb)
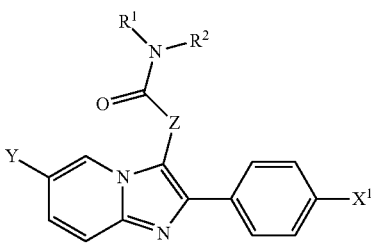
(VII)
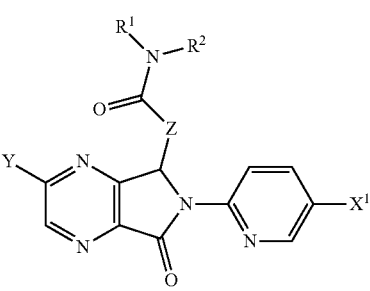
(VIII)
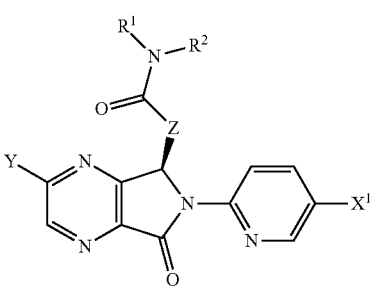
(VIIIa)
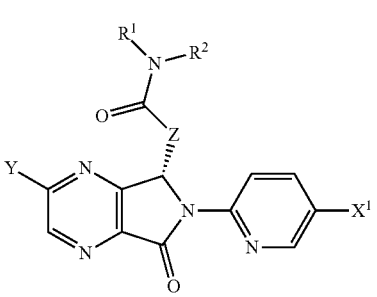
(VIIIb)
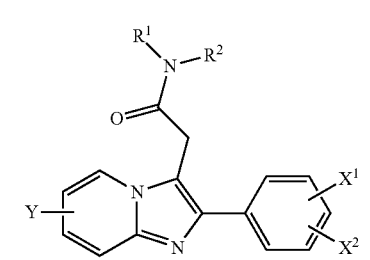
(IX)

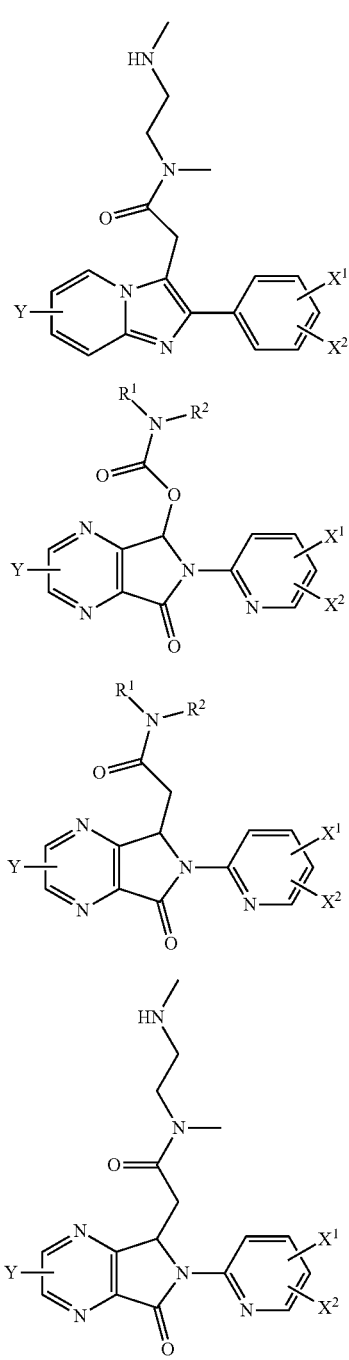

In various embodiments, Formulae (I), (II), (IIa), (IIb), (III), (IV), (IVa), (IVb), (V), (VI), (VIa), (VIb), (VII), (VIII), (VIIIa), (VIIIb), (IX), (X), (XI), (XII), (XIII), (XIa), (XIb), (XIIa), (XIIb), (XIIIa), and (XIIIb) are characterized by variable substituents being defined as follows.

Variable A

In certain embodiments, A is optionally substituted $C_{6-10}$ aryl. In certain particular embodiments, A is substituted $C_{6-10}$ aryl. In other particular embodiments, A is unsubstituted $C_{6-10}$ aryl.

Variable Y

In certain embodiments, Y is hydrogen, deuterium, halogen, or optionally substituted $C_{1-4}$ alkyl. In certain particular embodiments, Y is hydrogen. In certain particular embodiments, Y is deuterium. In certain particular embodiments, Y is halogen (e.g., fluorine, chlorine, bromine, or iodine). In certain more particular embodiments, Y is chlorine. In certain particular embodiments, Y is substituted $C_{1-4}$ alkyl (e.g., trifluoromethyl, hydroxymethyl, and the like). In certain particular embodiments, Y is unsubstituted $C_{1-4}$ alkyl (e.g., methyl, ethyl, propyl, and the like).

Variable Z

In certain embodiments, Z is oxygen, $NR^3$, or $CR^3R^4$. In certain particular embodiments, Z is oxygen. In certain particular embodiments, Z is $NR^3$. In a more particular embodiment. Z is NH or N($C_{1-6}$alkyl)). In certain particular embodiments, Z is $CR^3R^4$. In a more particular embodiment, Z is $CH_2$.

Variable $R^1$

In certain embodiments, $R^1$ is optionally substituted alkylcarboxylic acid, optionally substituted alkylcarboxylic acid ester, optionally substituted alkylcarboxylic acid amide, optionally substituted $C_{1-6}$ alkylamino, optionally substituted heteroalkyl, or optionally substituted $C_{1-6}$ alkyl with at least one $C_{3-7}$ heterocycle comprising 1-3 nitrogen atoms, 1-2 oxygen atoms, or combinations thereof. In certain particular embodiments, $R^1$ is substituted alkylcarboxylic acid. In certain particular embodiments, $R^1$ is unsubstituted alkylcarboxylic acid. In certain particular embodiments, $R^1$ is substituted alkylcarboxylic acid ester. In certain particular embodiments, $R^1$ is unsubstituted alkylcarboxylic acid ester. In certain particular embodiments, $R^1$ is substituted alkylcarboxylic acid amide. In certain particular embodiments, $R^1$ is unsubstituted alkylcarboxylic acid amide. In certain particular embodiments, $R^1$ is substituted heteroalkyl. In certain particular embodiments, $R^1$ is unsubstituted heteroalkyl. In certain particular embodiments, $R^1$ is substituted $C_{1-6}$ alkylamino. In certain particular embodiments, $R^1$ is unsubstituted $C_{1-6}$ alkylamino. In certain embodiments, $R^1$ is $C_{1-6}$ alkyl substituted with at least one $C_{3-7}$ heterocycle comprising 1-3 nitrogen atoms, 1-2 oxygen atoms, or combinations thereof. Representative $C_{3-7}$ heterocycles include oxiranyl, aziridinyl, oxetanyl, azetidinyl, tetrahydrofuranyl pyrrolidinyl, pyranyl, piperidinyl, morpholinyl, piperazinyl, and diazepinyl.

Variable $R^2$

In certain embodiments, $R^2$ is optionally substituted $C_{1-6}$ alkyl or optionally substituted $C_{3-6}$ cycloalkyl. In certain particular embodiments, $R^2$ is substituted $C_{1-6}$ alkyl. In certain particular embodiments, $R^2$ is unsubstituted $C_{1-6}$ alkyl. In certain particular embodiments, $R^1$ is substituted heteroalkyl. In certain particular embodiments, $R^1$ is unsubstituted heteroalkyl. In certain particular embodiments, $R^2$ is substituted $C_{3-6}$ cycloalkyl. In certain particular embodiments, $R^2$ is unsubstituted $C_{3-6}$ cycloalkyl. Representative $C_{3-6}$ cycloalkyls include cyclopropyl, cyclobutyl, cyclopentyl and cyclohexyl.

Variables $R^1$ and $R^2$

In certain embodiments, $R^1$ and $R^2$ combine to form an optionally substituted $C_{3-6}$ cycloalkyl or optionally substituted $C_{3-6}$ heterocycle. In certain particular embodiments, $R^1$ and $R^2$ combine to form a substituted $C_{3-6}$ cycloalkyl. In certain particular embodiments, $R^1$ and $R^2$ combine to form an unsubstituted $C_{3-6}$ cycloalkyl. Representative $C_{3-6}$ cycloalkyls include cyclopropyl, cyclobutyl, cyclopentyl and cyclohexyl. In certain particular embodiments, $R^1$ and $R^2$ combine to form a substituted $C_{3-6}$ heterocycle. In certain particular embodiments, $R^1$ and $R^2$ combine to form an unsubstituted $C_{3-6}$ heterocycle. Representative $C_{3-6}$ heterocycles include oxiranyl, aziridinyl, oxetanyl, azetidinyl, tetrahydrofuranyl pyrrolidinyl, pyranyl, piperidinyl, morpholinyl, and piperazinyl.

Variable $R^3$

In certain embodiments, $R^3$ is hydrogen, deuterium, or optionally substituted $C_{1-6}$ alkyl. In certain particular embodiments, $R^3$ is hydrogen. In certain particular embodiments, $R^3$ is deuterium. In certain particular embodiments, $R^3$ is substituted $C_{1-6}$ alkyl. In certain particular embodiments, $R^3$ is unsubstituted $C_{1-6}$ alkyl.

Variable $R^4$

In certain embodiments, $R^4$ is hydrogen, deuterium, or optionally substituted $C_{1-6}$ alkyl. In certain particular embodiments, $R^4$ is hydrogen. In certain particular embodiments, $R^4$ is deuterium. In certain particular embodiments, $R^4$ is substituted $C_{1-6}$ alkyl. In certain particular embodiments, $R^4$ is unsubstituted $C_{1-6}$ alkyl.

Variable $R^5$

In certain embodiments, $R^5$ is hydrogen, deuterium, optionally substituted $C_{1-6}$ alkyl, optionally substituted $C_{3-6}$ cycloalkyl, acyl, carbamate, sulfonamide, or urea. In certain particular embodiments, $R^5$ is hydrogen. In certain particular embodiments, $R^5$ is deuterium. In certain particular embodiments, $R^5$ is substituted $C_{1-6}$ alkyl. In certain particular embodiments, $R^5$ is unsubstituted $C_{1-6}$ alkyl. In certain particular embodiments, $R^5$ is substituted $C_{3-6}$ cycloalkyl. In certain particular embodiments, $R^5$ is unsubstituted $C_{3-6}$ cycloalkyl. In certain particular embodiments, $R^5$ is acyl. Representative acyl groups include acetyl, propionyl, butryl, benzoyl, and the like. In certain particular embodiments, $R^5$ is carbamate. In certain particular embodiments, $R^5$ is sulfonamide. In certain particular embodiments, $R^5$ is urea.

Variable $R^6$

In certain embodiments, $R^6$ is hydrogen, deuterium, optionally substituted $C_{1-6}$ alkyl, optionally substituted $C_{3-6}$ cycloalkyl, acyl, carbamate, sulfonamide, or urea. In certain particular embodiments, $R^6$ is hydrogen. In certain particular embodiments, $R^6$ is deuterium. In certain particular embodiments, $R^6$ is substituted $C_{1-6}$ alkyl. In certain particular embodiments, $R^6$ is unsubstituted $C_{1-6}$ alkyl. In certain particular embodiments, $R^6$ is substituted $C_{3-6}$ cycloalkyl. In certain particular embodiments, $R^6$ is unsubstituted $C_{3-6}$ cycloalkyl. In certain particular embodiments, $R^6$ is acyl. Representative acyl groups include acetyl, propionyl, butryl, benzoyl, and the like. In certain particular embodiments, $R^6$ is carbamate. In certain particular embodiments, $R^6$ is sulfonamide. In certain particular embodiments, $R^6$ is urea.

Variable $X^1$

In certain embodiments, $X^1$ is hydrogen, deuterium, halogen, $C_{1-4}$ alkoxy, $C_{1-6}$ alkyl, $CF_3$, $NR^5R^6$, $CH_3S$, $CH_3SO_2$, or $NO_2$. In certain particular embodiments, $X^1$ is hydrogen. In certain particular embodiments, $X^1$ is deuterium. In certain particular embodiments, $X^1$ is halogen (e.g., fluorine, bromine, chlorine, and iodine). In more particular embodiments, $X^1$ is chlorine. In certain particular embodiments, $X^1$ is substituted $C_{1-4}$ alkoxy. In certain particular embodiments, $X^1$ is unsubstituted $C_{1-4}$ alkoxy. In certain particular embodiments, $X^1$ is substituted $C_{1-6}$ alkyl. In more particular embodiments, $X^1$ is $CF_3$. In certain particular embodiments, $X^1$ is unsubstituted $C_{1-6}$ alkyl. In certain particular embodiments, $X^1$ is $NR^5R^6$. In certain particular embodiments, $X^1$ is $NO_2$. In certain particular embodiments, $X^1$ is $CH_3SO_2$. In certain particular embodiments, $X^1$ is $CH_3S$.

Variable $X^2$

In certain embodiments, $X^2$ is hydrogen, deuterium, halogen, $C_{1-4}$ alkoxy, $C_{1-6}$ alkyl, $CF_3$, $NR^5R^6$, or $NO_2$. In certain particular embodiments, $X^2$ is hydrogen. In certain particular embodiments, $X^2$ is deuterium. In certain particular embodiments, $X^2$ is halogen (e.g., fluorine, bromine, chlorine, and iodine). In more particular embodiments, $X^2$ is chlorine. In certain particular embodiments, $X^2$ is substituted $C_{1-4}$ alkoxy. In certain particular embodiments, $X^2$ is unsubstituted $C_{1-4}$ alkoxy. In certain particular embodiments, $X^2$ is substituted $C_{1-6}$ alkyl. In more particular embodiments, $X^2$ is $CF_3$. In certain particular embodiments, $X^2$ is unsubstituted $C_{1-6}$ alkyl. In certain particular embodiments, $X^2$ is $NR^5R^6$. In certain particular embodiments, $X^2$ is $NO_2$.

Compounds that may be used in the compositions and methods described herein include any compound having the structure of Formula (I) or Formula (II):

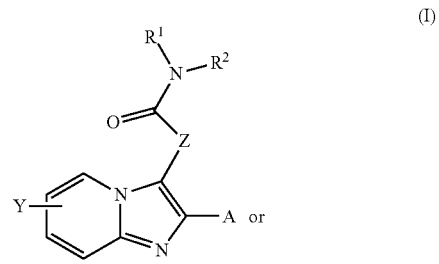

(I)

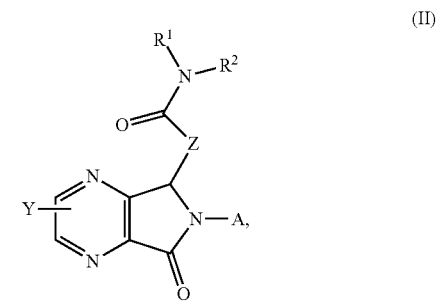

(II)

wherein

A is optionally substituted $C_{6-10}$ aryl;

Y is hydrogen, deuterium, halogen, or optionally substituted $C_{1-4}$ alkyl;

Z is oxygen, $NR^3$, or $CR^3R^4$;

$R^1$ is optionally substituted $C_{1-6}$ alkylamino, or optionally substituted $C_{1-6}$ alkyl with at least one $C_{3-7}$ heterocycle comprising 1-3 nitrogen atoms, 1-2 oxygen atoms, or combinations thereof;

$R^2$ is optionally substituted $C_{1-6}$ alkyl or optionally substituted $C_{3-6}$ cycloalkyl;

or $R^1$ and $R^2$ together form an optionally substituted $C_{3-6}$ cycloalkyl or optionally substituted $C_{3-6}$ heterocycle; and each of $R^3$ and $R^4$ is, independently, hydrogen, deuterium, or optionally substituted $C_{1-6}$ alkyl; or a pharmaceutically acceptable salt thereof.

In some embodiments, the compounds that may be used in the compositions and methods described herein include any compound having the structure of Formula (IIa) or Formula (IIb):

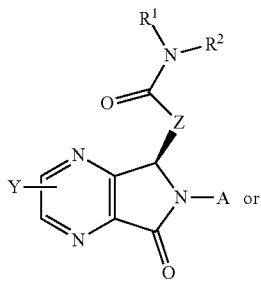

(IIa)

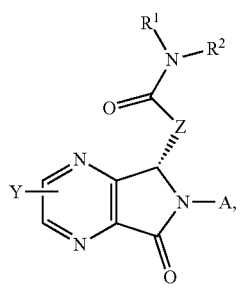

(IIb)

wherein
  A is optionally substituted $C_{6-10}$ aryl;
  Y is hydrogen, deuterium, halogen, or optionally substituted $C_{1-4}$ alkyl;
  Z is oxygen, $NR^3$, or $CR^3R^4$;
  $R^1$ is optionally substituted $C_{1-6}$ alkylamino, or optionally substituted $C_{1-6}$ alkyl with at least one $C_{3-7}$ heterocycle comprising 1-3 nitrogen atoms, 1-2 oxygen atoms, or combinations thereof;
  $R^2$ is optionally substituted $C_{1-6}$ alkyl or optionally substituted $C_{3-6}$ cycloalkyl;
  or $R^1$ and $R^2$ together form an optionally substituted $C_{3-6}$ cycloalkyl or optionally substituted $C_{3-6}$ heterocycle; and
  each of $R^3$ and $R^4$ is, independently, hydrogen, deuterium, or optionally substituted $C_{1-6}$ alkyl; or a pharmaceutically acceptable salt thereof.

In some embodiments, the compounds that may be used in the compositions and methods described herein include any compound having the structure of Formula (III) or Formula (IV):

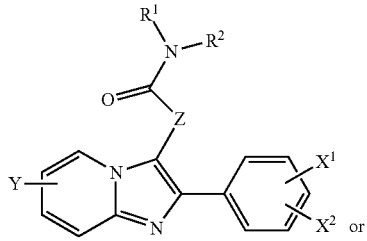

(III)

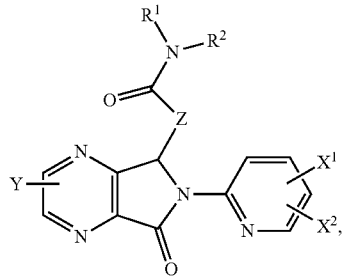

(IV)

wherein
  each of $X^1$ and $X^2$ is, independently, hydrogen, deuterium, halogen, $C_{1-4}$ alkoxy, $C_{1-6}$ alkyl, $CF_3$, $NR^5R^6$, or $NO_2$;
  Y is hydrogen, deuterium, halogen, or optionally substituted $C_{1-4}$ alkyl;
  Z is oxygen, $NR^3$, or $CR^3R^4$;
  $R^1$ is optionally substituted $C_{1-6}$ alkylamino, or optionally substituted $C_{1-6}$ alkyl with at least one $C_{3-7}$ heterocycle comprising 1-3 nitrogen atoms, 1-2 oxygen atoms, or combinations thereof;
  $R^2$ is optionally substituted $C_{1-6}$ alkyl or optionally substituted $C_{3-6}$ cycloalkyl;
  or $R^1$ and $R^2$ together form an optionally substituted $C_{3-6}$ cycloalkyl or optionally substituted $C_{3-6}$ heterocycle;
  each of $R^3$ and $R^4$ is, independently, hydrogen, deuterium, or optionally substituted $C_{1-6}$ alkyl; and
  each of $R^5$ and $R^6$ is, independently, hydrogen, deuterium, optionally substituted $C_{1-6}$ alkyl, optionally substituted $C_{3-6}$ cycloalkyl, acyl, carbamate, sulfonamide, or urea;
or a pharmaceutically acceptable salt thereof.

In some embodiments, the compounds that may be used in the compositions and methods described herein include any compound having the structure of Formula (IVa) or Formula (IVb):

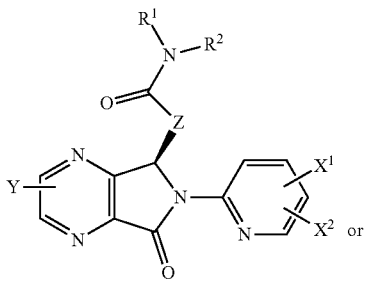

(IVa)

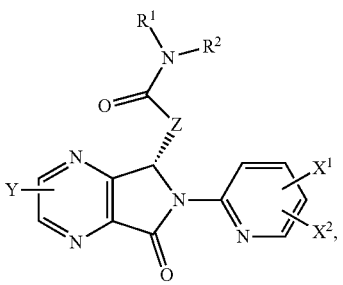

(IVb)

wherein
  each of $X^1$ and $X^2$ is, independently, hydrogen, deuterium, halogen, $C_{1-4}$ alkoxy, $C_{1-6}$ alkyl, $CF_3$, $NR^5R^6$, or $NO_2$;

Y is hydrogen, deuterium, halogen, or optionally substituted $C_{1-4}$ alkyl;

Z is oxygen, $NR^3$, or $CR^3R^4$;

$R^1$ is optionally substituted $C_{1-6}$ alkylamino, or optionally substituted $C_{1-6}$ alkyl with at least one $C_{3-7}$ heterocycle comprising 1-3 nitrogen atoms, 1-2 oxygen atoms, or combinations thereof;

$R^2$ is optionally substituted $C_{1-6}$ alkyl or optionally substituted $C_{3-6}$ cycloalkyl;

or $R^1$ and $R^2$ together form an optionally substituted $C_{3-6}$ cycloalkyl or optionally substituted $C_{3-6}$ heterocycle;

each of $R^3$ and $R^4$ is, independently, hydrogen, deuterium, or optionally substituted $C_{1-6}$ alkyl; and each of $R^5$ and $R^6$ is, independently, hydrogen, deuterium, optionally substituted $C_{1-6}$ alkyl, optionally substituted $C_{3-6}$ cycloalkyl, acyl, carbamate, sulfonamide, or urea;

or a pharmaceutically acceptable salt thereof.

In some embodiments, the compounds that may be used in the compositions and methods described herein include any compound having the structure of Formula (V) or Formula (VI):

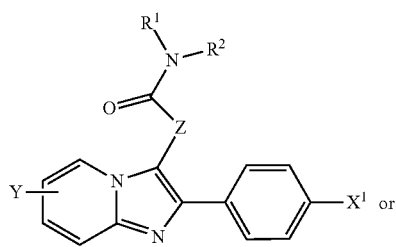

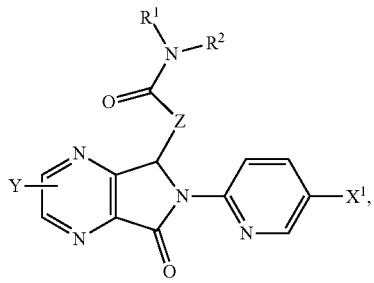

wherein $X^1$ is hydrogen, deuterium, halogen, $C_{1-4}$ alkoxy, $C_{1-6}$ alkyl, $CF_3$, $CH_3S$, $CH_3SO_2$, or $NO_2$;

Y is hydrogen, deuterium, halogen, or $C_{1-4}$ alkyl;

Z is oxygen, $NR^3$, or $CR^3R^4$;

$R^1$ is optionally substituted amino, optionally substituted $C_{1-6}$ alkylamino, or optionally substituted $C_{1-6}$ alkyl with at least one $C_{3-7}$ heterocycle comprising 1-3 nitrogen atoms, 1-2 oxygen atoms, or combinations thereof;

$R^2$ is optionally substituted $C_{1-6}$ alkyl;

or $R^1$ and $R^2$ together form an optionally substituted $C_{3-6}$ cycloalkyl or optionally substituted $C_{3-6}$ heterocycle; and each of $R^3$ and $R^4$ is, independently, hydrogen, deuterium, or optionally substituted $C_{1-6}$ alkyl; or a pharmaceutically acceptable salt thereof.

In some embodiments, the compounds that may be used in the compositions and methods described herein include any compound having the structure of Formula (VIa) or Formula (VIb):

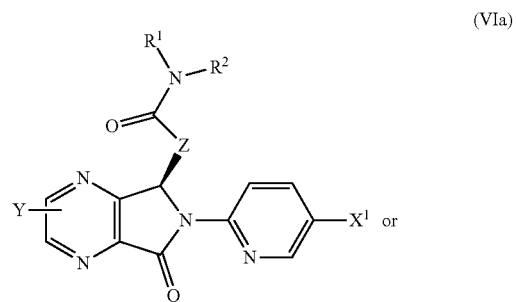

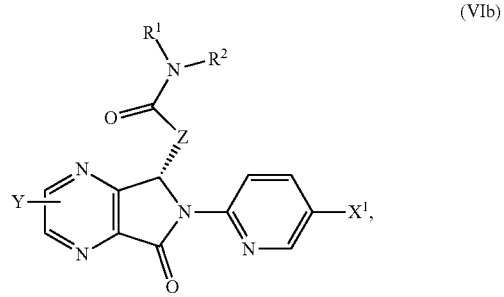

wherein $X^1$ is hydrogen, deuterium, halogen, $C_{1-4}$ alkoxy, $C_{1-6}$ alkyl, $CF_3$, $CH_3S$, $CH_3SO_2$, or $NO_2$;

Y is hydrogen, deuterium, halogen, or $C_{1-4}$ alkyl;

Z is oxygen, $NR^3$, or $CR^3R^4$;

$R^1$ is optionally substituted amino, optionally substituted $C_{1-6}$ alkylamino, or optionally substituted $C_{1-6}$ alkyl with at least one $C_{3-7}$ heterocycle comprising 1-3 nitrogen atoms, 1-2 oxygen atoms, or combinations thereof;

$R^2$ is optionally substituted $C_{1-6}$ alkyl;

or $R^1$ and $R^2$ together form an optionally substituted $C_{3-6}$ cycloalkyl or optionally substituted $C_{3-6}$ heterocycle; and each of $R^3$ and $R^4$ is, independently, hydrogen, deuterium, or optionally substituted $C_{1-6}$ alkyl; or a pharmaceutically acceptable salt thereof.

In some embodiments, the compounds that may be used in the compositions and methods described herein include any compound having the structure of Formula (VII) or Formula (VIII):

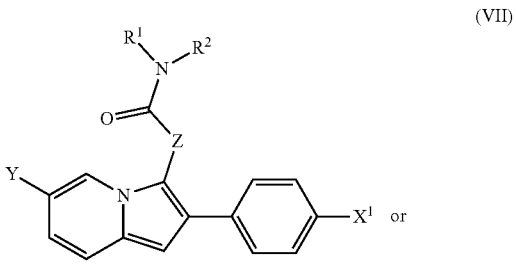

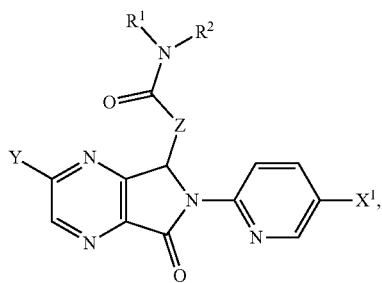
(VIII)

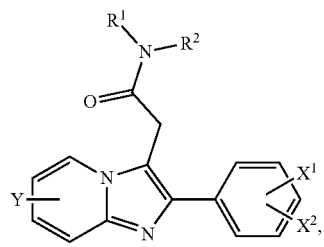
(IX)

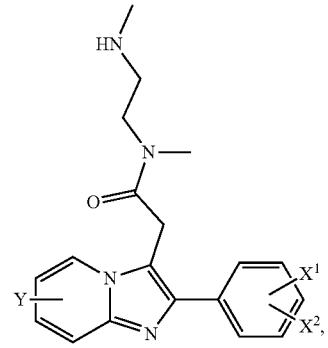
(X)

wherein
- X¹ is hydrogen, deuterium, halogen, $C_{1-4}$ alkoxy, $C_{1-6}$ alkyl, $CF_3$, $CH_3S$, $CH_3SO_2$, or $NO_2$;
- Y is hydrogen, deuterium, halogen, or $C_{1-4}$ alkyl;
- Z is oxygen, NH, or $CH_2$;
- R¹ is optionally substituted $C_{1-6}$ alkylamino; and
- R² is optionally substituted $C_{1-6}$ alkyl;

or a pharmaceutically acceptable salt thereof.

In some embodiments, the compounds that may be used in the compositions and methods described herein include any compound having the structure of Formula (VIIIa) or Formula (VIIIb):

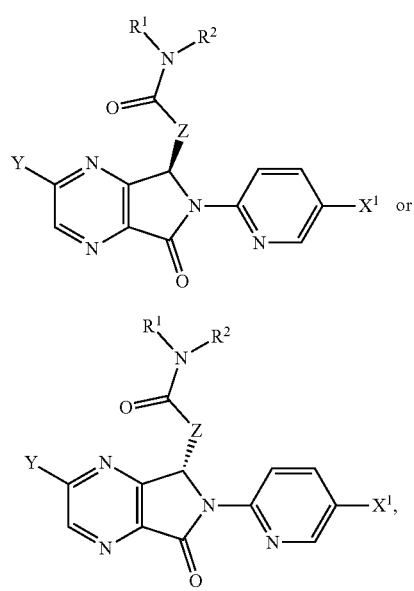
(VIIIa)

(VIIIb)

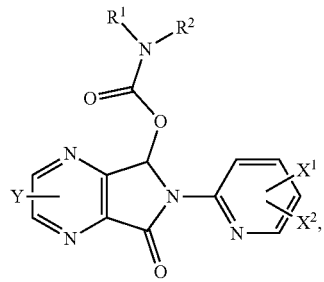
(XI)

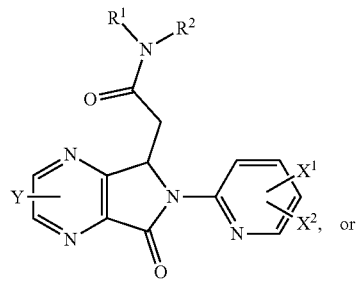
(XII)

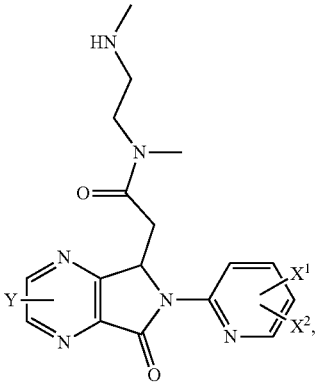
(XIII)

wherein
- X¹ is hydrogen, deuterium, halogen, $C_{1-4}$ alkoxy, $C_{1-6}$ alkyl, $CF_3$, $CH_3S$, $CH_3SO_2$, or $NO_2$;
- Y is hydrogen, deuterium, halogen, or $C_{1-4}$ alkyl;
- Z is oxygen, NH, or $CH_2$;
- R¹ is optionally substituted $C_{1-6}$ alkylamino; and
- R² is optionally substituted $C_{1-6}$ alkyl;

or a pharmaceutically acceptable salt thereof.

In some embodiments, the compounds that may be used in the compositions and methods described herein include any compound having the structure of any one of Formulas (IX)-(XIII):

wherein
each of X¹ and X² is, independently, hydrogen, deuterium, halogen, $C_{1-4}$ alkoxy, $C_{1-6}$ alkyl, $CF_3$, $NR^5R^6$, or $NO_2$;

Y is hydrogen, deuterium, halogen, or optionally substituted $C_{1-4}$ alkyl;

Z is oxygen, $NR^3$, or $CR^3R^4$;

$R^1$ is optionally substituted $C_{1-6}$ alkylamino, or optionally substituted $C_{1-6}$ alkyl with at least one $C_{3-7}$ heterocycle comprising 1-3 nitrogen atoms, 1-2 oxygen atoms, or combinations thereof;

$R^2$ is optionally substituted $C_{1-6}$ alkyl or optionally substituted $C_{3-6}$ cycloalkyl;

or $R^1$ and $R^2$ together form an optionally substituted $C_{3-6}$ cycloalkyl or optionally substituted $C_{3-6}$ heterocycle;

each of $R^3$ and $R^4$ is, independently, hydrogen, deuterium, or optionally substituted $C_{1-6}$ alkyl; and each of $R^5$ and $R^6$ is, independently, hydrogen, deuterium, optionally substituted $C_{1-6}$ alkyl, optionally substituted $C_{3-6}$ cycloalkyl, acyl, carbamate, sulfonamide, or urea;

or a pharmaceutically acceptable salt thereof.

In some embodiments, the compounds that may be used in the compositions and methods described herein include any compound having the structure of Formula (XIa), Formula (XIb), Formula (XIIa), Formula (XIIb), Formula (XIIIa), or Formula (XIIIb):

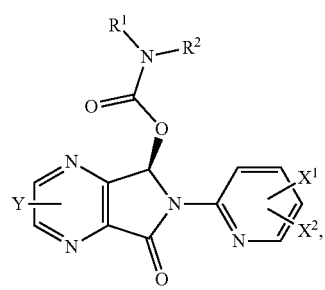

(XIa)

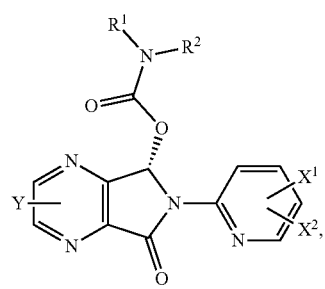

(XIb)

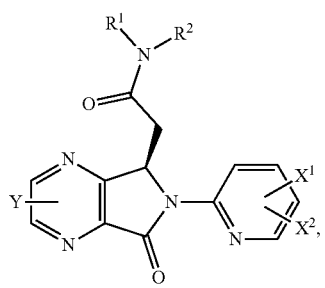

(XIIa)

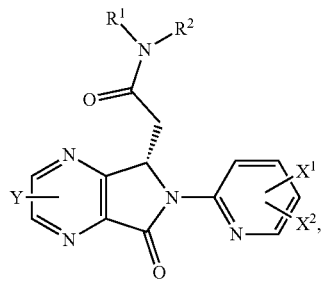

(XIIb)

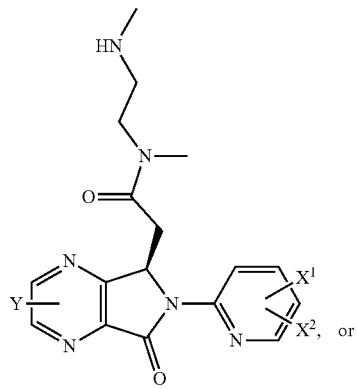

(XIIIa), or

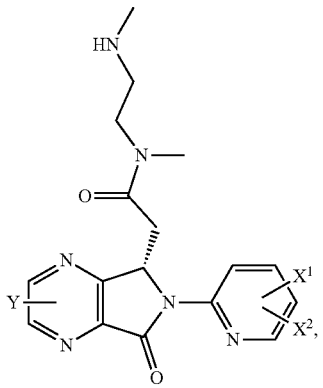

(XIIIb)

wherein
each of $X^1$ and $X^2$ is, independently, hydrogen, deuterium, halogen, $C_{1-4}$ alkoxy, $C_{1-6}$ alkyl, $CF_3$, $NR^5R^6$, or $NO_2$;

Y is hydrogen, deuterium, halogen, or optionally substituted $C_{1-4}$ alkyl;

Z is oxygen, $NR^3$, or $CR^3R^4$;

$R^1$ is optionally substituted $C_{1-6}$ alkylamino, or optionally substituted $C_{1-6}$ alkyl with at least one $C_{3-7}$ heterocycle comprising 1-3 nitrogen atoms, 1-2 oxygen atoms, or combinations thereof;

$R^2$ is optionally substituted $C_{1-6}$ alkyl or optionally substituted $C_{3-6}$ cycloalkyl;

or $R^1$ and $R^2$ together form an optionally substituted $C_{3-6}$ cycloalkyl or optionally substituted $C_{3-6}$ heterocycle;

each of $R^3$ and $R^4$ is, independently, hydrogen, deuterium, or optionally substituted $C_{1-6}$ alkyl; and each of $R^5$ and $R^6$ is, independently, hydrogen, deuterium, optionally substituted $C_{1-6}$ alkyl, optionally substituted $C_{3-6}$ cycloalkyl, acyl, carbamate, sulfonamide, or urea;

or a pharmaceutically acceptable salt thereof.

In some embodiments of any of the compounds described herein, an oxygen (e.g., oxygen in a carboxylic acid) has an O-protecting group. An 0-protecting group is intended to protect an oxygen containing (e.g., phenol, optionally substituted hydroxyl, or carbonyl) group against undesirable reactions during synthetic procedures. Commonly used 0-protecting groups are disclosed in Greene, "Protective Groups in Organic Synthesis," $3^{rd}$ Edition (John Wiley & Sons, New York, 1999), which is incorporated herein by reference. Exemplary 0-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, pivaloyl, and the like; optionally substituted arylcarbonyl groups, such as benzoyl; silyl groups, such as trimethylsilyl (TMS), tert-butyldimethylsilyl (TBDMS), tri-iso-propylsilyloxymethyl (TOM), triisopropylsilyl (TIPS), and the like; ether-forming groups with the optionally substituted hydroxyl, such methyl, methoxymethyl, tetrahydropyranyl, benzyl, p-methoxybenzyl, trityl, and the like; alkoxycarbonyls, such as methoxycarbonyl, ethoxycarbonyl, iso-propoxycarbonyl, n-isopropoxycarbonyl, n-butyloxycarbonyl, isobutyloxycarbonyl, sec-butyloxycarbonyl, t-butyloxycarbonyl, 2-ethyl hexyloxycarbonyl, cyclohexyloxycarbonyl, methyloxycarbonyl, and the like; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, 3-methyl-2-butenoxycarbonyl, and the like; haloalkoxycarbonyls, such as 2-chloroethoxycarbonyl, 2-chloroethoxycarbonyl, 2,2,2-trichloroethoxycarbonyl, and the like; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxy-carbonyl, fluorenylmethyloxycarbonyl, and the like; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, 2-chloro-4-nitrophenoxy-carbonyl, and the like); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, 1,3-dioxolane, and the like; acylal groups; and dithiane groups, such as 1,3-dithianes, 1,3-dioptionally substituted thiolane, and the like); carboxylic acid-protecting groups (e.g., ester groups, such as methyl ester, benzyl ester, t-butyl ester, orthoesters, and the like; and oxazoline groups.

In some embodiments of any of any of the compounds described herein, a nitrogen (e.g., nitrogen in the amino moiety) has an N-protecting group. An N-protecting group is intended to protect an amino group against undesirable reactions during synthetic procedures. Commonly used N-protecting groups are disclosed in Greene, "Protective Groups in Organic Synthesis," $3^{rd}$ Edition (John Wiley & Sons, New York, 1999). N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-n itrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

Indications

The compounds described herein are useful in treating tactile dysfunction, anxiety, and social impairment in a subject diagnosed with ASD, RTT, PMS, or Fragile X syndrome.

Tactile Dysfunction

Tactile dysfunction includes exhibiting symptoms such as withdrawing when being touched, refusing to eat certain "textured" foods and/or to wear certain types of clothing, complaining about having hair or face washed, avoiding getting hands dirty (e.g., glue, sand, mud, finger-paint), and using finger tips rather than whole hands to manipulate objects. Tactile dysfunction may lead to a misperception of touch and/or pain (hyper- or hyposensitive) and may lead to self-imposed isolation, general irritability, distractibility, and hyperactivity.

Anxiety

Anxiety includes emotions characterized by feelings of tension, worried thoughts and physical changes like increased blood pressure. Anxiety can be characterized by having recurring intrusive thoughts or concerns, avoiding certain situations (e.g., social situations) out of worry, and physical symptoms such as sweating, trembling, dizziness or a rapid heartbeat.

Social Impairment

Social impairment involves a distinct dissociation from and lack of involvement in relations with other people. It can occur with various mental and developmental disorders, such as autism. Social impairment may occur when an individual acts in a less positive way or performs worse when they are around others as compared to when alone. Nonverbal behaviors associated with social impairment can include deficits in eye contact, facial expression, and gestures that are used to help regulate social interaction. Often there is a failure to develop age-appropriate friendships. Social impairment can also include a lack of spontaneous seeking to share achievements or interests with other individuals. A person with social impairment may exhibit a deficit in social reciprocity with individuals, decreased awareness of others, lack of empathy, and lack of awareness of the needs of others.

Autism Spectrum Disorder

ASD is a heterogeneous group of neurodevelopmental disorders as classified in the fifth revision of the American Psychiatric Association's Diagnostic and Statistical Manual of Mental Disorders 5th edition (DSM-5). The DSM-5 redefined the autism spectrum to encompass the prior (DSM-IV-TR) diagnosis of autism, Asperger syndrome, pervasive developmental disorder not otherwise specified, childhood disintegrative disorder, and Rett syndrome. The autism spectrum disorders are characterized by social deficits and communication difficulties, stereotyped or repetitive behaviors and interests, and in some cases, cognitive delays. For example, an ASD is defined in the DSM-5 as exhibiting (i) deficits in social communication and interaction not caused by general developmental delays (must exhibit three criteria including deficits in social-emotional reciprocity, deficits in nonverbal communication, and deficits in creating and maintaining relationships appropriate to developmental level), (ii) demonstration of restricted and repetitive patterns of behavior, interest or activities (must exhibit two of the following four criteria: repetitive speech, repetitive motor movements or repetitive use of objects, adherence to routines, ritualized patterns of verbal or nonverbal, or strong resistance to change, fixated interests that are abnormally intense of focus, and over or under reactivity to sensory input or abnormal interest in sensory aspects of environment), (iii) symptoms must be present in early childhood, and (iv) symptoms collectively limit and hinder everyday functioning. ASD is also contemplated herein to include Dravet's syndrome and autistic-like behavior in non-human animals.

Rett Syndrome

Rett syndrome is an X-linked disorder that affects approximately one in ten-thousand girls. Patients go through four stages: Stage I) Following a period of apparently normal development from birth, the child begins to display social and communication deficits, similar to those seen in other autism spectrum disorders, between six and eighteen months of age. The child shows delays in their developmental milestones, particularly for motor ability, such as sitting and crawling. Stage II) Beginning between one and four years of age, the child goes through a period of regression in which they lose speech and motor abilities, developing stereotypical midline hand movements and gait impairments. Breathing irregularities, including apnea and hyperventilation also develop during this stage. Autistic symptoms are still prevalent at this stage. Stage III) Between age two and ten, the period of regression ends and symptoms plateau. Social and communication skills may show small improvements during this plateau period, which may last for most of the patients' lives. Stage IV) Motor ability and muscle deterioration continues. Many girls develop severe scoliosis and lose the ability to walk.

Phelan McDermid Syndrome

Phelan McDermid syndrome is a rare genetic condition caused by a deletion or other structural change of the terminal end of chromosome 22 in the 22q13 region or a disease-causing mutation of the Shank3 gene. Although the range and seventy symptoms may vary, PMS is generally thought to be characterized by neonatal hypotonia (low muscle tone in the newborn), normal growth, absent to severely delayed speech, moderate to profound developmental delay, and minor dysmorphic features. People who have PMS often show symptoms in very early childhood, sometimes at birth and within the first six months of life.

Fragile X Syndrome

Fragile X syndrome is an X chromosome-linked condition that is characterized by a visible constriction near the end of the X chromosome, at locus q27.3 that causes intellectual disability, behavioral and learning challenges and various physical characteristics Fragile X syndrome is the most common inherited form of mental retardation and developmental disability. Males with Fragile X syndrome usually have mental retardation and often exhibit characteristic physical features and behavior. Fragile X syndrome is characterized by behavior similar to autism and attention deficit disorder, obsessive-compulsive tendencies, hyperactivity, slow development of motor skills and anxiety fear disorder. When these disabilities are severe and occur simultaneously, the condition is sometimes described as autism, and may be associated with any degree of intelligence. Other characteristics are a likable, happy, friendly personality with a limited number of autistic-like features such as hand-flapping, finding direct eye contact unpleasant, and some speech and language problems. Physical features may include large ears, long face, soft skin and large testicles (called "macroorchidism") in post-pubertal males. Connective tissue problems may include ear infections, flat feet, high arched palate, double-jointed fingers and hyper-flexible joints.

Other Indications

The utility of peripherally-restricted GABAA receptor PAMs, agonists are not limited to treatment of the above indications; the compounds disclosed herein are also useful for treating touch over-reactivity and pain associated with other disease states, including Sensory Processing Disorder (SPD) and fibromyalgia, as well as mechanical allodynia associated with nerve injury, shingles, diabetic neuropathy, chemotherapy-induced neuropathy and other neuropathic pain states. Recent findings indicate that isoguvacine reduces tactile over-reactivity (mechanical allodynia) in rodent models of neuropathic pain.

Pharmaceutical Compositions

The compounds described herein (e.g., the compounds of Formulas I-XIII; e.g., the compounds of Table 1) may be formulated into pharmaceutical compositions for administration to human subjects in a biologically compatible form suitable for administration in vivo. Pharmaceutical compositions typically include an active agent and a pharmaceutically acceptable excipient.

The compound can also be used in the form of the free base, in the form of salts, zwitterions, solvates, or as prodrugs, or pharmaceutical compositions thereof. All forms are within the scope of the invention. The compounds, salts, zwitterions, solvates, prodrugs, or pharmaceutical compositions thereof, may be administered to a patient in a variety of forms depending on the selected route of administration, as will be understood by those skilled in the art. The compounds described herein may be administered, for example, by oral, parenteral, buccal, sublingual, nasal, rectal, patch, pump, or transdermal administration, and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

For human use, the compounds described herein can be administered alone or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers including excipients and auxiliaries that facilitate processing of compounds into preparations which can be used pharmaceutically.

The excipient or carrier is selected on the basis of the mode and route of administration. Suitable pharmaceutical carriers, as well as pharmaceutical necessities for use in pharmaceutical formulations, are described in Remington: The Science and Practice of Pharmacy, 22nd Ed., Allen, Ed. (2012), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents, e.g., talc, magnesium stearate, and mineral oil; wetting agents; emulsifying and suspending agents; preserving agents, e.g., methyl- and propylhydroxy-benzoates; sweetening agents; and flavoring agents. Other exemplary excipients are described in Handbook of Pharmaceutical Excipients, 6th Edition, Rowe et al., Eds., Pharmaceutical Press (2009).

These pharmaceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in Remington: The Science and Practice of Pharmacy, 22nd Ed., Allen, Ed. (2012), and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical formulation. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

Dosages

The dosage of the compounds described herein (e.g., the compounds of Formulas I-XIII; e.g., the compounds of Table 1), or pharmaceutically acceptable salts or prodrugs thereof, or pharmaceutical compositions thereof, can vary depending on many factors, e.g., the pharmacodynamic properties of the compound, the mode of administration, the age, health, and weight of the recipient, the nature and extent of the symptoms, the frequency of the treatment, and the type of concurrent treatment, if any, and the clearance rate of the composition in the subject to be treated. One of skill in the art can determine the appropriate dosage based on the above factors. The active agent may be administered initially in a suitable dosage that may be adjusted as required, depending on the clinical response. In general, a suitable daily dose of an active agent will be that amount of the compound that is the lowest dose effective to produce a therapeutic effect. Such an effective dose will generally depend upon the factors described above.

In general, the dosage of a pharmaceutical composition or the active agent in a pharmaceutical composition may be in the range of from about 1 µg to about 10 g (e.g., 1 pg-10 pg, e.g., 2 pg, 3 pg, 4 pg, 5 pg, 6 pg, 7 pg, 8 pg, 9 pg, 10 pg, e.g., 10 pg-100 pg, e.g., 20 pg, 30 pg, 40 pg, 50 µg, 60 pg, 70 pg, 80 pg, 90 pg, 100 pg, e.g., 100 pg-1 ng, e.g., 200 pg, 300 pg, 400 pg, 500 pg, 600 pg, 700 pg, 800 pg, 900 pg, 1 ng, e.g., 1 ng-10 ng, e.g., 2 ng, 3 ng, 4 ng, 5 ng, 6 ng, 7 ng, 8 ng, 9 ng, 10 ng, e.g., 10 ng-100 ng, e.g., 20 ng, 30 ng, 40 ng, 50 ng, 60 ng, 70 ng, 80 ng, 90 ng, 100 ng, e.g., 100 ng-1 µg, e.g., 200 ng, 300 ng, 400 ng, 500 ng, 600 ng, 700 ng, 800 ng, 900 ng, 1 µg, e.g., 1-10 µg, e.g., 1 µg, 2 µg, 3 µg, 4 µg, 5 µg, 6 µg, 7 µg, 8 µg, 9 µg, 10 µg, e.g., 10 µg-100 µg, e.g., 20 µg, 30 µg, 40 µg, 50 µg, 60 µg, 70 µg, 80 µg, 90 µg, 100 µg, e.g., 100 µg-1 mg, e.g., 200 µg, 300 µg, 400 µg, 500 µg, 600 µg, 700 µg, 800 µg, 900 µg, 1 mg, e.g., 1 mg-10 mg, e.g., 2 mg, 3 mg, 4 mg, 5 mg, 6 mg, 7 mg, 8 mg, 9 mg, 10 mg, e.g., 10 mg-100 mg, e.g., 20 mg, 30 mg, 40 mg, 50 mg, 60 mg, 70 mg, 80 mg, 90 mg, 100 mg, e.g., 100 mg-1 g, e.g., 200 mg, 300 mg, 400 mg, 500 mg, 600 mg, 700 mg, 800 mg, 900 mg, 1 g, e.g., 1 g-10 g, e.g., 2 g, 3 g, 4 g, 5 g, 6 g, 7 g, 8 g, 9 g, 10 g).

The pharmaceutical composition or the active agent may also be administered as a unit dose form or as a dose per mass or weight of the patient from about 0.01 mg/kg to about 100 mg/kg (e.g., 0.01-0.1 mg/kg, e.g., 0.02 0.03 mg/kg, 0.04 mg/kg, 0.05 mg/kg, 0.06 mg/kg, 0.07 mg/kg, 0.08 mg/kg, 0.09 mg/kg, 0.1 mg/kg, e.g., 0.1-1 mg/kg, e.g., 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, e.g., 1-10 mg/kg, e.g., 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, e.g., 10-100 mg/kg, e.g., 20 mg/kg, 30 mg/kg, 40 mg/kg, 50 mg/kg, 60 mg/kg, 70 mg/kg, 80 mg/kg, 90 mg/kg, 100 mg/kg). The dose may also be administered as a dose per mass or weight of the patient per unit day (e.g., 0.1-10 mg/kg/day).

The dosage regimen may be determined by the clinical indication being addressed (e.g., ASD, RTT, PMS, or Fragile X syndrome, e.g., social impairment or anxiety), as well as by various patient variables (e.g., weight, age, sex) and clinical presentation (e.g., extent or severity of tactile sensitivity, anxiety, or social impairment). Furthermore, it is understood that all dosages may be continuously given or divided into dosages given per a given time frame. The composition may be administered, for example, every hour, day, week, month, or year.

Formulations

The compounds described herein may be administered to patients or animals with a pharmaceutically acceptable diluent, carrier, or excipient, in unit dosage form. The compounds for use in treatment of ASD, RTT, PMS, or Fragile X syndrome may be produced and isolated by any standard technique known to those in the field of medicinal chemistry. Conventional pharmaceutical practice may be employed to provide suitable formulations or compositions to administer the compound to patients diagnosed with ASD, RTT, PMS, or Fragile X syndrome.

Exemplary routes of administration of the compounds, or pharmaceutical compositions thereof, used in the present invention include oral, sublingual, buccal, transdermal, intradermal, intramuscular, parenteral, intravenous, intraarterial, intracranial, subcutaneous, intraorbital, intraventricular, intraspinal, intraperitoneal, intranasal, inhalation, intrathecal and topical administration. The compounds may be administered with a pharmaceutically acceptable carrier.

Formulations for Oral Administration

The pharmaceutical compositions contemplated by the invention include those formulated for oral administration. Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate), granulating and disintegrating agents (e.g., cellulose derivatives including microcrystalline cellulose, starches including potato starch, croscarmellose sodium, alginates, or alginic acid), binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol), and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration versus time profile. In one example, controlled release is obtained by appropriate selection of various formulation parameters and ingredients, including, e.g., various types of controlled release compositions and coatings. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion-controlled release can be achieved by appropriate coating of a tablet, capsule, pellet, or granulate formulation of the compounds described herein, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils, e.g., cottonseed oil, sesame oil, coconut oil, or peanut oil, as well as elixirs and similar pharmaceutical vehicles.

Formulations for Parenteral Administration

The compounds described herein can be administered in a pharmaceutically acceptable parenteral (e.g., intravenous or intramuscular) formulation as described herein. The pharmaceutical formulation may also be administered parenterally (intravenous, intramuscular, subcutaneous or the like) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. For example, to prepare such a composition, the compounds may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl, or n-propyl p-hydroxybenzoate. Additional information regarding parenteral formulations can be found, for example, in the United States Pharmacopeia-National Formulary (USP-NF), herein incorporated by reference.

Exemplary formulations for parenteral administration include solutions of the compound prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington: The Science and Practice of Pharmacy, 22nd Ed., Allen, Ed. (2012) and in The United States Pharmacopeia: The National Formulary (USP 36 NF31), published in 2013.

Formulations for parenteral administration may, for example, contain excipients, sterile water, or saline, polyalkylene glycols, e.g., polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for the compounds described herein include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The parenteral formulation can be formulated for prompt release or for sustained/extended release of the compound. Exemplary formulations for parenteral release of the compound include aqueous solutions, powders for reconstitution, cosolvent solutions, oil/water emulsions, suspensions, oil-based solutions, liposomes, microspheres, and polymeric gels.

EXAMPLES

Example 1. Materials and Methods

The compounds described herein are synthesized according to the following methods. All starting materials in the synthetic schemes are prepared according to procedures known to one of skill in the art.

Scheme 1

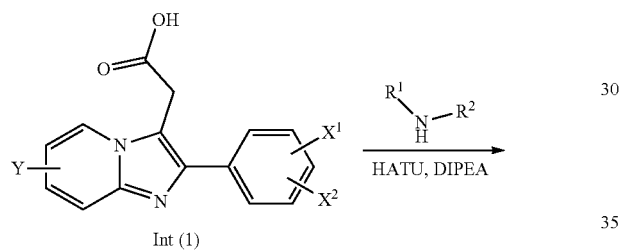

Scheme 2

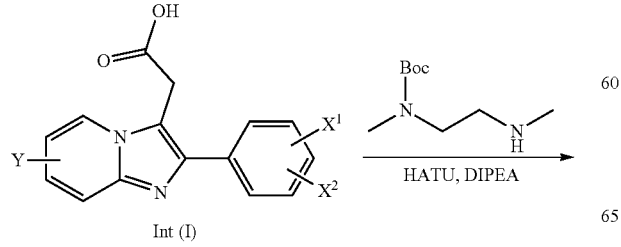

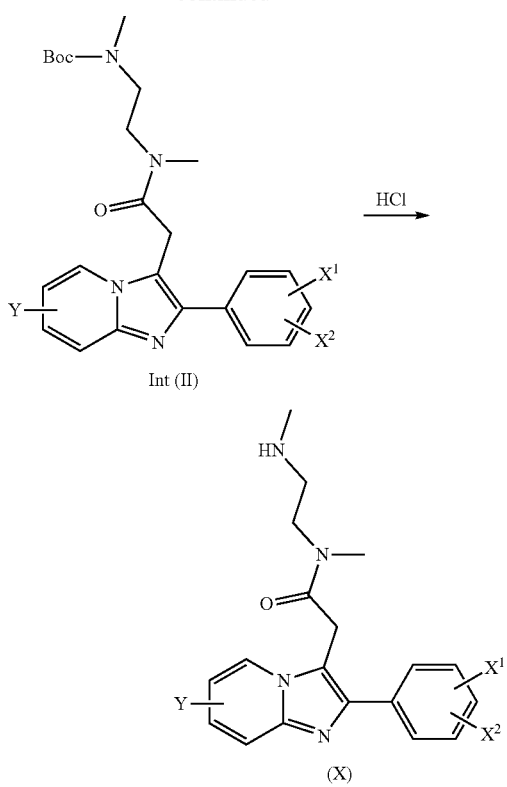

Scheme 3

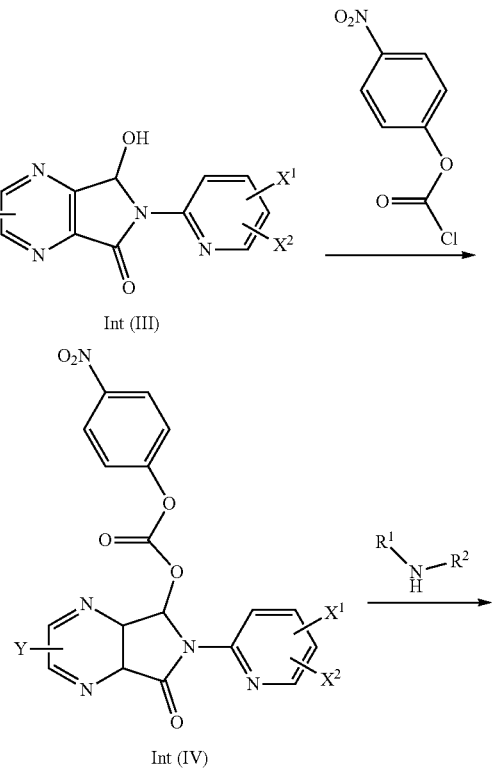

-continued
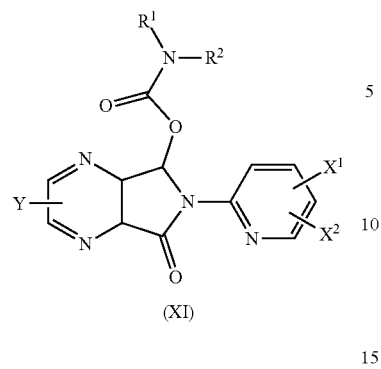
(XI)
Scheme 4
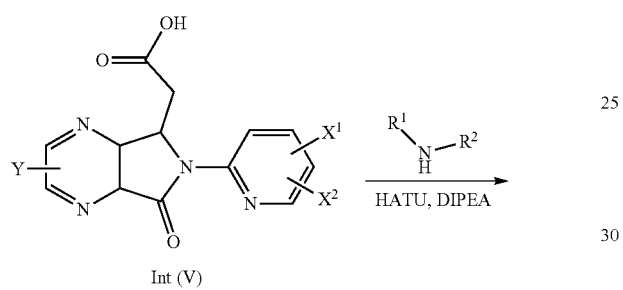
Int (V)
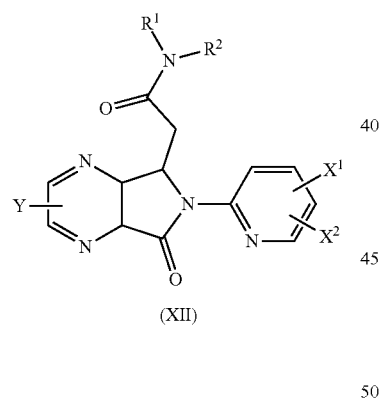
(XII)
Scheme 5
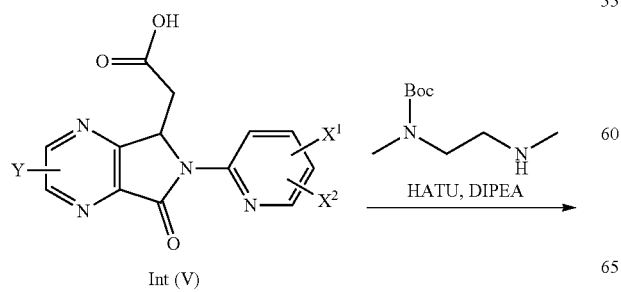
Int (V)
-continued
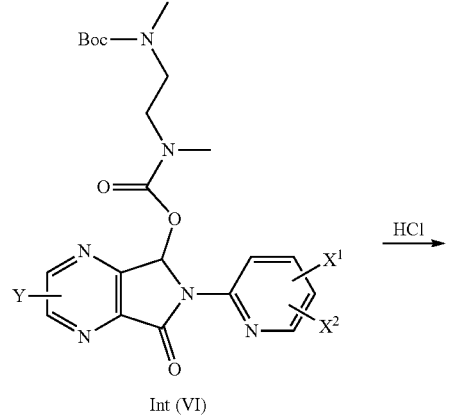
Int (VI)
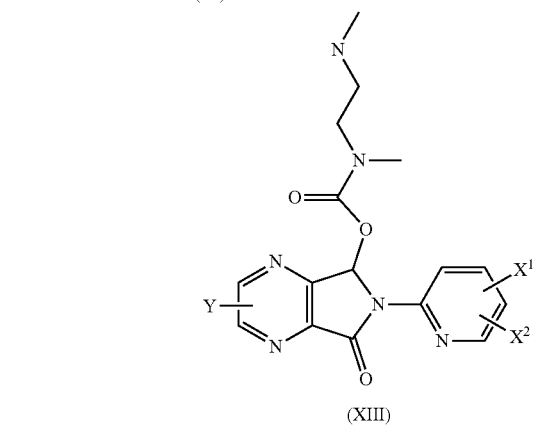
(XIII)
Example 2. Synthesis of Compounds 36, 37, 38, and 39
Scheme 6
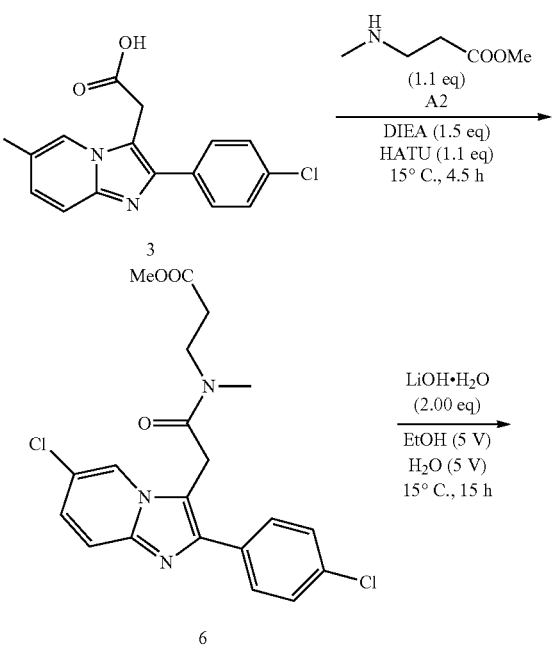

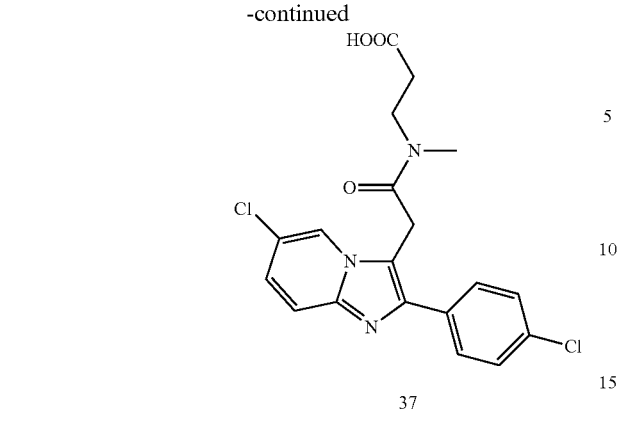
37
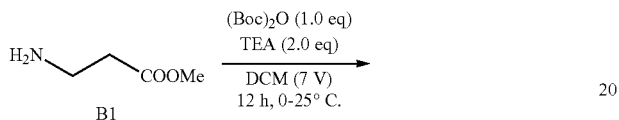
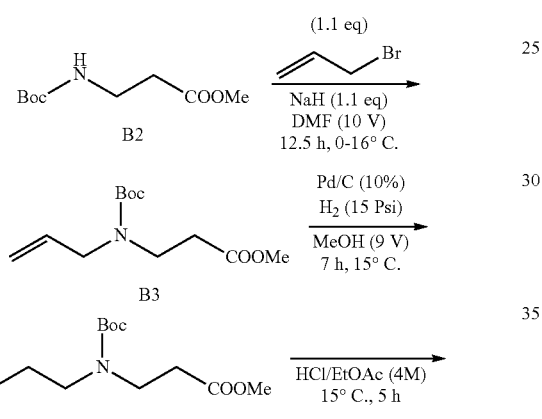
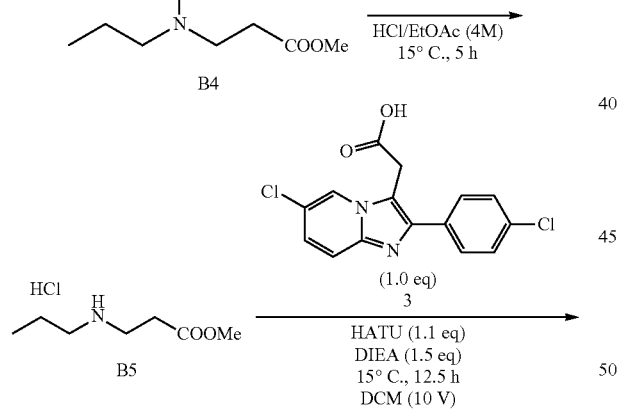
7
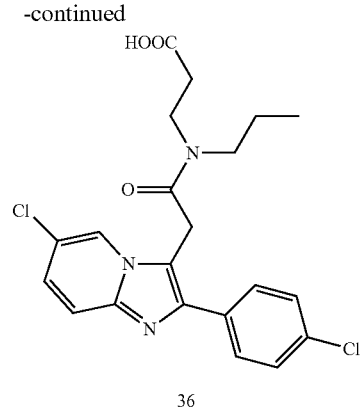
36
Scheme 7
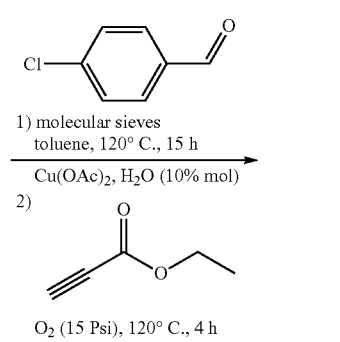
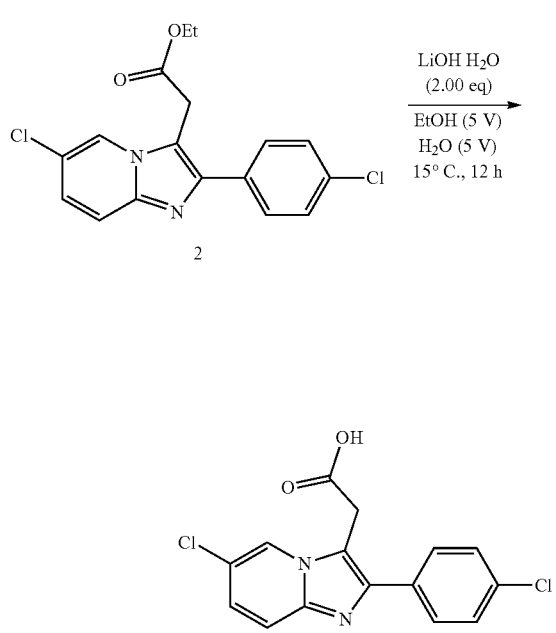
3

-continued
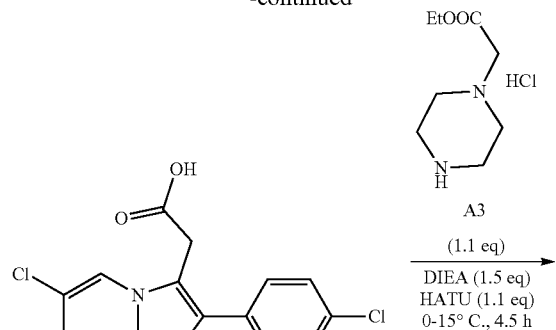
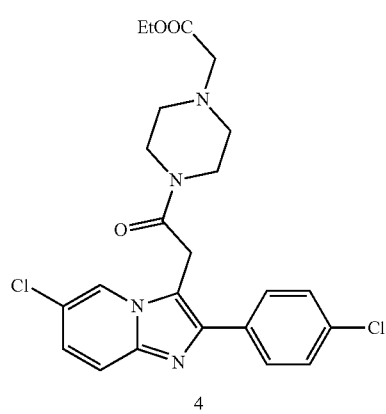
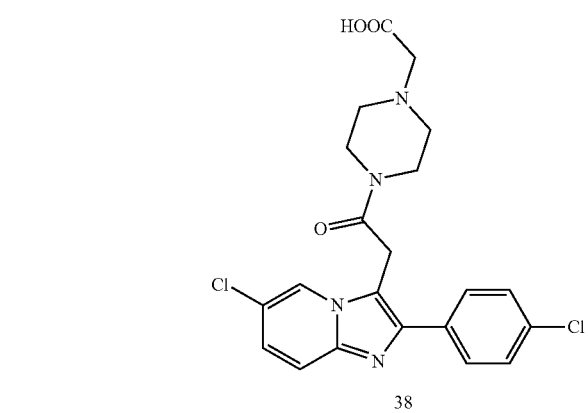
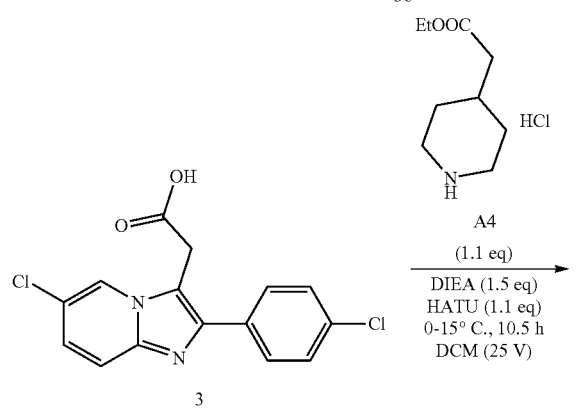
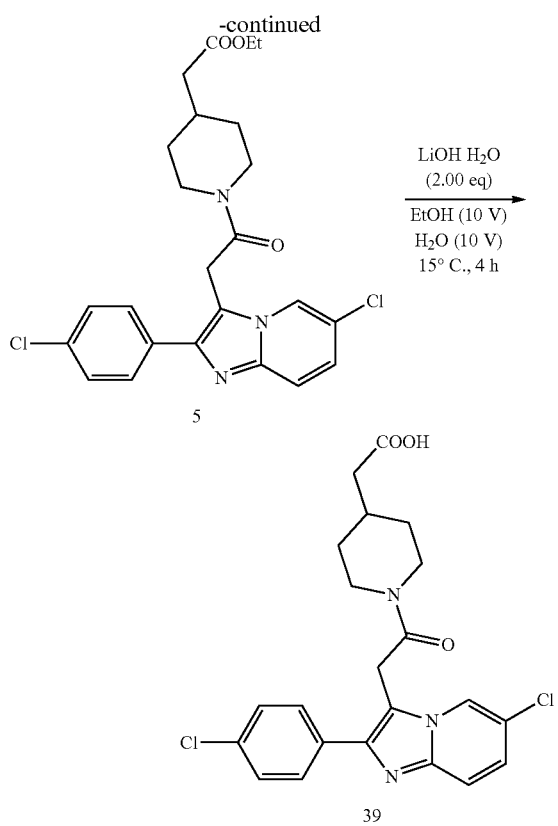
General Procedure for Preparation of Intermediate 2
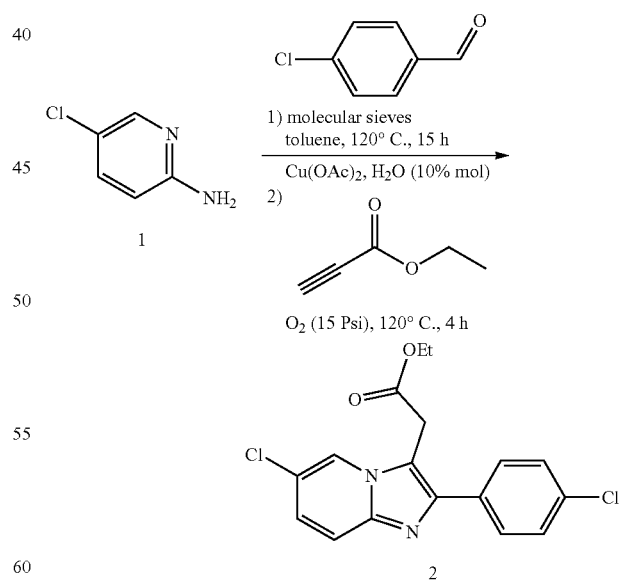
A mixture of compound 1 (20 g, 155 mmol, 1.00 eq) 4-chlorobenzaldehyde (26.2 g, 186 mmol, 1.20 eq) in toluene (200 mL) was degassed and purged with N₂ for 3 times, and then the mixture was stirred at 120° C. for 15 h under N₂ atmosphere. The resulting mixture containing imine was cooled down to 25° C. and ethyl prop-2-ynoate (30.5 g, 311 mmol, 30.5 mL, 2.00 eq), Cu(OAc)₂ (18.1 g, 0.1 mol, 6.43e-1 eq) and H₂O (2 mL) was added. The reaction mixture was stirred additionally at 120° C. for 4 h under 02 atmosphere. TLC (plate1) (Petroleum ether:Ethyl acetate=1: 1, $R_f$=0.72) indicated ~5% of Reactant 1 was remained, and one major new spot with lower polarity was detected. TLC (plate 2) (Petroleum ether:Ethyl acetate=4:1, $R_f$=0.03) indicated intermediate was consumed completely and many new spots formed. TLC (plate3) (Petroleum ether:Ethyl acetate=1:1, $R_f$=0.56) indicated one major new spot was detected. LC-MS showed intermediate was consumed completely and desired mass was detected. The reaction mixture was concentrated under reduced pressure to give a residue. The residue was purified by column chromatography (SiO₂, Petroleum ether/Ethyl acetate=20/1 to 5:1). Compound 2 (7 g, 18.04 mmol, 11.60% yield, 90% purity) was obtained as a yellow solid.

¹H NMR: ET25189-1-p1a1 400 MHz CDCl3

δ 8.13 (s, 1H), 7.71 (d, J=8.8 Hz, 2H), 7.54 (d, J=9.6 Hz, 1H), 7.40 (d, J=8.8 Hz, 2H), 7.13-7.19 (m, 1H), 4.15-4.20 (dd, J=7.2, 7.2 Hz, 2H), 3.92 (s, 2H), 1.25 (t, J=8.4 Hz, 3H),

General Procedure for Preparation of Intermediate 3

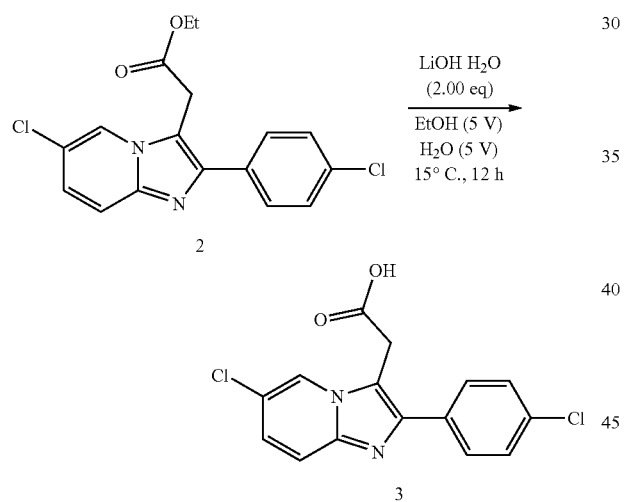

To a solution of compound 2 (1.10 g, 3.15 mmol, 1.00 eq) in EtOH (5 mL) was added LiOH·H₂O (264 mg, 6.30 mmol, 2.00 eq) and H₂O (5 mL). The mixture was stirred at 15° C. for 12 h. TLC (Petroleum ether:Ethyl acetate=1:1, $R_f$=0.04) indicated Reactant 2 was consumed completely and two new spots formed. The reaction mixture was diluted with H₂O (20 mL), and extracted with EtOAc (20 mL×3). Then the aqueous phase was added HCl (2M) dropwise, the pH value was adjusted to around 3, and extracted with EtOAC (20 mL×2), the combined organic layers were dried over Na₂SO₄, filtered and concentrated under reduced pressure to give a residue. The crude product was used into the next step without further purification. Compound 3 (1 g, 3.11 mmol, 98.85% yield) was obtained as a yellow solid.

¹H NMR: ET25189-6-p1a1 400 MHz CDCl₃

δ 8.71 (s, 1H), 7.75 (d, J=6.8 Hz, 2H), 7.66 (d, J=9.6 Hz, 1H), 7.55 (d, J=8.8 Hz, 2H), 7.33-7.36 (m, 1H), 4.17 (s, 2H).

General Procedure for Preparation of Intermediate 4

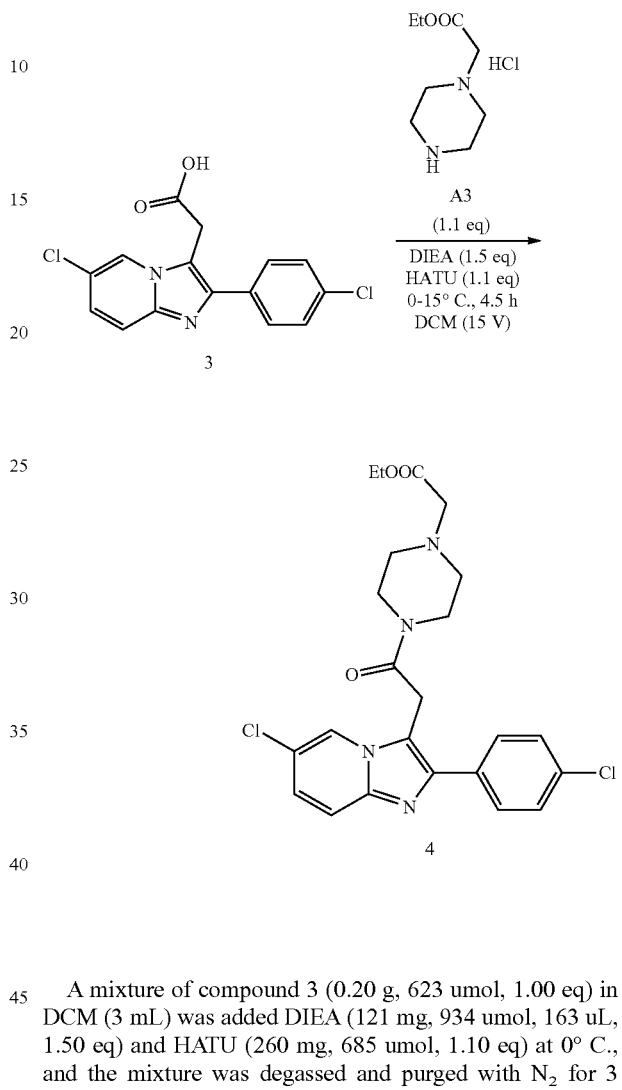

A mixture of compound 3 (0.20 g, 623 umol, 1.00 eq) in DCM (3 mL) was added DIEA (121 mg, 934 umol, 163 uL, 1.50 eq) and HATU (260 mg, 685 umol, 1.10 eq) at 0° C., and the mixture was degassed and purged with N₂ for 3 times, and then was stirred at 15° C. for 0.5 h under N₂ atmosphere. Then piperazin-1-ylmethyl propanoate (143 mg, 685 umol, 1.10 eq, HCl) was added the mixture at 0° C. The mixture was stirred at 15° C. for 4 h under N₂ atmosphere. LC-MS showed compound 3 was consumed completely and desired mass was detected. The reaction mixture was diluted with H₂O (10 mL), and extracted with EtOAc (20 mL×3). The combined organic layers were dried over Na₂SO₄, filtered and concentrated under reduced pressure to give a residue. The crude product was used into the next step without further purification. Compound 4 (0.4 g, crude) was obtained as a yellow solid.

¹H NMR: ET25189-4-P1A1 400 MHz CDCl₃

δ 8.18-8.24 (m, 1H), 7.65 (d, J=9.6 Hz, 1H), 7.21 (d, J=8.4 Hz, 1H), 7.18 (d, J=8.4 Hz, 2H), 7.24-7.28 (m, 2H), 4.13 (q, J=14 Hz, 2H), 3.99 (s, 2H), 3.60-3.63 (m, 2H), 3.42 (t, J=4.8 Hz, 2H), 3.21 (s, 2H). 3.10 (q, J=14.8 Hz, 2H), 2.55-2.58 (m, 2H), 1.18-1.22 (m, 3H).

General Procedure for Preparation of Compound 38

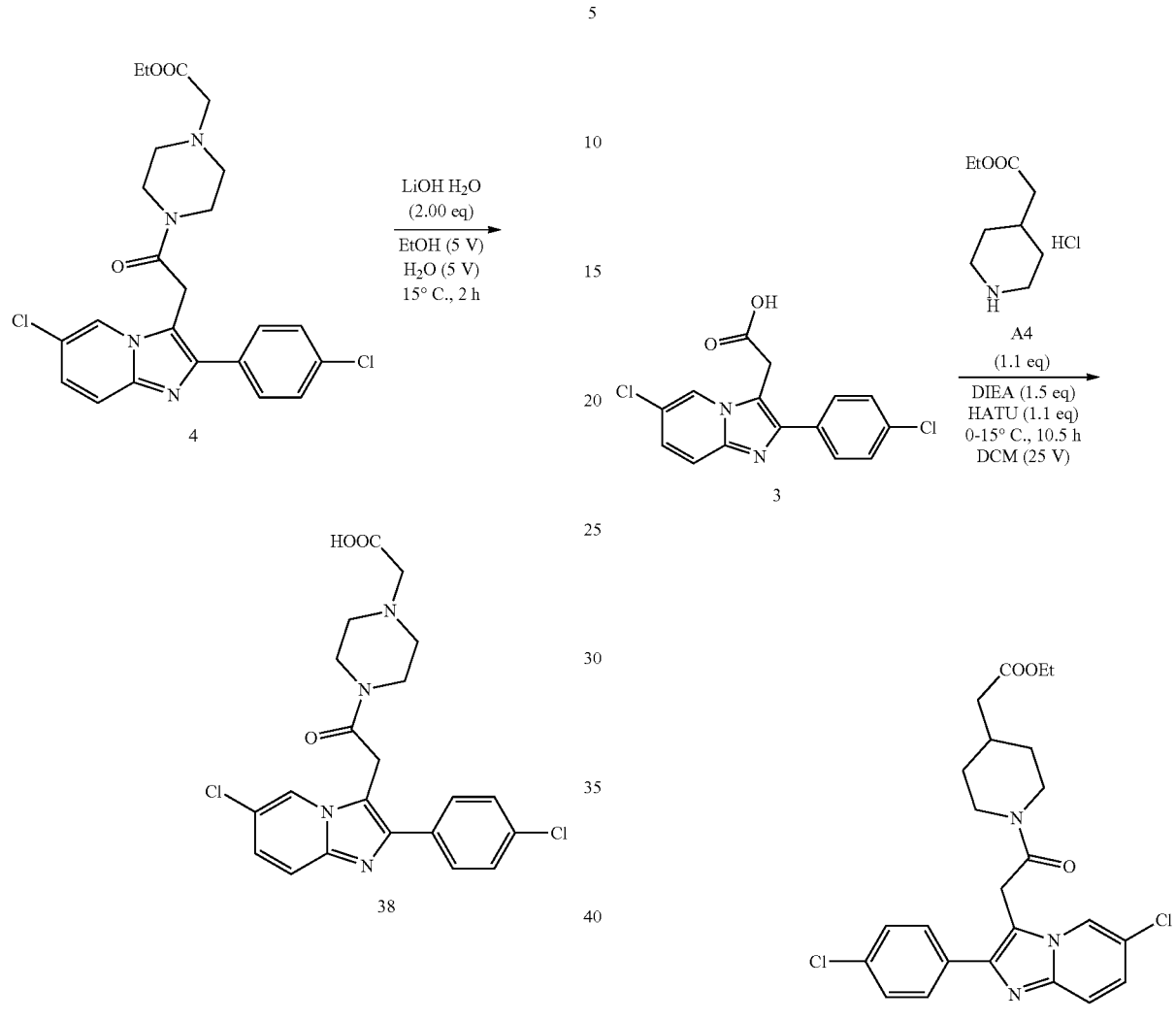

General Procedure for Preparation of Intermediate 5

To a solution of compound 4 (0.40 g, 841 umol, 1.00 eq) in EtOH (2 mL) was added LiOH·H$_2$O (70.6 mg, 1.68 mmol, 2.00 eq) and H$_2$O (2 mL). The mixture was stirred at 15° C. for 2 h. TLC (Dichloromethane:Methanol=10:1, R$_f$=0.02) indicated compound 4 was consumed completely and two new spots formed. The reaction mixture was diluted with H$_2$O (10 mL), and extracted with EtOAc (20 mL×3). Then the aqueous phase was added HCl (2M) dropwise, the pH value was adjusted to around 3, and extracted with EtOAC (20 mL×2). The combined organic layers were dried over Na$_2$SO$_4$, filtered and concentrated under reduced pressure to give a residue. The residue was further purification by pre-HPLC (column: Waters Xbridge 150*25 5u; mobile phase: [water (10 mM NH$_4$HCO3)-ACN]; B %: 15%-35%, 10 min) to give as white solid. Compound Target 3 (0.05 g, 111 umol, 13.2% yield) was obtained as a white solid.

$^1$H NMR: ET25189-5-p1a1 400 MHz DMSO-d$_6$

δ 8.61 (s, 1H), 7.66 (d, J=8.4 Hz, 3H), 7.55 (d, J=8.8 Hz, 2H), 7.34 (d, J=9.6 Hz, 1H), 4.29 (s, 2H), 3.64 (s, 2H), 3.51 (s, 2H), 3.25 (s, 2H), 2.65-2.68 (m, 2H), 2.55-2.56 (m, 2H).

LCMS: ET25189-5-P1A1 (M/2+H+=224.1, M+H$^+$= 447.1)

HPLC: ET25189-5-P1A1, RT, 2.019

A solution of compound 3 (0.2 g, 623 umol, 1.00 eq) in DCM (5.00 mL) was added DIEA (121 mg, 934 umol, 163 uL, 1.50 eq) HATU (260 mg, 685 umol, 1.10 eq) at 0° C. The mixture was degassed and purged with N$_2$ for 3 times, and was stirred at 15° C. for 0.5 h under N$_2$ atmosphere. After ethyl 2-(4-piperidyl) acetate (142 mg, 685 umol, 1.10 eq, HCl) was added the mixture at 0° C., and the mixture was stirred at 15° C. for 10 h. LC-MS showed compound 3 was consumed completely and desired mass was detected. The reaction mixture was diluted with H$_2$O (10 mL), and extracted with EtOAc (20 mL×3). The combined organic layers were dried over Na$_2$SO$_4$, filtered and concentrated under reduced pressure to give a residue. The crude product was used into the next step without further purification. Compound 5 (0.35 g, crude) was obtained as a brown solid.

General Procedure for Preparation of Compound 39

General Procedure for Preparation of Intermediate 6

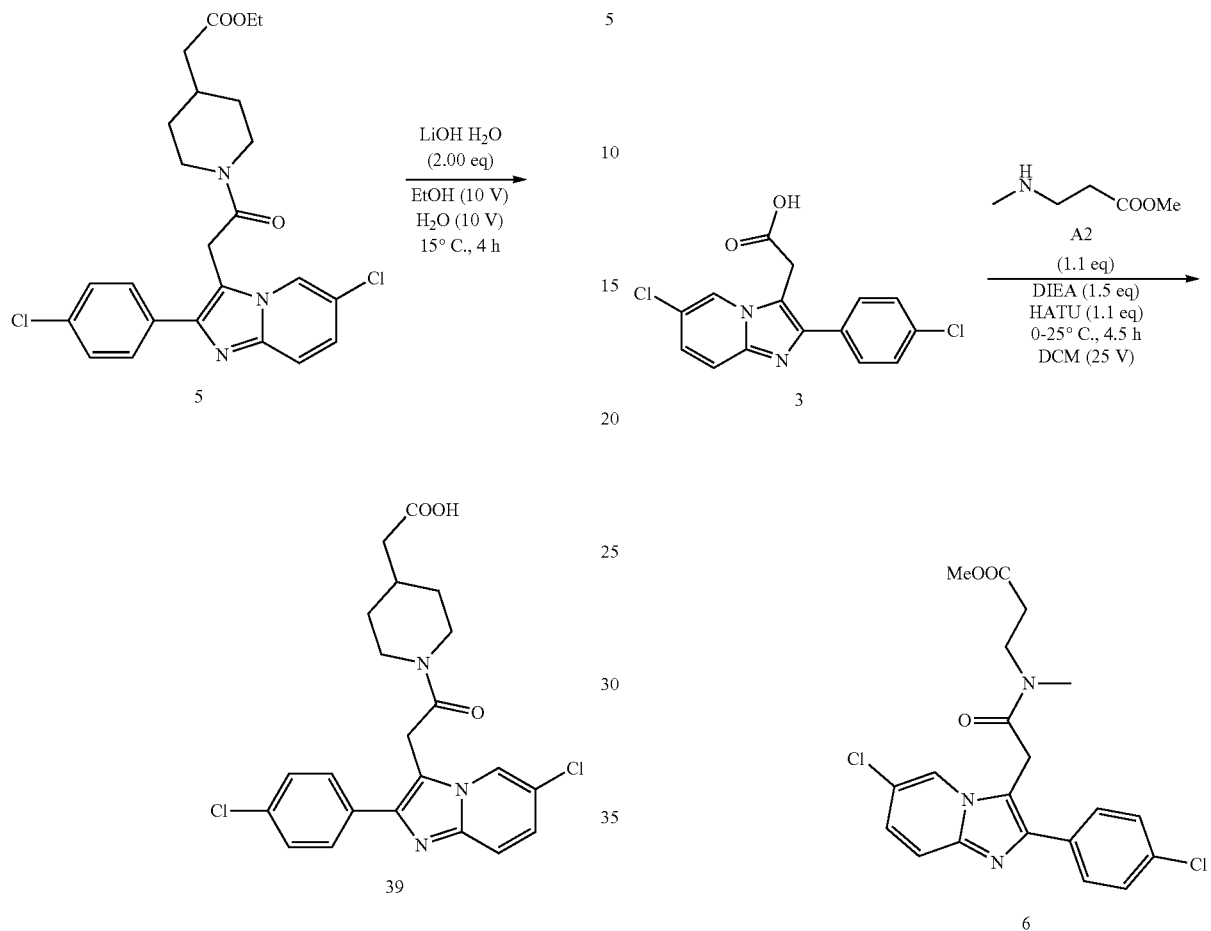

To a solution of compound 5 (0.35 g, 738 umol, 1.00 eq) in EtOH (3 mL) was added LiOH·H$_2$O (61.9 mg, 1.48 mmol, 2.00 eq) and H$_2$O (3 mL). The mixture was stirred at 15° C. for 4 h. LC-MS showed compound 5 was consumed completely and desired mass was detected. The reaction mixture was diluted with H$_2$O (20 mL), and extracted with EtOAC (20 mL×2). Then the aqueous phase was added HCl (2M) dropwise, the pH value was adjusted to around 3, and extracted with EtOAc (20 mL), the combined organic layers were dried over Na$_2$SO$_4$, filtered and concentrated under reduced pressure to give a residue. The residue was further purification by pre-HPLC (column: Waters Xbridge 150*25 5u; mobile phase: [water (10 mM NH$_4$HCO3)-ACN]; B %: 5%-35%, 10 min) to give product as white solid. Compound Target4 (0.05 g, 112 umol, 15.2% yield) was obtained as a white solid.

$^1$H NMR: ET25189-9-p1a1 400 MHz DMSO d$_6$

δ 12.11 (s, 1H), 8.56 (s, 1H), 7.61-7.63 (m, 3H), 7.54 (d, J=8.8 Hz, 2H), 7.31 (d, J=8.8 Hz, 1H), 4.32 (d, J=11.6 Hz, 1H), 4.24 (s, 2H), 4.00 (d, J=13.2 Hz, 1H), 3.15 (t, J=16.4 Hz, 1H), 2.66-2.63 (m, 1H), 2.21 (d, J=6.8 Hz, 2H), 1.93 (br s, 1H), 1.74 (t, J=6.8 Hz, 2H), 1.20-1.22 (m, 1H), 1.06-1.07 (m, 1H).

LCMS: ET25189-9-P1A1 (M+H$^+$=446.1)

HPLC: ET25189-9-P1A1, RT, 2.030

A mixture of compound 3 (0.20 g, 622 umol, 1.00 eq) in DCM (5 mL) was added DIEA (121 mg, 934 umol, 163 uL, 1.50 eq), HATU (260 mg, 685 umol, 1.10 eq) at 0° C. The mixture was degassed and purged with N$_2$ for 3 times, and was stirred at 25° C. for 0.5 h under N$_2$ atmosphere. And then methyl 3-(methylamino) propanoate (80.3 mg, 522 umol, 1.10 eq) was added the mixture at 0° C. Then the mixture was stirred at 25° C. for 4 h. LC-MS showed compound 3 was consumed completely and desired mass was detected. The residue was diluted with H$_2$O (20 mL) and extracted with DCM (20 mL×2). The combined organic layers were dried over Na$_2$SO$_4$, filtered and concentrated under reduced pressure to give a residue. The crude product was used into the next step without further purification. Compound 6 (0.4 g, crude) was obtained as a brown solid.

$^1$H NMR: ET25189-10-p1a1 400 MHz CDCl$_3$

δ 8.10-8.17 (m, 1H), 7.48-7.53 (m, 2H), 7.37 (t, J=8.4 Hz, 2H), 7.11 (d, J=1.4 Hz, 2H), 4.20 (s, 1H), 3.95 (s, 1H), 3.67 (s, 1H), 3.60-3.64 (m, 2H), 3.59 (s, 3H), 2.99 (s, 2H), 2.50-2.64 (m, 2H).

General Procedure for Preparation of Compound 37

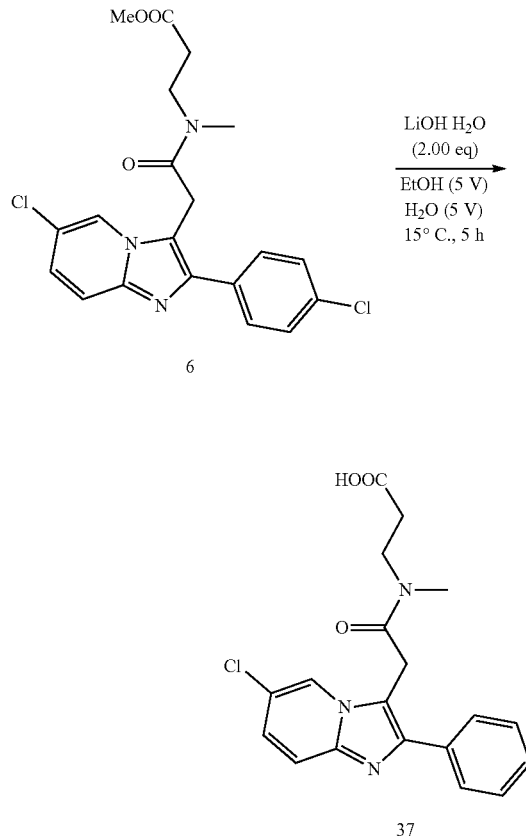

To a solution of compound 6 (0.4 g, 952 umol, 1.00 eq) in EtOH (2 mL) was added LiOH·H$_2$O (79.9 mg, 1.90 mmol, 2.00 eq) and H$_2$O (2 mL). The mixture was stirred at 15° C. for 5 h. LC-MS showed compound 6 was consumed completely and desired mass was detected. The reaction mixture was diluted with H$_2$O (20 mL), and extracted with EtOAc (20 mL×2). Then the aqueous phase was added HCl (2M) dropwise, the pH value was adjusted to around 3, and extracted with EtOAc (20 mL), the combined organic layers were dried over Na$_2$SO$_4$, filtered and concentrated under reduced pressure to give a residue. The residue was further purification by pre-HPLC (column: Nano-micro Kromasil C18 100*30 mm 5 um; mobile phase: [water (10 mM NH$_4$HCO3)-ACN]; B %: 15%-30%, 10 min) to give product (P1) as white solid. The product (P1) was further purification by pre-HPLC (column: Waters Xbridge BEH C18 100*25 mm*5 um; mobile phase: [water (10 mM NH$_4$HCO3)-ACN]; B %: 2%-30%, 10 min) to give product (P2) as white solid. Compound Target 2 (0.05 g, 123 umol, 12.9% yield) was obtained as a white solid.

$^1$H NMR: ET25189-11-p2a3 400 MHz DMSO d$_6$

δ 8.50-8.53 (m, 1H), 7.60-7.65 (m, 3H), 7.50-7.52 (m, 2H), 7.31 (d, J=6.4 Hz, 1H), 4.36 (s, 1H), 4.19 (s, 1H), 3.69 (t, J=7.2 Hz, 1H), 3.55 (t, J=7.2 Hz, 1H), 3.13 (s, 2H), 2.83 (s, 1H), 2.63 (m, 1H), 2.43 (s, 1H).

LC-MS: ET25189-11-P2A1 (M+H$^+$=406.0)

HPLC: ET25189-11-P2A1, RT=1.935

General Procedure for Preparation of Compound 82

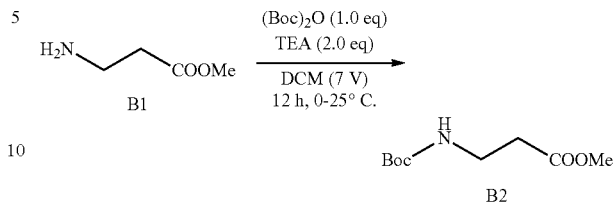

To a solution of compound B1 (4.00 g, 28.7 mmol, 1.00 eq, HCl) in DCM (30 mL) was added TEA (5.80 g, 57.3 mmol, 7.98 mL, 2.00 eq) at 0° C., and added Boc2O (6.25 g, 28.7 mmol, 6.58 mL, 1.00 eq). The mixture was stirred at 25° C. for 12 h. TLC (Petroleumether:Ethyl acetate=1:1, R$_f$=0.48) indicated compound B1 was consumed completely and two new spots formed. The reaction mixture was diluted with H$_2$O (30 mL) and extracted with EtOAc (20 mL×2). The combined organic layers were washed with NaCl (10 mL), dried over Na$_2$SO$_4$, filtered and concentrated under reduced pressure to give a residue. The crude product was used into the next step without further purification. Compound B2 (4.8 g, 23.62 mmol, 82.42% yield) was obtained as colorless oil.

$^1$H NMR: ET22607-39-p1a1 400 MHz CDCl$_3$

δ 5.00 (br s, 1H), 3.69 (s, 3H), 3.40 (m, 2H), 2.53 (t, J=10 Hz, 2H), 1.42 (s, 9H).

General Procedure for Preparation of Compound 83

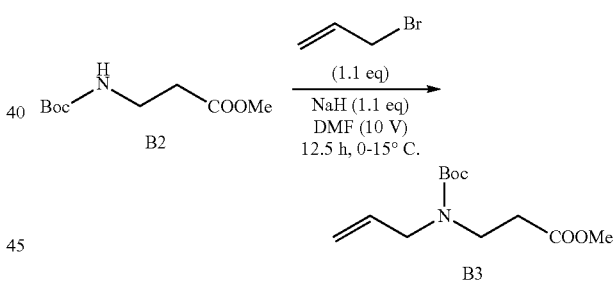

To a solution of compound B2 (1.52 g, 7.48 mmol, 1.00 eq) in DMF (15 mL) was added NaH (329 mg, 8.23 mmol, 60% purity, 1.10 eq) at 0° C., and the mixture was degassed and purged with N$_2$ for 3 times, and then the mixture was stirred at 15° C. for 0.5 h under N$_2$ atmosphere. After 3-bromoprop-1-ene (995 mg, 8.23 mmol, 247 uL, 1.10 eq) was added the mixture, and the mixture was stirred at 15° C. for 12 h. TLC (Petroleum ether: Ethyl acetate=5:1, R$_f$=0.56) indicated compound B2 was consumed completely and three new spots formed. The reaction mixture was quenched by addition NH$_4$Cl (20 mL), and then diluted with H$_2$O (20 mL) and extracted with EtOAc mL (20 mL×3). The combined organic layers were dried over Na$_2$SO$_4$, filtered and concentrated under reduced pressure to give a residue. The residue was purified by silica gel column chromatography (Petroleum ether/Ethyl acetate=20:1, 10:1) to afford compound B3 as a colorless oil. Compound B3 (0.80 g, 3.29 mmol, 43.9% yield) was obtained as a colorless oil.

$^1$H NMR: ET22607-47-p1a1 400 MHz CDCl$_3$

δ 5.64-5.74 (m, 1H), 5.06 (d, J=7.6 Hz 2H), 3.76 (br s, 2H), 3.60 (s, 3H), 3.40 (br s, 2H), 2.51 (m, 2H), 1.38 (s, 9H).

General Procedure for Preparation of Compound 84

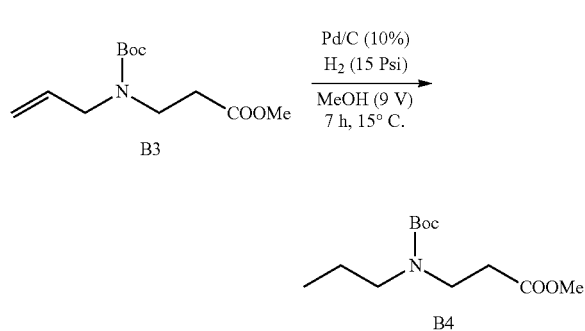

To a solution of compound B3 (0.80 g, 3.29 mmol, 1.00 eq) in MeOH (7 mL) was added Pd/C (0.50 g, 10% purity). The suspension was degassed under vacuum and purged with H$_2$ several times. The mixture was stirred under H$_2$ (15 Psi) at 15° C. for 7 hrs. TLC (Petroleum ether:Ethyl acetate=5:1, R$_f$=0.49) indicated Reactant B3 was consumed completely and two new spots formed. The reaction mixture was filtered and the filtrate was concentrated under reduced pressure to give a residue. The crude product was used into the next step without further purification. Compound B4 (0.8 g, 3.26 mmol, 99.2% yield) was obtained as a colorless oil.

$^1$H NMR: ET22607-49-p1a1 400 MHz CDCl$_3$

δ 3.67 (s, 3H), 3.46 (br d, 2H), 3.14 (br s, 2H), 2.56 (br d, 2H), 1.51-1.56 (m, 2H), 1.44 (m, 9H), 0.88 (t, J=7.2 Hz, 3H).

General Procedure for Preparation of Compound 85

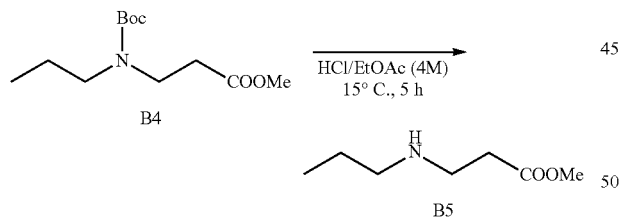

A solution of compound B4 (0.80 g, 3.26 mmol, 1.00 eq) in HCl/EtOAc (4 M, 20 mL) was stirred at 15° C. for 5 h. LC-MS showed ~2.4% of Reactant B4 was remained. Several new peaks were shown on LC-MS and ~57% of desired compound was detected. The reaction mixture was concentrated under reduced pressure to give a residue. The crude product was used into the next step without further purification. Compound B5 (440 mg, 2.42 mmol, 74.2% yield, HCl) was obtained as a white solid.

$^1$H NMR: ET22607-50-p1a1 400 MHz DMSO d$_6$

δ 9.16 (br s, 1H), 3.62 (s, 3H), 3.09 (t, J=6.0 Hz, 2H), 2.81 (t, J=7.2 Hz, 4H), 1.56-1.66 (m, 2H), 0.90 (-t, J=6.0 Hz, 3H).

General Procedure for Preparation of Compound 7

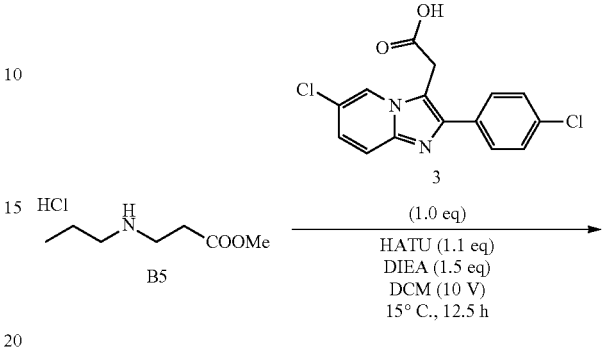

To a solution of compound 3 (0.3 g, 934 umol, 1.00 eq) in DCM (3 mL) was added DIEA (362 mg, 2.80 mmol, 488 uL, 3.00 eq) and HATU (391 mg, 1.03 mmol, 1.10 eq) at 0° C. The mixture was degassed and purged with N$_2$ for 3 times, and was stirred at 15° C. for 0.5 h under N$_2$ atmosphere. Then methyl 3-(propylamino)propanoate (187 mg, 1.03 mmol, 1.10 eq, HCl) was added the mixture at 0° C. The mixture was stirred at 0-15° C. for 12 h. LC-MS showed compound 3 was consumed completely and desired mass was detected. The residue was diluted with H$_2$O (20 mL) and extracted with DCM (20 mL×2). The combined organic layers were dried over Na$_2$SO$_4$, filtered and concentrated under reduced pressure to give a residue. The crude product was used into the next step without further purification. Compound 7 (0.6 g, crude) was obtained as a black solid.

$^1$H NMR: ET25189-15-p1a1 400 MHz CDCl$_3$

δ 8.16 (s, 1H), 7.48-7.56 (m, 3H), 7.36-7.38 (m, 2H), 7.10-7.13 (m, 1H), 4.15 (s, 1H), 3.66 (s, 1H), 3.63 (m, 1H), 3.57 (s, 1H), 3.54 (s, 3H), 3.53 (m, 1H), 3.24 (t, J=8.0 Hz, 1H), 3.17 (t, J=8.0 Hz, 1H), 2.53-2.55 (m, 1H), 2.48-2.51 (m, 1H), 1.14-1.50 (m, 2H), 0.71-0.75 (t, J=7.2 Hz, 3H).

General Procedure for Preparation of Compound 36

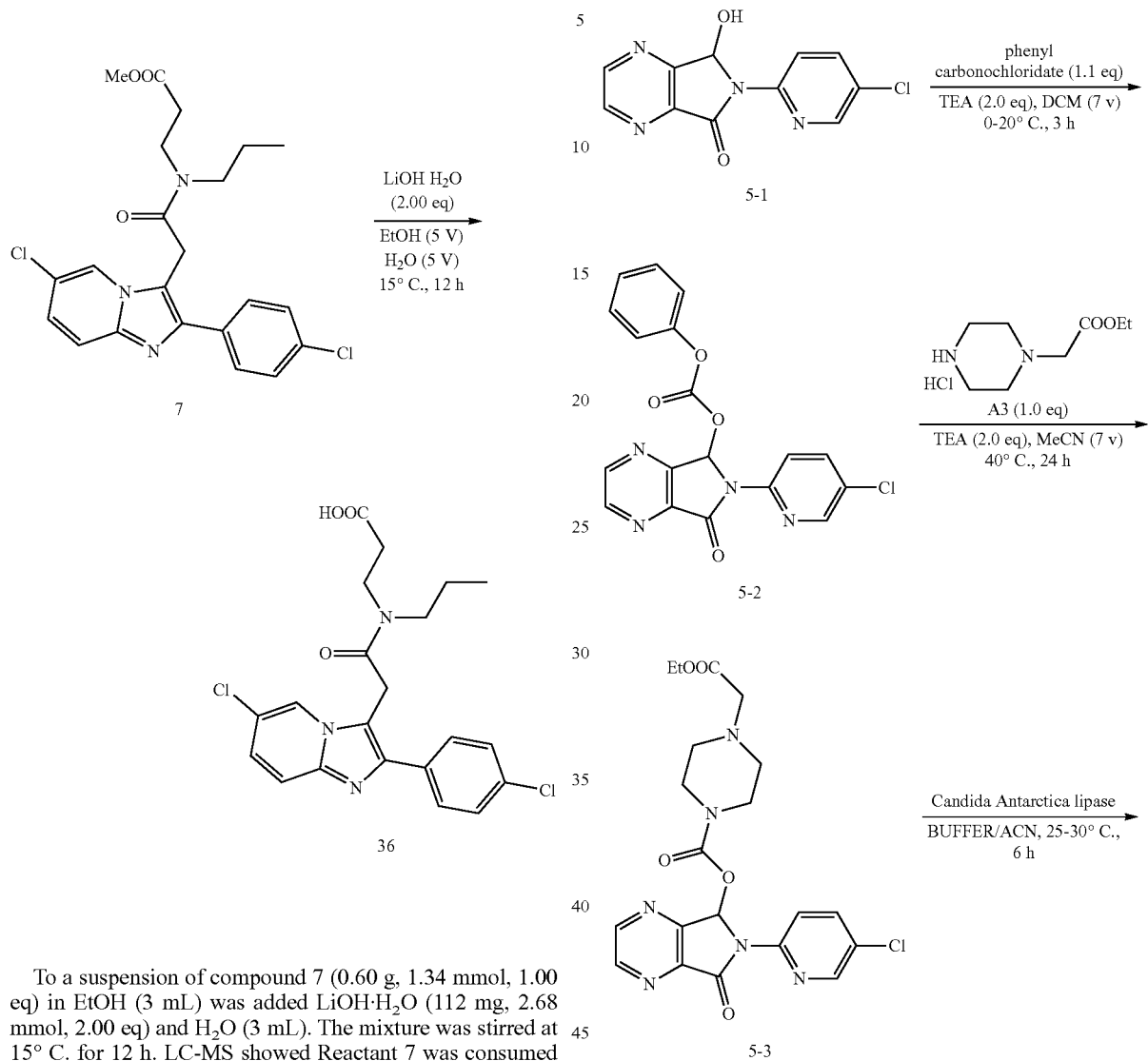

To a suspension of compound 7 (0.60 g, 1.34 mmol, 1.00 eq) in EtOH (3 mL) was added LiOH·H₂O (112 mg, 2.68 mmol, 2.00 eq) and H₂O (3 mL). The mixture was stirred at 15° C. for 12 h. LC-MS showed Reactant 7 was consumed completely and desired mass was detected. The reaction mixture was diluted with H₂O (20 mL), and extracted with EtOAC (20 mL×2). Then the aqueous phase was added HCl (2M) dropwise, the pH value was adjusted to around 3, and extracted with EtOAC (20 mL), the combined organic layers were dried over Na₂SO₄, filtered and concentrated under reduced pressure to give a residue. The residue was further purification by pre-HPLC (column: Welch Xtimate C18 150*30 mm*5 um; mobile phase: [water (10 mM NH₄HCO₃)-ACN]; B %: 5%-40%, 8 min) to give product as white solid. Compound Target 1 (0.085 g, 196 umol, 14.6% yield) was obtained as a light yellow solid.

¹H NMR: ET25189-16-p1a2 400 MHz MeOD

δ 8.42 (m, 1H), 7.58-7.61 (m, 3H), 7.51-7.56 (m, 2H), 7.35-7.50 (m, 1H), 4.43 (s, 1H), 4.23 (s, 1H), 3.77 (t, J=7.2 Hz, 1H), 3.62 (t, J=7.2 Hz, 1H), 3.43-3.45 (m, 1H), 3.34-3.36 (m, 1H), 2.67-2.69 (m, 1H), 2.61 (t, J=6.8 Hz, 1H), 1.58-1.69 (m, 2H), 0.93 (t, J=6.4 Hz, 3H).

LC-MS: ET25189-16-P1A1 (M+H⁺=434.1)

HPLC: ET25189-16-P1A1, RT=2.225

Example 3. Synthesis of Compounds 34 and 35

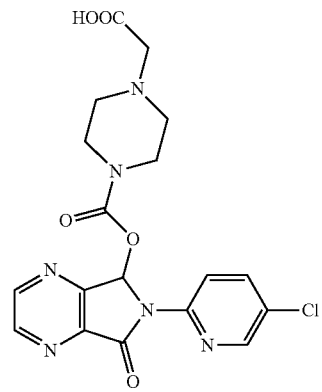

Scheme 9

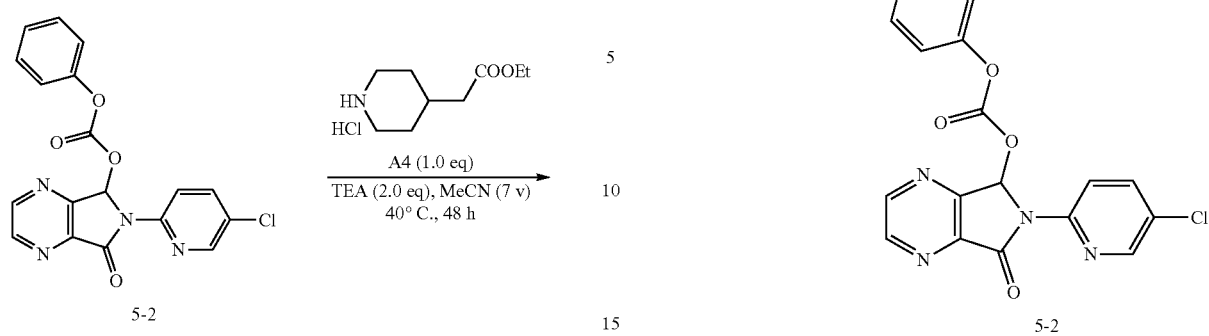

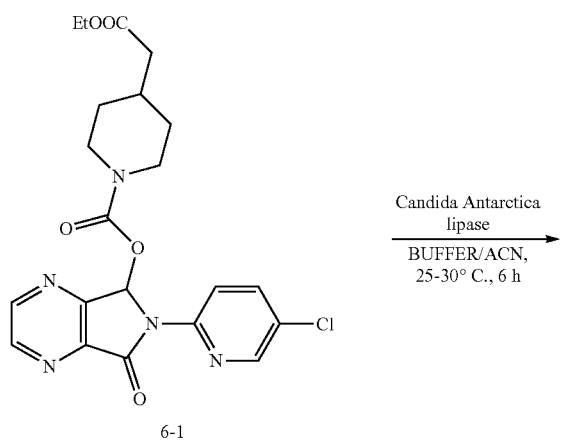

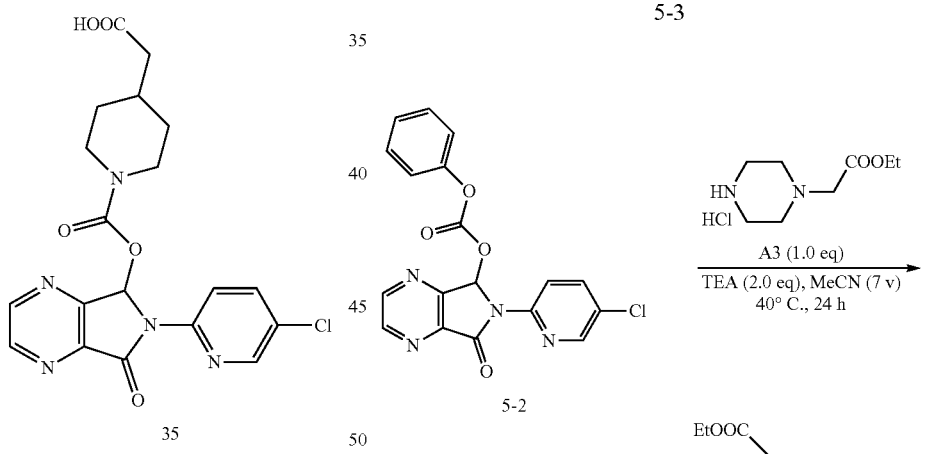

To a solution of compound 5-1 (500 mg, 1.90 mmol, 1.00 eq) and TEA (385 mg, 3.81 mmol, 530 uL, 2.00 eq) in DCM (5.00 mL) was added dropwise phenyl carbonochloridate (328 mg, 2.09 mmol, 262 uL, 1.10 eq) in DCM (2.00 mL) at 0-5° C. The reaction temperature was gradually raised to 20° C. and stirred for 3 h. TLC (Petroleum ether/Ethyl acetate=2/1, $R_f$=0.59) indicated compound 5-1 was consumed completely and one new spot formed. The reaction mixture was diluted with $H_2O$ (10 mL) and extracted with DCM (20 mL). The combined organic layers were washed with brine (5 mL), dried over $Na_2SO_4$, filtered and concentrated under reduced pressure to give a residue. Compound 5-2 (800 mg, crude) was obtained as a white solid, which was used into next step directly without purification further.

$^1$H NMR: ET25243-7-P1A 400 MHz DMSO-$d_6$

General Procedure for Preparation of Compound 5-3

General Procedure for Preparation of Compound 5-2

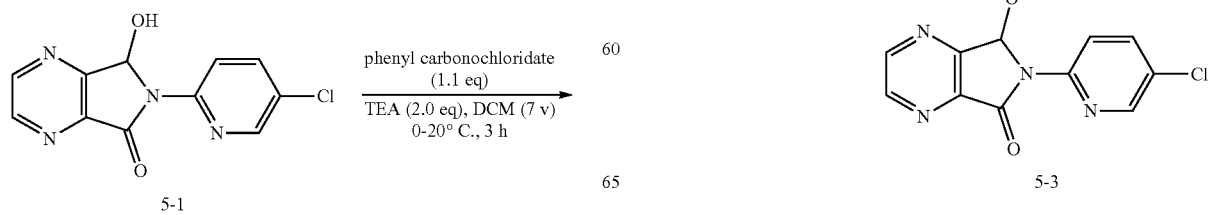

To a solution of compound 5-2 (400 mg, 1.05 mmol, 1.00 eq) in MeCN (5.00 mL) was added TEA (212 mg, 2.09 mmol, 291 uL, 2.00 eq) and compound A3 (218 mg, 1.05 mmol, 1.00 eq, HCl). The mixture was stirred at 40° C. for 24 h. TLC (Petroleum ether/Ethyl acetate=0/1, $R_f$=0.15) indicated ~5% of compound 5-2 was remained, and one major new spot with larger polarity was detected. The reaction mixture was concentrated under reduced pressure to give a residue. The residue was purified by column chromatography (SiO$_2$, Dichloromethane/Ethyl acetate=10/1 to 1/1). Compound 5-3 (200 mg, 434 umol, 41.5% yield) was obtained as a white solid.

$^1$H NMR: ET25243-8-P1A 400 MHz CDCl$_3$

δ 8.82 (d, J=2.4 Hz, 1H), 8.78 (d, J=2.4 Hz, 1H), 8.45 (d, J=8.8 Hz, 1H), 8.33 (d, J=2.8 Hz, 1H), 7.95 (s, 1H), 7.73 (dd, J=8.8, 2.8 Hz, 1H), 4.04-4.12 (m, 2H), 3.51-3.65 (m, 2H), 3.22 (br s, 2H), 3.12 (s, 2H), 2.54 (br s, 2H), 2.21-2.32 (m, 2H), 1.19 (t, J=6.8 Hz, 3H)

General Procedure for Preparation of Compound 34

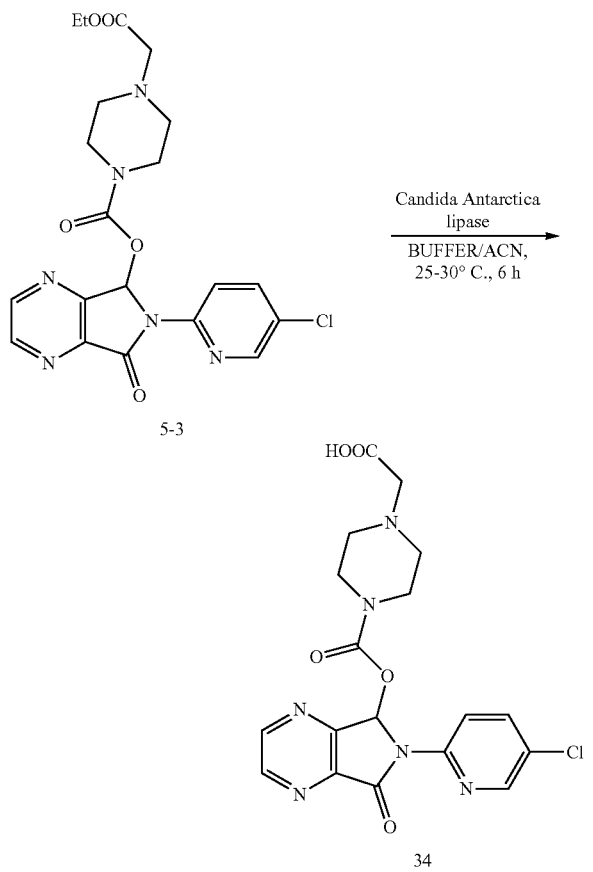

To a solution of *Candida Antarctica* lipase (0.4 g) in BUFFER (20 mL) (0.1 M phosphate buffer Ph=7) was added compound 5-3 (200 mg, 434 umol, 1.00 eq) in MeCN (2.00 mL) at 25° C. The mixture was stirred at 30° C. for 6 hrs. LC-MS (ET25243-10-P1A1, Rt=1.337 min) showed compound 5-3 was consumed completely and desired mass was detected. The reaction mixture was dissolved with MeOH and filtered through a celite pad, the filter cake was concentrated to give the residue. The residue was purified by prep-HPLC (column: Welch Xtimate C18 150*25 mm*5 um; mobile phase: [water (10 mM NH$_4$HCO$_3$)-ACN]; B %: 10%-40%, 10 min). Compound Target 5 (50 mg, 116 umol, 26.6% yield) was obtained as a light yellow solid.

$^1$H NMR: ET25243-10-P1A 400 MHz DMSO-d$_6$

δ 8.97 (dd, J=12.8, 2.4 Hz, 2H), 8.56 (d, J=2.4 Hz, 1H), 8.38 (d, J=9.2 Hz, 1H), 8.12 (dd, J=9.2, 2.8 Hz, 1H), 7.78 (s, 1H), 3.14 (br d, J=1.2 Hz, 3H), 2.98 (s, 2H), 2.75-2.80 (m, 1H), 2.32-2.34 (m, 2H), 2.22-2.31 (m, 1H), 2.03-2.14 (m, 1H)

LCMS: ET25243-10-P1A2, (M+1): 433.0

HPLC: ET25243-10-P1A2, RT=2.136

General Procedure for Preparation of Compound 6-1

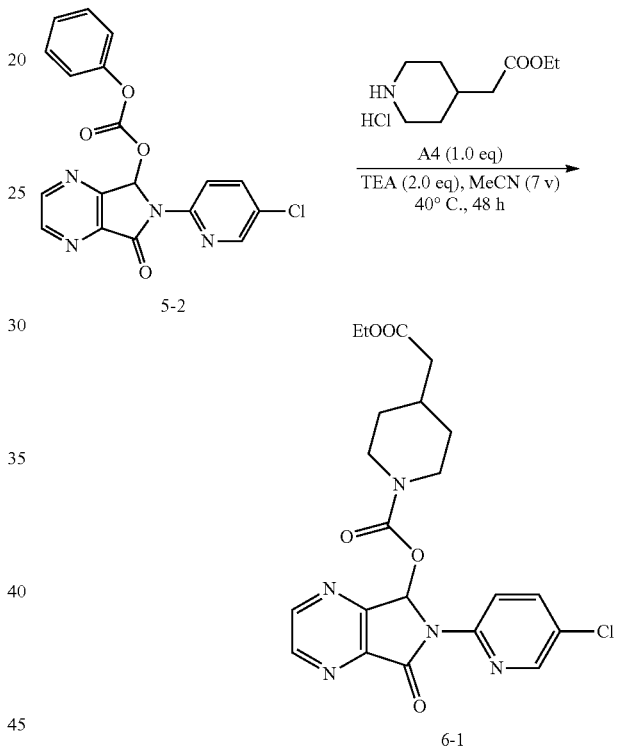

To a solution of compound 5-2 (400 mg, 1.05 mmol, 1.00 eq) in MeCN (5.00 mL) was added TEA (211 mg, 2.09 mmol, 291 uL, 2.00 eq) and compound A4 (217 mg, 1.05 mmol, 1.00 eq, HCl). The mixture was stirred at 40° C. for 48 h. TLC (Petroleum ether/Ethyl acetate=1/1, $R_f$=0.29) indicated ~5% of compound 5-2 was remained, and one major new spot with larger polarity was detected. The reaction mixture was concentrated under reduced pressure to give a residue. The residue was purified by column chromatography (SiO$_2$, Dichloromethane/Ethyl acetate=10/1 to 1/1). Compound 6-1 (300 mg, 652 umol, 62.4% yield) was obtained as a white solid.

$^1$H NMR: ET25243-9-P1A 400 MHz CDCl$_3$

δ 8.89-8.93 (m, 1H), 8.85-8.88 (m, 1H), 8.53 (br d, J=8.4 Hz, 1H), 8.39-8.43 (m, 1H), 8.05 (br s, 1H), 7.79-7.88 (m, 1H), 4.22-4.37 (m, 1H), 4.09-4.17 (m, 2H), 3.72-3.83 (m, 1H), 2.59-2.92 (m, 2H), 2.21 (br t, J=6.4 Hz, 2H), 1.87-1.98 (m, 1H), 1.72-1.84 (m, 1H), 1.48-1.60 (m, 1H), 1.22-1.31 (m, 4H), 0.66-1.08 (m, 1H)

General Procedure for Preparation of Compound 35

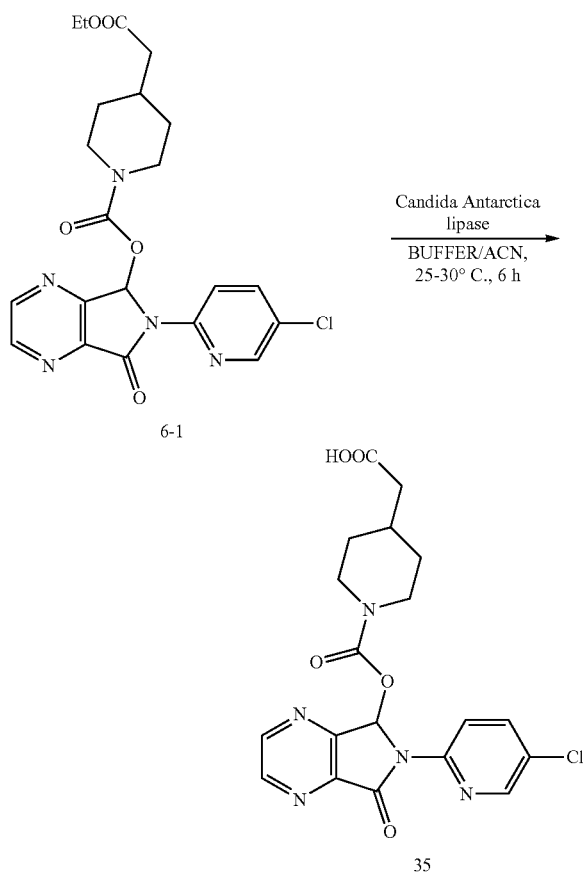

To a solution of *Candida Antarctica* lipase (400 mg) in BUFFER (20 mL) (0.1 M phosphate buffer pH=7) was added compound 6-1 (300 mg, 652 umol, 1.00 eq) in MeCN (2 mL) at 25° C. The mixture was stirred at 30° C. for 6 h. LC-MS (ET25243-11-P1A2, Rt=1.365 min) showed compound 6-1 was consumed completely and desired mass was detected. The reaction mixture was filtered through a celite pad and the filter cake was concentrated to give the residue. The residue was purified by prep-HPLC (column: Welch Xtimate C18 150*25 mm*5 um; mobile phase: [water (10 mM $NH_4HCO_3$)-ACN]; B %: 5%-35%, 10 min). Compound Target 6 (100 mg, 232 umol, 35.5% yield) was obtained as a yellow solid.

$^1$H NMR: ET25243-11-P1A3 400 MHz MeOD

δ 8.91 (dd, J=11.2, 2.8 Hz, 2H), 8.39-8.59 (m, 2H), 7.87-8.06 (m, 2H), 4.08-4.29 (m, 1H), 3.77-3.90 (m, 1H), 2.66-2.94 (m, 2H), 2.12-2.23 (m, 2H), 1.72-1.98 (m, 2H), 1.37-1.65 (m, 1H), 1.11-1.29 (m, 1H), 0.53-1.05 (m, 1H) LCMS: ET25243-11-P1A1 (M+1): 432.1 HPLC: ET25243-11-P1A1, RT=2.714

Example 4

Ligand-gated ion channels targeted were hGABAA α1β3γ2 and hGABAA α2β3γ2.

Electrophysiological assays conducted to profile nine (9) compounds for activities on the on channel targets listed above for Positive Allosteric Modulator (PAM) activities using the IonFlux HT electrophysiological platform. Test compound Isoguvacine exhibited agonist activity against GABAA targets in a previous study (US034-0003415) and as such, any apparent inhibition of $EC_{20}$ GABA-evoked currents is likely due to ion channel de-sensitization as opposed to true inhibition.

Test Compound Data Results for GABAA α1β3γ2
GABAA α1β3γ2: Plate A

Figure 2:
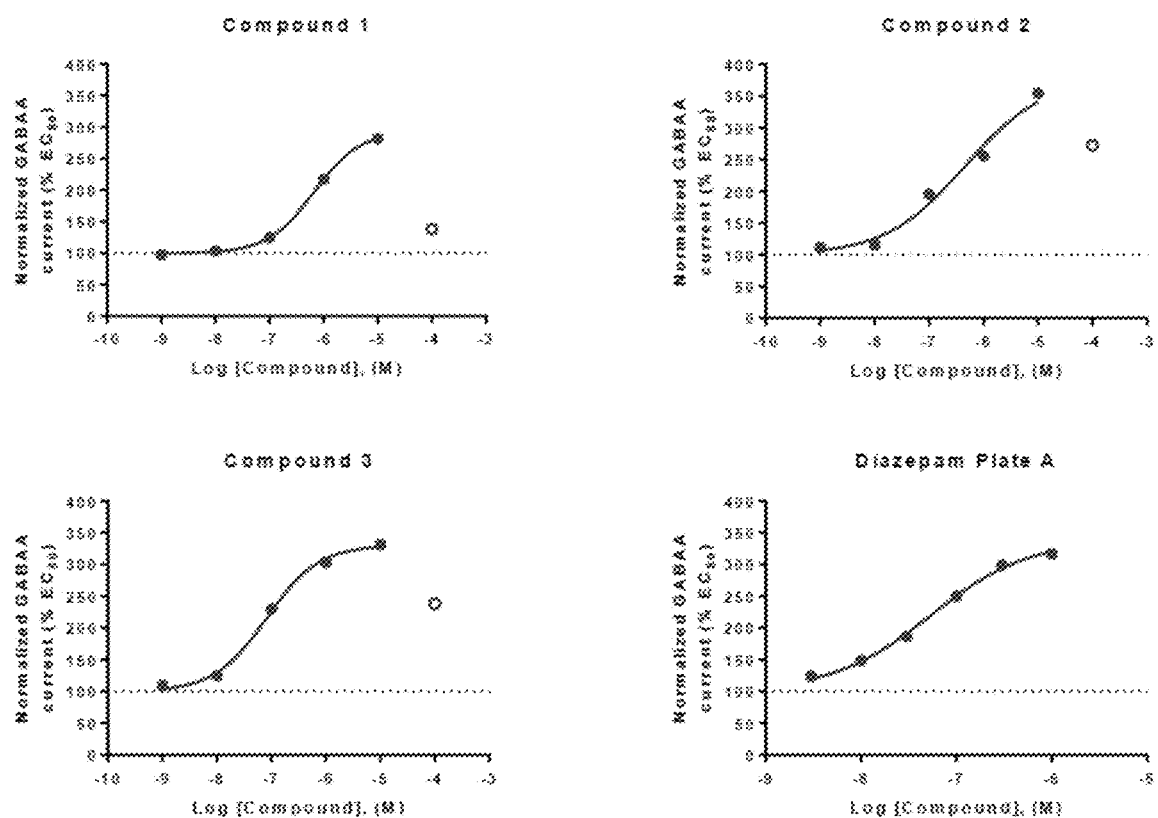
FIG. 2 shows the effects of compounds 1, 2, and 4 on the GABAA α1β3γ2 ion channel.

The effects of compounds on profiled ion channels are shown in FIG. 2. The parameters measured are described in the Data Analysis section. All compound response data has been normalized to the baseline peak current induced by addition of EC20 GABA for 2 seconds. Open circles represents data that has been excluded from the curve fitting.

TABLE 7

| Plate A: Target | Compound | Mean Maximal Effect (% of Control) | Estimated $EC_{50}$ |
|---|---|---|---|
| GABAA α1β3γ2 | Compound 1 | 282 | 654 nM |
|  | Compound 2 | 354 | 446 nM |
|  | Compound 3 | 331 | 81 nM |
|  | Diazepam | 317 | 54 nM |

GABAA α1β3γ2: Plate B

Figure 3:
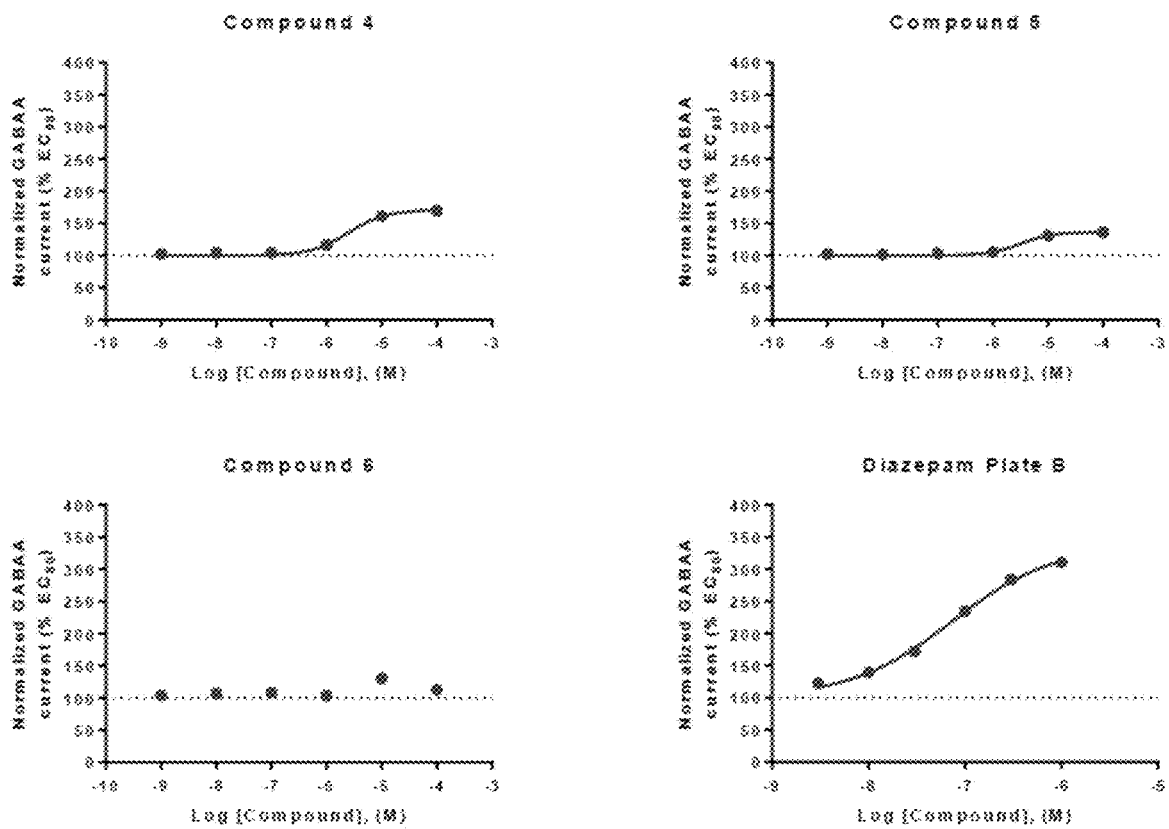
FIG. 3 shows the effects of compounds 4, 5, and 6 on the GABAA α1β3γ2 ion channel.

The effects of compounds on profiled ion channels are shown in FIG. 3. The parameters measured are described in the Data Analysis section. All compound response data has been normalized to the baseline peak current induced by addition of EC20 GABA for 2 seconds. Where no curve fit was possible, n/c (not calculable) is listed.

TABLE 8

| Plate B: Target | Compound | Mean Maximal Effect (% of Control) | Estimated $EC_{50}$ |
|---|---|---|---|
| GABAA α1β3γ2 | Compound 4 | 170 | 2.47 μM |
|  | Compound 5 | 136 | 3.16 μM |
|  | Compound 6 | 130 | n/c |
|  | Diazepam | 310 | 74 nM |

GABAA α1β3γ2: Plate C

Figure 4:
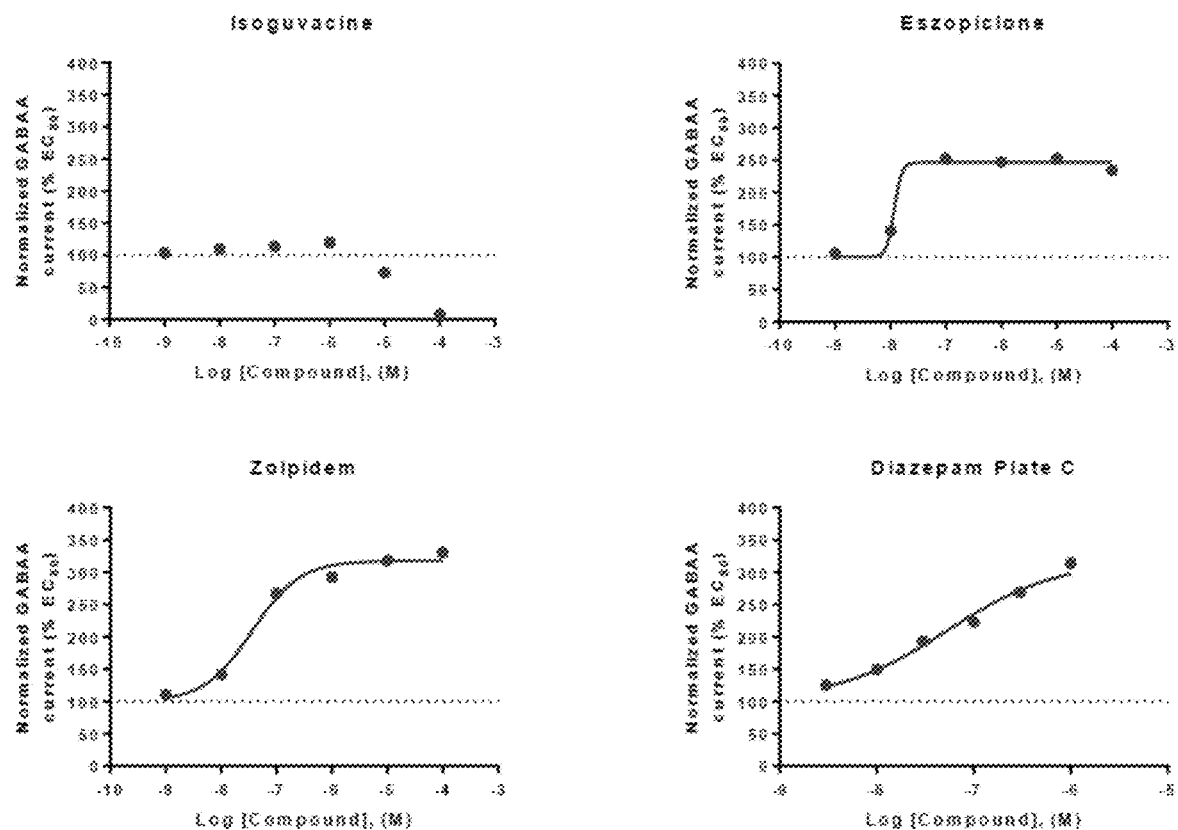
FIG. 4 shows the effects of isoguvacine, eszopiclone, zolpidem, and diazepam on the GABAA α1β3γ2 ion channel.

The effects of compounds on profiled ion channels are shown in FIG. 4. The parameters measured are described in the Data Analysis section. All compound response data has been normalized to the baseline peak current induced by addition of EC20 GABA for 2 seconds. Where no positive modulation EC50 curve fit was possible, n/c (not calculable) is listed.

TABLE 9

| Plate C: Target | Compound | Mean Maximal Effect (% of Control) | Estimated $EC_{50}$ |
|---|---|---|---|
| GABAA α1β3γ2 | Isoguvacine | 120 | n/c* |
|  | Eszopiclone | 252 | 12 nM |
|  | Zolpidem | 331 | 36 nM |
|  | Diazepam | 314 | 53 nM |

Test Compound Data Results for GABAA α2β3γ2 $GABA_A$ α2 3γ2: Plate A

Figure 5:
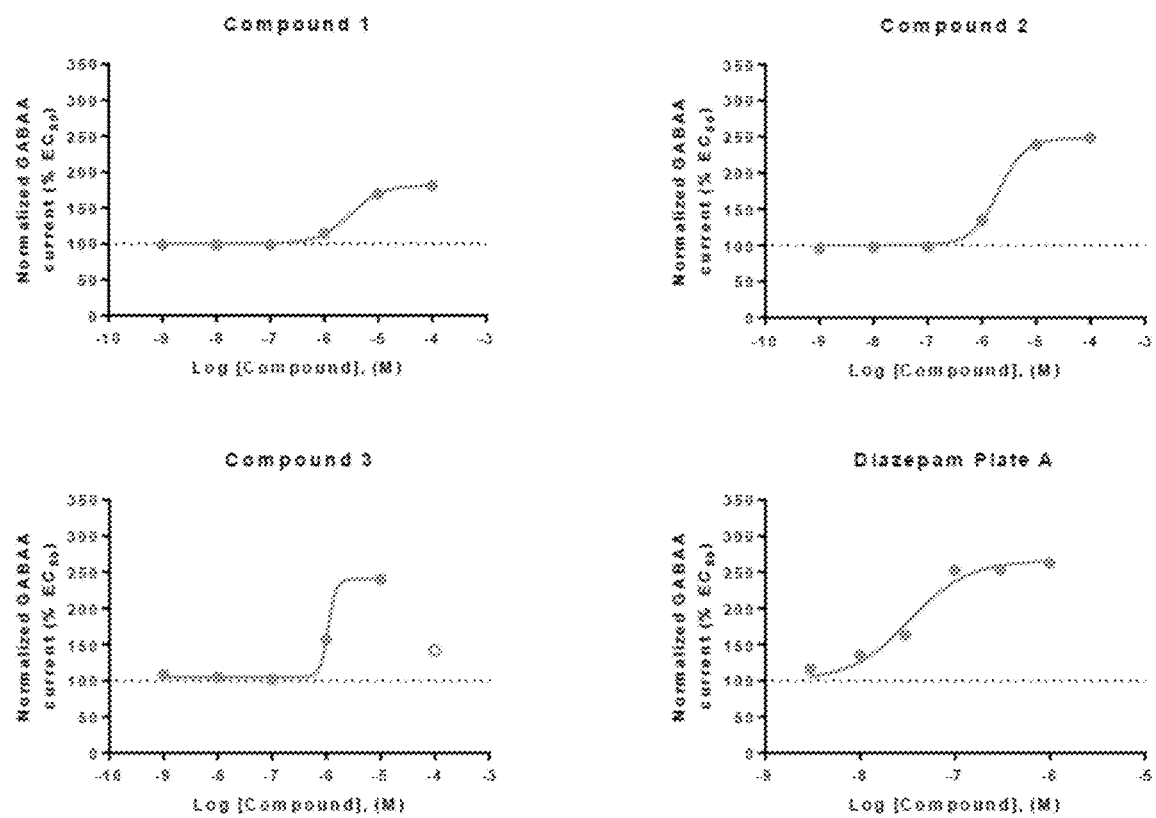
FIG. 5 shows the effects of compounds 1, 2, and 3 on the GABAA α2β3γ2 ion channel.

The effects of compounds on profiled ion channels are shown in FIG. 5. The parameters measured are described in the Data Analysis section. All compound response data has been normalized to the baseline peak current induced by addition of EC20 GABA for 2 seconds. Open circles represent data that has been excluded from the curve fitting. Where no curve fit was possible, n/c (not calculable) is listed.

TABLE 10

| Plate A: Target | Compound | Mean Maximal Effect (% of Control) | Estimated $EC_{50}$ |
|---|---|---|---|
| GABAA α2β3γ2 | Compound 1 | 181 | 3.0 μM |
| | Compound 2 | 248 | 2.0 μM |
| | Compound 3 | 240 | 1.1 μM |
| | Diazepam | 262 | 33 nM |

GABAA α2β3γ2: Plate B

Figure 6:
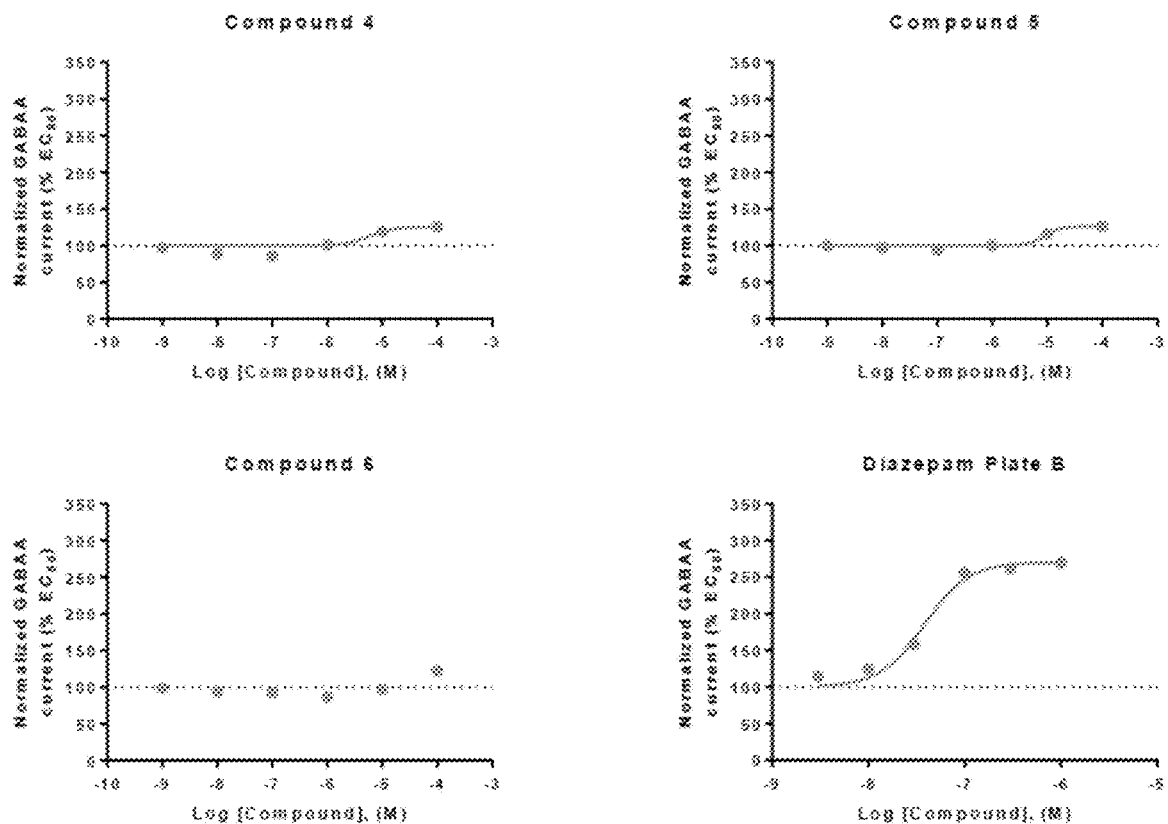
FIG. 6 shows the effects of compounds 4, 5, and 6 on the GABAA α2β3γ2 ion channel.
Figure 7:
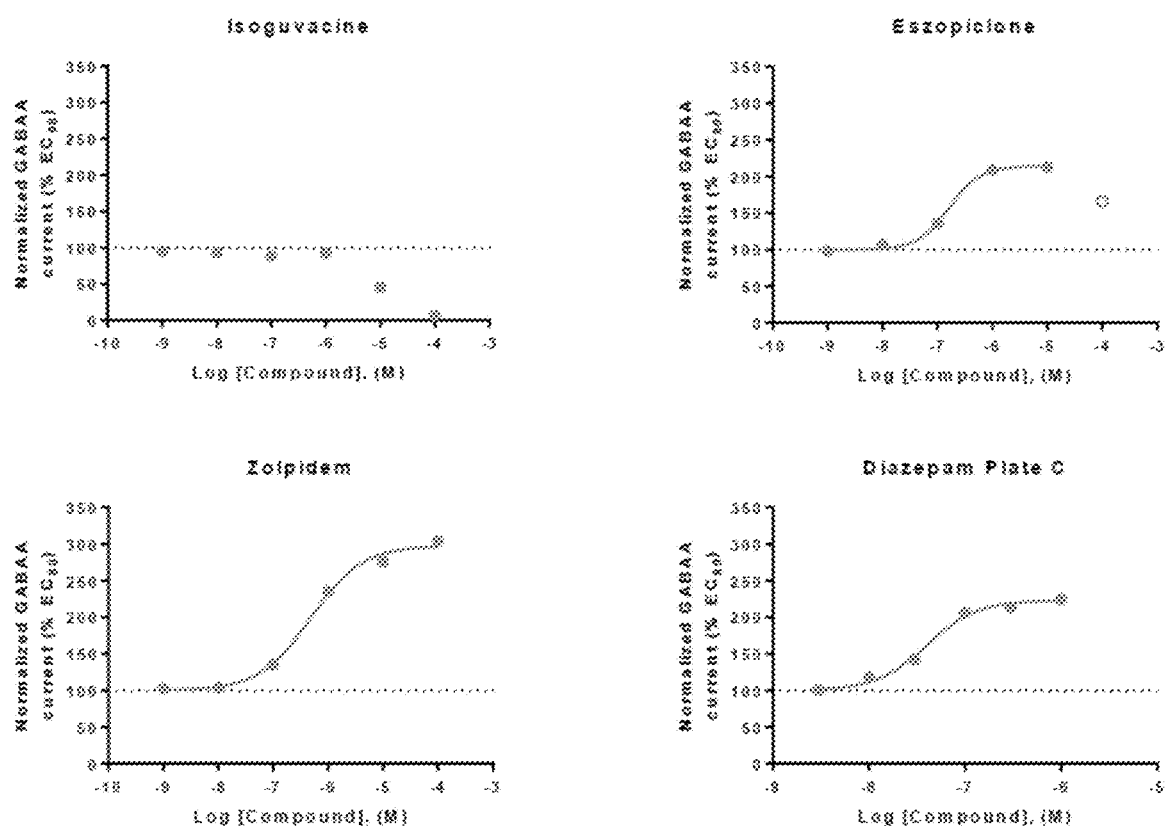
FIG. 7 shows the effects of isoguvacine, eszopiclone, zolpidem, and diazepam on the GABAA α2β3γ2 ion channel.

The effects of compounds on profiled ion channels are shown in FIG. 6. The parameters measured are described in the Data Analysis section. All compound response data has been normalized to the baseline peak current induced by addition of $EC_{20}$ GABA for 2 seconds. Where no curve fit was possible n/c (not calculable) is listed.

TABLE 11

| Plate B: Target | Compound | Mean Maximal Effect (% of Control) | Estimated $EC_{50}$ |
|---|---|---|---|
| GABAA α2β3γ2 | Compound 4 | 126 | 5.8 μM |
| | Compound 5 | 126 | 8.7 μM |
| | Compound 6 | 122 | n/c |
| | Diazepam | 269 | 38 nM |

GABAA α2β3γ2: Plate C

The effects of compounds on profiled ion channels are shown below. The parameters measured are described in the Data Analysis section. All compound response data has been normalized to the baseline peak current induced by addition of $EC_{20}$ GABA for 2 seconds. Open circles represent data that has been excluded from the curve fitting. Where no positive modulation $EC_{50}$ curve fit was possible, n/c* (not calculable) is listed.

TABLE 12

| Plate C: Target | Compound | Mean Maximal Effect (% of Control) | Estimated $EC_{50}$ |
|---|---|---|---|
| GABAA α2β3γ2 | Isoguvacine | 95 | n/c* |
| | Eszopiclone | 213 | 164 nM |
| | Zolpidem | 304 | 479 nM |
| | Diazepam | 224 | 40 nM |

Summary Data Tables

Tables 13 to 18 show the normalized peak current values for test compounds assayed against hGABAA ion channels. All compound response data has been normalized to the baseline peak current induced by addition $EC_{20}$ GABA for 2 seconds.

TABLE 13

α1β3γ2 Plate A.

| Compound | Concentration (μM) | (%) Control n1 | n2 | mean |
|---|---|---|---|---|
| Compound 1 | 0.001 | 98.9 | 96.0 | 97.5 |
| Compound 1 | 0.01 | 106.3 | 100.8 | 103.5 |
| Compound 1 | 0.1 | 128.7 | 120.2 | 124.4 |
| Compound 1 | 1 | 181.5 | 252.6 | 217.0 |
| Compound 1 | 10 | 224.9 | 338.6 | 281.7 |
| Compound 1 | 100 | 96.6 | 179.9 | 138.3 |
| Compound 2 | 0.001 | 110.2 | 112.0 | 111.1 |
| Compound 2 | 0.01 | 130.2 | 100.9 | 115.5 |
| Compound 2 | 0.1 | 212.6 | 178.0 | 195.3 |
| Compound 2 | 1 | 282.3 | 229.2 | 255.7 |
| Compound 2 | 10 | 378.3 | 330.6 | 354.4 |
| Compound 2 | 100 | 304.7 | 240.1 | 272.4 |
| Compound 3 | 0.001 | 101.3 | 117.4 | 109.3 |
| Compound 3 | 0.01 | 113.0 | 135.8 | 124.4 |
| Compound 3 | 0.1 | 204.8 | 254.9 | 229.8 |
| Compound 3 | 1 | 300.1 | 306.4 | 303.2 |
| Compound 3 | 10 | 330.9 | 331.8 | 331.3 |
| Compound 3 | 100 | 226.2 | 249.9 | 238.1 |
| Time matched Control Plate A | 1 | 109.9 | 101.1 | 105.5 |
| Time matched Control Plate A | 2 | 114.2 | 95.9 | 105.1 |
| Time matched Control Plate A | 3 | 120.6 | 93.3 | 106.9 |
| Diazepam Plate A | 0.003 | 123.6 | 124.3 | 124.0 |
| Diazepam Plate A | 0.01 | 149.5 | 147.2 | 148.4 |
| Diazepam Plate A | 0.03 | 182.7 | 190.3 | 186.5 |
| Diazepam Plate A | 0.1 | 230.0 | 269.9 | 250.0 |
| Diazepam Plate A | 0.3 | 265.9 | 331.8 | 298.9 |
| Diazepam Plate A | 1 | 284.9 | 349.1 | 317.0 |

TABLE 14

α1β3γ2 Plate B.

| Compound | Concentration (μM) | (%) Control n1 | n2 | mean |
|---|---|---|---|---|
| Compound 4 | 0.001 | 100.6 | 104.3 | 102.5 |
| Compound 4 | 0.01 | 101.7 | 106.5 | 104.1 |
| Compound 4 | 0.1 | 102.1 | 106.0 | 104.0 |
| Compound 4 | 1 | 120.1 | 112.9 | 116.5 |
| Compound 4 | 10 | 153.7 | 168.7 | 161.2 |
| Compound 4 | 100 | 155.8 | 184.1 | 170.0 |
| Compound 5 | 0.001 | 101.5 | 103.4 | 102.4 |
| Compound 5 | 0.01 | 100.7 | 103.0 | 101.9 |
| Compound 5 | 0.1 | 101.5 | 105.5 | 103.5 |
| Compound 5 | 1 | 104.0 | 106.7 | 105.4 |
| Compound 5 | 10 | 139.7 | 122.5 | 131.1 |
| Compound 5 | 100 | 141.8 | 130.7 | 136.2 |
| Compound 6 | 0.001 | 105.4 | 102.5 | 103.9 |
| Compound 6 | 0.01 | 107.8 | 105.9 | 106.8 |
| Compound 6 | 0.1 | 106.5 | 110.3 | 108.4 |
| Compound 6 | 1 | 103.0 | 104.3 | 103.7 |
| Compound 6 | 10 | 131.4 | 128.8 | 130.1 |
| Compound 6 | 100 | 110.9 | 114.6 | 112.8 |
| Time matched Control Plate B | 1 | 108.1 | 108.4 | 108.3 |
| Time matched Control Plate B | 2 | 109.2 | 108.6 | 108.9 |
| Time matched Control Plate B | 3 | 109.7 | 110.9 | 110.3 |
| Diazepam Plate B | 0.003 | 125.3 | 119.9 | 122.6 |
| Diazepam Plate B | 0.01 | 141.4 | 137.8 | 139.6 |
| Diazepam Plate B | 0.03 | 182.4 | 161.2 | 171.8 |
| Diazepam Plate B | 0.1 | 227.4 | 241.8 | 234.6 |
| Diazepam Plate B | 0.3 | 275.1 | 293.6 | 284.3 |
| Diazepam Plate B | 1 | 296.1 | 324.7 | 310.4 |

TABLE 15

α1β3γ2 Plate C.

| Compound | Concentration (μM) | (%) Control n1 | n2 | mean |
|---|---|---|---|---|
| Isoguvacine | 0.001 | 99.0 | 108.2 | 103.6 |
| Isoguvacine | 0.01 | 108.8 | 110.8 | 109.8 |
| Isoguvacine | 0.1 | 110.0 | 117.4 | 113.7 |
| Isoguvacine | 1 | 124.5 | 115.2 | 119.8 |
| Isoguvacine | 10 | 76.1 | 69.9 | 73.0 |
| Isoguvacine | 100 | 7.6 | 8.3 | 8.0 |
| Eszopiclone | 0.001 | 97.8 | 113.5 | 105.7 |
| Eszopiclone | 0.01 | 132.0 | 148.7 | 140.3 |
| Eszopiclone | 0.1 | 242.3 | 262.5 | 252.4 |
| Eszopiclone | 1 | 267.4 | 227.7 | 247.6 |
| Eszopiclone | 10 | 262.3 | 242.5 | 252.4 |
| Eszopiclone | 100 | 258.5 | 210.8 | 234.7 |
| Zolpidem | 0.001 | 116.2 | 105.2 | 110.7 |
| Zolpidem | 0.01 | 144.3 | 139.4 | 141.9 |
| Zolpidem | 0.1 | 278.5 | 256.1 | 267.3 |
| Zolpidem | 1 | 294.8 | 290.1 | 292.4 |
| Zolpidem | 10 | 326.1 | 310.1 | 318.1 |
| Zolpidem | 100 | 349.7 | 311.6 | 330.6 |
| Time matched Control Plate C | 1 | 106.4 | 97.7 | 102.1 |
| Time matched Control Plate C | 2 | 102.0 | 88.7 | 95.4 |
| Time matched Control Plate C | 3 | 109.4 | 90.3 | 99.8 |
| Diazepam Plate C | 0.003 | 121.6 | 129.0 | 125.3 |
| Diazepam Plate C | 0.01 | 137.2 | 162.2 | 149.7 |
| Diazepam Plate C | 0.03 | 169.0 | 217.4 | 193.2 |
| Diazepam Plate C | 0.1 | 232.1 | 214.1 | 223.1 |
| Diazepam Plate C | 0.3 | 262.8 | 275.8 | 269.3 |
| Diazepam Plate C | 1 | 284.8 | 343.8 | 314.3 |

TABLE 16

α2β3γ2 Plate A.

| Compound | Concentration (μM) | (%) Control n1 | n2 | mean |
|---|---|---|---|---|
| Compound 1 | 0.001 | 97.7 | 99.5 | 98.6 |
| Compound 1 | 0.01 | 95.9 | 100.6 | 98.2 |
| Compound 1 | 0.1 | 97.9 | 97.8 | 97.9 |
| Compound 1 | 1 | 114.5 | 113.0 | 113.8 |
| Compound 1 | 10 | 151.2 | 186.9 | 169.1 |
| Compound 1 | 100 | 174.4 | 187.5 | 181.0 |
| Compound 2 | 0.001 | 95.9 | 95.1 | 95.5 |
| Compound 2 | 0.01 | 96.3 | 97.5 | 96.9 |
| Compound 2 | 0.1 | 96.6 | 99.8 | 98.2 |
| Compound 2 | 1 | 128.4 | 140.3 | 134.4 |
| Compound 2 | 10 | 220.2 | 258.1 | 239.2 |
| Compound 2 | 100 | 242.6 | 253.4 | 248.0 |
| Compound 3 | 0.001 | 92.9 | 123.3 | 108.1 |
| Compound 3 | 0.01 | 97.8 | 112.0 | 104.9 |
| Compound 3 | 0.1 | 101.9 | 101.5 | 101.7 |
| Compound 3 | 1 | 160.5 | 153.1 | 156.8 |
| Compound 3 | 10 | 246.6 | 234.1 | 240.3 |
| Compound 3 | 100 | 146.2 | 137.8 | 142.0 |
| Time matched Control Plate A | 1 | 102.0 | 93.1 | 97.5 |
| Time matched Control Plate A | 2 | 91.0 | 97.4 | 94.2 |
| Time matched Control Plate A | 3 | 94.7 | 103.3 | 99.0 |
| Diazepam Plate A | 0.003 | 113.8 | 118.1 | 116.0 |
| Diazepam Plate A | 0.01 | 131.2 | 139.3 | 135.3 |
| Diazepam Plate A | 0.03 | 155.2 | 169.9 | 162.5 |
| Diazepam Plate A | 0.1 | 261.1 | 243.8 | 252.4 |
| Diazepam Plate A | 0.3 | 267.8 | 239.3 | 253.5 |
| Diazepam Plate A | 1 | 274.0 | 250.6 | 262.3 |

TABLE 17

α2β3γ2 Plate B.

| Compound | Concentration (μM) | (%) Control n1 | n2 | mean |
|---|---|---|---|---|
| Compound 4 | 0.001 | 93.0 | 100.8 | 96.9 |
| Compound 4 | 0.01 | 91.3 | 87.0 | 89.2 |
| Compound 4 | 0.1 | 86.9 | 84.3 | 85.6 |
| Compound 4 | 1 | 104.2 | 97.8 | 101.0 |
| Compound 4 | 10 | 122.1 | 116.3 | 119.2 |
| Compound 4 | 100 | 128.1 | 122.9 | 125.5 |
| Compound 5 | 0.001 | 98.5 | 101.1 | 99.8 |
| Compound 5 | 0.01 | 93.0 | 101.0 | 97.0 |
| Compound 5 | 0.1 | 87.1 | 100.4 | 93.7 |
| Compound 5 | 1 | 100.4 | 99.7 | 100.0 |
| Compound 5 | 10 | 113.3 | 118.3 | 115.8 |
| Compound 5 | 100 | 120.9 | 131.3 | 126.1 |
| Compound 6 | 0.001 | 103.2 | 93.7 | 98.5 |
| Compound 6 | 0.01 | 93.3 | 94.5 | 93.9 |
| Compound 6 | 0.1 | 91.8 | 92.8 | 92.3 |
| Compound 6 | 1 | 92.8 | 80.8 | 86.8 |
| Compound 6 | 10 | 103.1 | 90.1 | 96.6 |
| Compound 6 | 100 | 120.6 | 123.3 | 121.9 |
| Time matched Control Plate B | 1 | 97.9 | 92.9 | 95.4 |
| Time matched Control Plate B | 2 | 93.5 | 87.1 | 90.3 |
| Time matched Control Plate B | 3 | 91.3 | 90.6 | 90.9 |
| Diazepam Plate B | 0.003 | 112.4 | 117.2 | 114.8 |
| Diazepam Plate B | 0.01 | 123.3 | 124.7 | 124.0 |
| Diazepam Plate B | 0.03 | 156.2 | 160.3 | 158.2 |
| Diazepam Plate B | 0.1 | 261.6 | 249.9 | 255.8 |
| Diazepam Plate B | 0.3 | 260.9 | 262.3 | 261.6 |
| Diazepam Plate B | 1 | 285.9 | 252.8 | 269.3 |

TABLE 18

α2β3γ2 Plate C.

| Client Compound ID | Concentration (μM) | (%) Control n1 | n2 | mean |
|---|---|---|---|---|
| Isoguvacine | 0.001 | 94.5 | 96.3 | 95.4 |
| Isoguvacine | 0.01 | 90.4 | 96.0 | 93.2 |
| Isoguvacine | 0.1 | 85.9 | 91.8 | 88.9 |
| Isoguvacine | 1 | 95.4 | 89.3 | 92.3 |
| Isoguvacine | 10 | 55.0 | 36.4 | 45.7 |
| Isoguvacine | 100 | 8.4 | 5.3 | 6.9 |
| Eszopiclone | 0.001 | 101.6 | 94.1 | 97.9 |
| Eszopiclone | 0.01 | 112.9 | 100.7 | 106.8 |
| Eszopiclone | 0.1 | 141.4 | 130.7 | 136.0 |
| Eszopiclone | 1 | 203.1 | 214.2 | 208.7 |
| Eszopiclone | 10 | 210.0 | 215.8 | 212.9 |
| Eszopiclone | 100 | 167.0 | 164.5 | 165.8 |
| Zolpidem | 0.001 | 101.0 | 104.3 | 102.6 |
| Zolpidem | 0.01 | 98.9 | 107.9 | 103.4 |
| Zolpidem | 0.1 | 126.1 | 143.4 | 134.8 |
| Zolpidem | 1 | 237.4 | 233.9 | 235.6 |
| Zolpidem | 10 | 280.7 | 271.3 | 276.0 |
| Zolpidem | 100 | 310.6 | 297.6 | 304.1 |
| Time matched Control Plate C | 1 | 95.9 | 98.3 | 97.1 |
| Time matched Control Plate C | 2 | 90.3 | 96.3 | 93.3 |
| Time matched Control Plate C | 3 | 87.9 | 94.8 | 91.4 |
| Diazepam Plate C | 0.003 | 113.2 | 87.7 | 100.4 |
| Diazepam Plate C | 0.01 | 122.4 | 113.8 | 118.1 |
| Diazepam Plate C | 0.03 | 150.5 | 134.2 | 142.3 |
| Diazepam Plate C | 0.1 | 216.8 | 195.1 | 206.0 |
| Diazepam Plate C | 0.3 | 230.4 | 197.8 | 214.1 |
| Diazepam Plate C | 1 | 235.0 | 213.6 | 224.3 |

Materials and Methods

Compound Plate Preparation

The supplied compounds were prepared in DMSO to concentrations that were 300× the final assay concentration(s) Aliquots were taken out and diluted 300× into external buffer to give the final assay concentration. All wells included a final DMSO concentration of 0.33% including all control wells.

| Ion Channel | $EC_{20}$ Control & Concentration |
|---|---|
| hGABAA α1β3γ2 | 1 μM GABA |
| hGABAA α2β3γ2 | 0.8 μM GABA |

| Ion Channel | Positive Control (Reference PAM) |
|---|---|
| hGABAA α1β3γ2 | 0.003, 0.01, 0.03, 0.1, 0.3, 1 μM Diazepam |
| hGABAA α2β3γ2 | 0.003, 0.01, 0.03, 0.1, 0.3, 1 μM Diazepam |

Electrophysiological Recording Solutions

TABLE 19

External Recording Solution [mM].

| NaCl | 137 | KF | 70 |
|---|---|---|---|
| KCl | 4 | KCl | 60 |
| MgCl$_2$ | 1 | NaCl | 15 |
| CaCl$_2$ | 1.8 | HEPES | 5 |
| HEPES | 10 | EGTA | 5 |
| Glucose | 10 | MgATP | 4 | pH 7.35 (titrated with NaOH)

Experimental Protocols & Data Analysis
hGABAA IonFlux HT PAM Assay Schematic All recordings were obtained from a holding potential of −60 mV. The compound addition sequence that was used for all additions was the same for all assays. One addition of the $EC_{20}$ concentration of GABA was added to establish baseline response. Each test concentration of compound was applied for 30 seconds followed by the addition of $EC_{20}$ GABA in the presence of the compound for 2 seconds. The process was repeated with the next ascending concentration of test compound (FIG. 1).

hGABAA IonFlux HT PAM Assay Data Analysis

Peak inward currents in response to the GABA additions in the presence of a single concentration of compound were measured. All compound data have been normalized to the baseline peak current induced by addition of EC20 GABA for 2 seconds:

$$\text{Normalized Peak Current} = (I^{Compound+GABA}/I^{GABA})$$

Where I (Compound+GABA) is the peak current induced by addition of test compound+$EC_{20}$ GABA after 30 seconds incubation of test compound, I GABA is the baseline peak current induced by addition of $EC_{20}$ GABA. All data were first exported to an Excel compatible data file and then analyzed using Graph Pad Prism software.

TABLE 20

IonChannelProfiler Data Filters.

| Data Filter | Platform | Criteria |
|---|---|---|
| Rm | IonFlux HT | >60 MΩ |
| Current Amplitude | IonFlux HT | >1000 pA |

Example 5

Ligand-gated ion channel targets were hGABAA α2β3γ2 and hGABAA α1β3γ2. Electrophysiological assays conducted to profile two compounds for agonist activities on hGABAA α2β3γ2 and seven compounds for agonist activities on hGABAA α1β3γ2 using the IonFlux HT electrophysiological platform.

Compound 1, 2, 3, 4, 5, and 6 did not activate hGABAA α1β3γ2 ion channel currents at 0:3, 1, 3, 10, 30, 100, 300 and 10001 μM concentrations. Isoguvacine activated hGABAA α1β3γ2 ion channel currents with an $EC_{50}$ value of 19.7 μM.

Results

Test Compound Data Results—GABAA α1β3γ2 Agonist Assay

Figure 8:
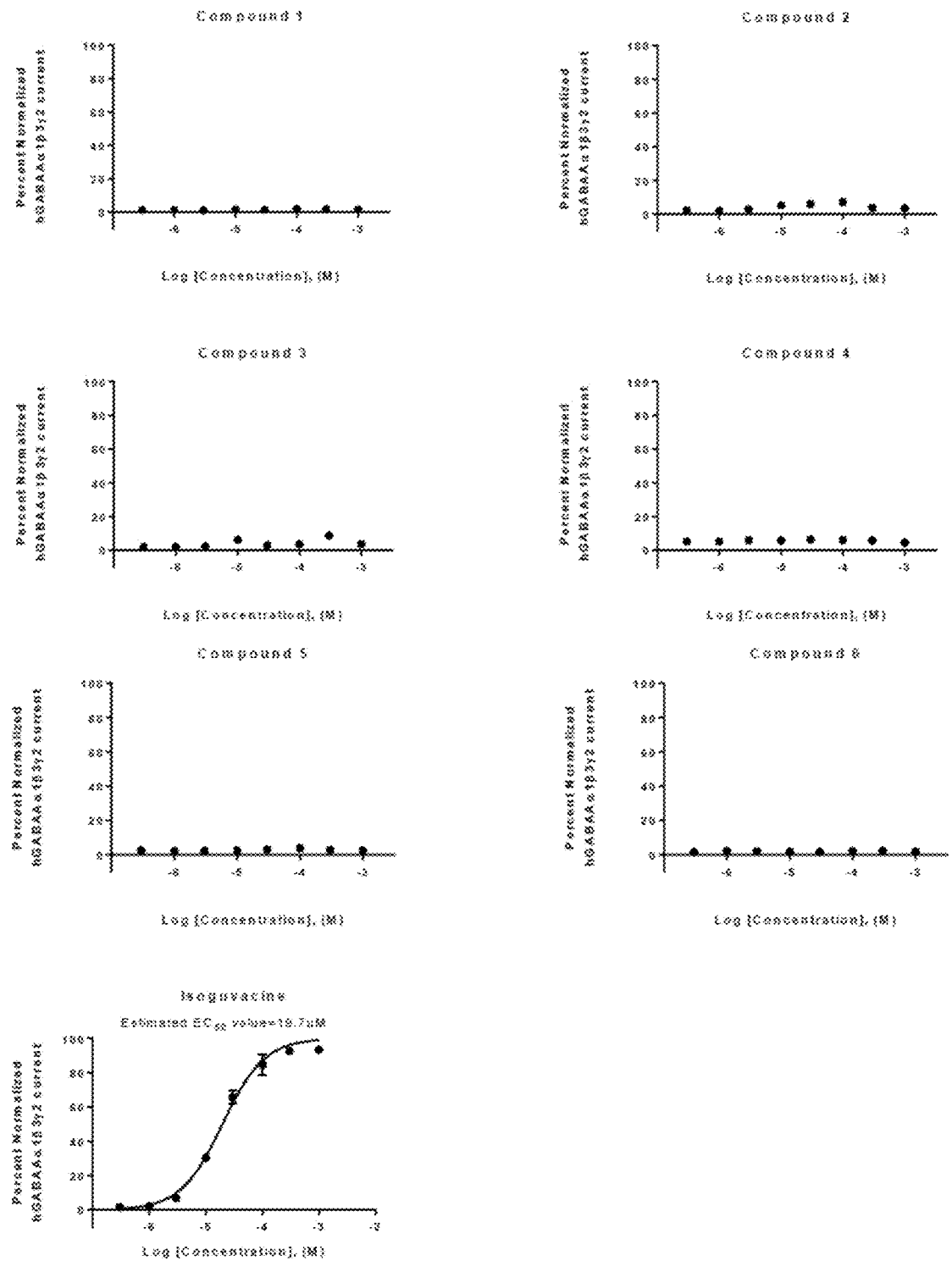
FIG. 8 shows the effects of six compounds and Isoguvacine on hGABAA α1β3γ2 ion channels.

The effects of six compounds and Isoguvacine on hGABAA α1β3γ2 ion channels are shown in FIG. 8. The parameters measured are described in the Data Analysis section. All compound response data has been normalized to the baseline peak current induced by addition of $EC_{100}$ GABA (30 μM) for 2 seconds for the agonist assay. Note: The test compounds was applied over two (2) 'experimental patterns' in increasing concentrations.

hGABAA α1β3γ2 Agonist Assay

Table 21 shows the normalized peak current values for each compound assayed against hGABAA α1β3γ2 ion channels. GABA was used as the reference compound for the Agonist assay.

TABLE 21

| Compound | Concentration (μM) | Estimated EC50 (μM) | Normalized Percentage Activation Mean | SEM | n |
|---|---|---|---|---|---|
| Compound 1 | 0.3 | >1000 | 1.64 | 0.21 | 4 |
| Compound 1 | 1 | | 1.39 | 0.30 | 4 |
| Compound 1 | 3 | | 2.34 | 0.35 | 4 |
| Compound 1 | 10 | | 6.52 | 1.19 | 4 |
| Compound 1 | 30 | | 4.78 | 0.96 | 4 |
| Compound 1 | 100 | | 6.97 | 0.70 | 4 |
| Compound 1 | 300 | | 7.15 | 1.07 | 4 |
| Compound 1 | 10000 | | 4.98 | 0.80 | 4 |
| Compound 2 | 0.3 | >1000 | 2.17 | 0.66 | 4 |
| Compound 2 | 1 | | 1.99 | 0.35 | 4 |
| Compound 2 | 3 | | 2.79 | 0.38 | 4 |
| Compound 2 | 10 | | 5.37 | 1.55 | 4 |
| Compound 2 | 30 | | 5.93 | 1.75 | 4 |
| Compound 2 | 100 | | 7.10 | 0.66 | 4 |
| Compound 2 | 300 | | 3.63 | 0.49 | 4 |
| Compound 2 | 10000 | | 3.48 | 0.37 | 4 |
| Compound 3 | 0.3 | >1000 | 1.99 | 0.23 | 3 |
| Compound 3 | 1 | | 1.90 | 0.14 | 3 |
| Compound 3 | 3 | | 2.32 | 0.38 | 3 |
| Compound 3 | 10 | | 6.30 | 1.19 | 3 |
| Compound 3 | 30 | | 2.98 | 0.32 | 3 |
| Compound 3 | 100 | | 3.63 | 0.78 | 3 |
| Compound 3 | 300 | | 8.78 | 0.50 | 4 |
| Compound 3 | 10000 | | 3.53 | 0.59 | 4 |
| Compound 4 | 0.3 | >1000 | 5.26 | 1.81 | 4 |
| Compound 4 | 1 | | 5.13 | 1.85 | 4 |
| Compound 4 | 3 | | 5.89 | 2.03 | 4 |
| Compound 4 | 10 | | 5.68 | 1.95 | 4 |
| Compound 4 | 30 | | 6.45 | 1.79 | 4 |
| Compound 4 | 100 | | 5.97 | 1.73 | 4 |
| Compound 4 | 300 | | 5.85 | 0.85 | 4 |
| Compound 4 | 10000 | | 4.45 | 0.36 | 4 |
| Compound 5 | 0.3 | >1000 | 2.54 | 0.85 | 4 |
| Compound 5 | 1 | | 2.02 | 0.64 | 4 |
| Compound 5 | 3 | | 2.28 | 0.96 | 4 |
| Compound 5 | 10 | | 2.45 | 0.82 | 4 |
| Compound 5 | 30 | | 3.08 | 0.92 | 4 |

TABLE 21-continued

| Compound | Concentration (μM) | Estimated EC50 (μM) | Normalized Percentage Activation Mean | SEM | n |
|---|---|---|---|---|---|
| Compound 5 | 100 | | 3.75 | 0.70 | 4 |
| Compound 5 | 300 | | 2.70 | 0.25 | 4 |
| Compound 5 | 10000 | | 2.38 | 0.28 | 4 |
| Compound 6 | 0.3 | >1000 | 1.59 | 0.30 | 4 |
| Compound 6 | 1 | | 2.06 | 0.30 | 4 |
| Compound 6 | 3 | | 1.90 | 0.26 | 4 |
| Compound 6 | 10 | | 1.89 | 0.33 | 4 |
| Compound 6 | 30 | | 1.74 | 0.26 | 4 |
| Compound 6 | 100 | | 1.95 | 0.15 | 4 |
| Compound 6 | 300 | | 2.19 | 0.40 | 4 |
| Compound 6 | 10000 | | 2.08 | 0.39 | 4 |
| Isoguvacine | 0.3 | 19.7 | 1.61 | 0.35 | 6 |
| Isoguvacine | 1 | | 2.18 | 0.48 | 6 |
| Isoguvacine | 3 | | 6.83 | 0.92 | 6 |
| Isoguvacine | 10 | | 30.46 | 1.51 | 6 |
| Isoguvacine | 30 | | 65.63 | 4.01 | 6 |
| Isoguvacine | 100 | | 84.77 | 6.11 | 6 |
| Isoguvacine | 300 | | 92.72 | 1.00 | 6 |
| Isoguvacine | 10000 | | 93.46 | 2.08 | 6 |
| GABA | 0.1 | 17.3 | 3.79 | 0.67 | 4 |
| GABA | 0.3 | | 7.43 | 0.71 | 4 |
| GABA | 1 | | 28.12 | 2.69 | 4 |
| GABA | 3 | | 70.65 | 2.73 | 4 |
| GABA | 10 | | 97.60 | 2.44 | 4 |
| GABA | 30 | | 100.00 | 0.00 | 4 |
| Time-matched vehicle control | Vehicle 1 | | 1.28 | 0.18 | 4 |
| Time-matched vehicle control | Vehicle 2 | | 1.26 | 0.17 | 4 |
| Time-matched vehicle control | Vehicle 3 | | 1.02 | 0.11 | 4 |
| Time-matched vehicle control | Vehicle 4 | | 1.18 | 0.12 | 4 |
| Time-matched vehicle control | Vehicle 5 | | 1.49 | 0.25 | 4 |
| Time-matched vehicle control | Vehicle 6 | | 1.15 | 0.14 | 4 |

GABAA α1β3γ2 Agonist Assay

Figure 9:
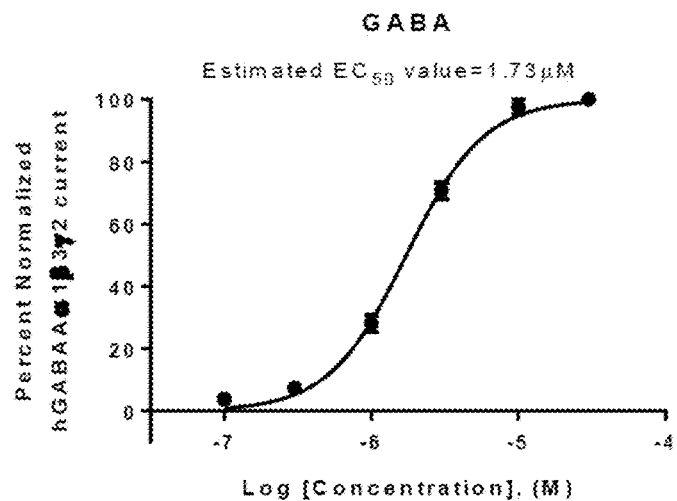
FIG. 9 shows data for six (6) point concentration response of GABA tested to serve as a positive control for the Agonist assay.
Figure 10:
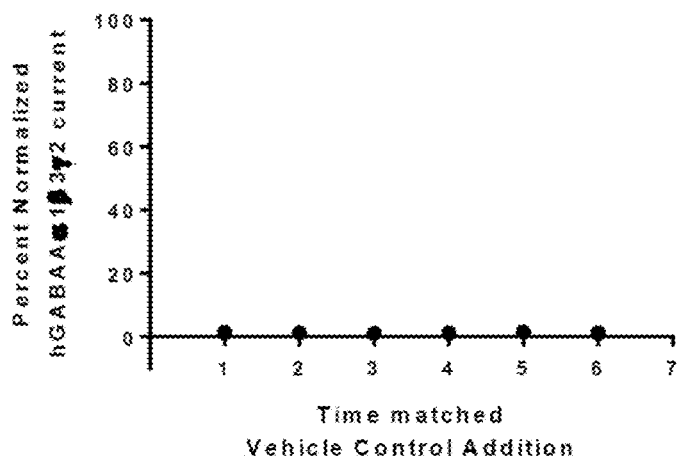
FIG. 10 shows data for six (6) additions of vehicle control for 2 seconds introduced to the cells to act as a time matched control for agonist assay.

Six (6) point concentration response of GABA was tested to serve as a positive control for the Agonist assay (FIG. 9). Six (6) additions of vehicle control for 2 seconds were introduced to the cells to act as a time matched control for agonist assay; the data are shown in FIG. 10. Note: The test compounds were applied over two (2) 'experimental patterns' in increasing concentrations.

Materials and Methods

Compound Plate Preparation

The supplied compound was prepared in DMSO to concentrations that were 300× the final assay concentrations. Aliquots were taken out and diluted 300× into external buffer to give the final assay concentration. At wells included a final DMSO concentration of 0.33% including all control wets. At compounds were fully soluble in external buffer by visual inspection,
  Ion Channel Positive Control (Reference Agonist)
  hGABAA α2β3γ2 30, 10, 3, 1, 0.3, and 0.1 μM GABA
  Ion Channel Positive Control (Reference Agonist)
  hGABAA α1β2γ2 30, 10, 3, 1, 0.3, and 0.1 μM GABA
  Electrophysiological Recording Solutions
    See Table 19.

Experimental Protocols & Data Analysis

Figure 11:
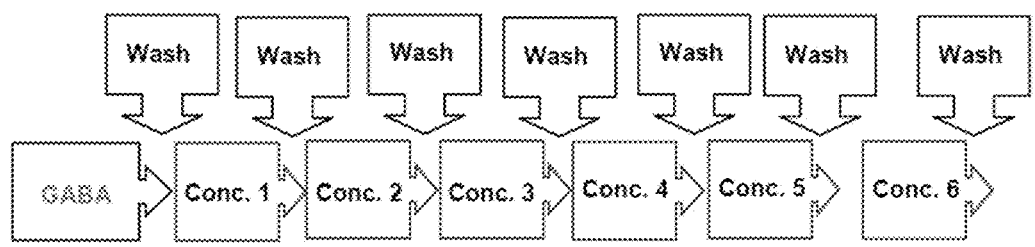
FIG. 11 is a schematic of hGABAA α2β3γ2 and hGABAA α1β3γ2 IonFlux HT Agonist Assay.
Figure 11:
Figure 11:
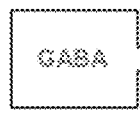
Figure 11:
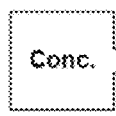

All recordings were obtained from a holding potential of −60 mV. The compound addition sequence that was used for all additions was the same for all assays. One addition of the EC100 concentration of GABA (30 μM) was added to establish baseline response. Each test concentration of compound was applied for 2 seconds followed by 60 seconds wash. The process was repeated with the next ascending concentration of test compound. The test compounds were applied over two (2) 'experimental patterns' in increasing concentrations (FIG. 11).

hGABAA α1β3γ2 IonFlux HT Agonist Assay Data Analysis

Peak inward currents in response to the GABA additions in the presence of a single concentration of compound were measured. All compound data have been normalized to the baseline peak current induced by addition of 30 μM GABA for 2 seconds:

Normalized Peak Current=$(I^{Compound+GABA}/I^{GABA})$

Where I (Compound) is the peak current induced by addition of test compound, I GABA is the baseline peak current induced by addition of 30 μM GABA. AM data were first exported to an Excel compatible data file and then analyzed using Graph Pad Prism software.

See Table 20.

Example 6. Efficacy of Isoguvacine in the Rat Spinal Nerve Ligation (SNL) Pain Rats Model of Neuropathic Pain

TABLE 22

| Test Article | |
|---|---|
| Name: | Isoguvacine |
| Storage Conditions: | 2-8° C., away from light |

TABLE 23

| Vehicle | |
|---|---|
| Name: | Saline |
| Supplier: | WuXi |
| Physical State: | Clear |
| Storage Conditions: | 2-8° C. |

TABLE 24

| Animal Use | |
|---|---|
| Species | SD Rat |
| Body Weight Range | ~140 g |
| Age (Study started) | 5-6 weeks old |
| Arrive Date | 2019.3.12 |
| Sex | Male |
| Source | SLAC, ShangHai, China |
| Address of Supplier | NO. 1696 Day Rd. Fengxian, Shanghai, P.R. China |
| Method of Identification | Tail markers |
| Number of Animals for Acclimation | 24 |
| Number of Animals for Dosing | 50 rats |
| Justification for number of Animals | 3 groups, animal number per dose group is 8 |

TABLE 25

Group and Dose Protocol

| Group | Administration | Dose | Vehicle | Route of Admin | Dosing volume | N |
|---|---|---|---|---|---|---|
| 1 | Vehicle | — | Saline | IP | 5 ml/kg | 8 |
| 2 | Isoguvacine | 5 mpk | Saline | IP | 5 ml/kg | 8 |

Chung surgery were conducted on anesthetized rats. Rats were habituated in the testing environment for 15 minutes before allodynia measurement (2-3 times). Pre-dose baseline were taken on day 9 post surgery. Rats that don't show allodynic response at this point were excluded. SNL rats with a paw withdrawal threshold >4 g. The animals were grouped according to 50% paw withdrawal threshold (g) and weight. The animals were dosed test articles and vehicle according to the dose protocol. On the testing day (Day 9), rats were dosed with testing articles with 16 min interval between groups. Rats were measured for allodynic response at 0.75, 1.5, 3 h time point post dosing. All values will be expressed as mean±S.E.M. The significance of the differences among groups will be evaluated by two-way ANOVA followed by Dunnett's test using graphpad Prism 6 software. A p value of less than 0.05 is considered statistically significant.

TABLE 26

Body Weight

| Animal ID | Group | Body weight (g) | Dose volume (mL) |
|---|---|---|---|
| 5 | Vehicle | 239.6 | 1.20 |
| 2 | Vehicle | 241.7 | 1.21 |
| 4 | Vehicle | 218.5 | 1.09 |
| 30 | Vehicle | 233.3 | 1.17 |
| 26 | Vehicle | 215.7 | 1.08 |
| 34 | Vehicle | 225.4 | 1.13 |
| 24 | Vehicle | 227.6 | 1.14 |
| 16 | Vehicle | 233.4 | 1.17 |
|  | Mean | 229.40 | 1.15 |
|  | SEM | 3.31 | 0.02 |
| 7 | Isoguvacine | 236.3 | 1.18 |
| 3 | Isoguvacine | 243.6 | 1.22 |
| 35 | Isoguvacine | 237.0 | 1.19 |
| 53 | Isoguvacine | 214.4 | 1.07 |
| 18 | Isoguvacine | 237.9 | 1.19 |
| 19 | Isoguvacine | 243.5 | 1.22 |
| 21 | Isoguvacine | 233.2 | 1.17 |
| 36 | Isoguvacine | 221.9 | 1.11 |
|  | Mean | 233.48 | 1.17 |
|  | SEM | 3.64 | 0.02 |

TABLE 27

50% g Threshold

| Animal ID | Group | 0 Hour | 0.75 Hour | 1.5 Hour | 3 Hour |
|---|---|---|---|---|---|
| 5 | Vehicle | 0.64 | 1.85 | 2.20 | 1.85 |
| 2 | Vehicle | 1.56 | 0.51 | 0.51 | 0.99 |
| 4 | Vehicle | 1.85 | 0.82 | 0.99 | 1.56 |
| 30 | Vehicle | 2.20 | 1.85 | 1.85 | 2.59 |
| 26 | Vehicle | 2.81 | 2.20 | 2.20 | 2.81 |
| 34 | Vehicle | 2.81 | 0.82 | 0.99 | 1.31 |
| 24 | Vehicle | 3.12 | 2.20 | 1.56 | 1.56 |

TABLE 27-continued

50% g Threshold

| Animal ID | Group | 0 Hour | 0.75 Hour | 1.5 Hour | 3 Hour |
|---|---|---|---|---|---|
| 16 | Vehicle | 3.72 | 0.99 | 0.67 | 1.56 |
|  | Mean | 2.34 | 1.40 | 1.37 |  |
|  | SEM | 0.35 | 0.24 | 0.24 |  |
| 7 | Isoguvacine | 0.99 | 1.31 | 1.85 | 2.81 |
| 3 | Isoguvacine | 1.10 | 2.37 | 2.37 | 6.74 |
| 35 | Isoguvacine | 1.85 | 1.31 | 0.82 | 7.91 |
| 53 | Isoguvacine | 2.23 | 2.81 | 1.85 | 3.33 |
| 18 | Isoguvacine | 2.81 | 1.56 | 2.81 | 5.15 |
| 19 | Isoguvacine | 3.00 | 0.99 | 1.85 | 4.34 |
| 21 | Isoguvacine | 3.31 | 1.56 | 1.56 | 5.77 |
| 36 | Isoguvacine | 3.31 | 2.37 | 2.64 | 3.31 |
|  | Mean | 2.32 | 1.78 | 1.97 |  |
|  | SEM | 0.33 | 0.23 | 0.23 |  |

TABLE 28

Von frey test (MEAN ± S.E.M.) (g)

| Group | 0 Hour | 0.75 Hour | 1.5 Hour | 3 Hour |
|---|---|---|---|---|
| Vehicle | 2.3 ± 0.35 | 1.4 ± 0.24 | 1.4 ± 0.24 | 1.8 ± 0.22 |
| Isoguvacine | 2.3 ± 0.33 | 1.8 ± 0.23 | 2.0 ± 0.23 | 4.9 ± 0.64 |

TABLE 29

Statistical analysis-Von frey test (vs. Vehicle) (Two way ANOVA followed by Dunn)

| Group | 0 Hour | 0.75 Hour | 1.5 Hour | 3 Hour |
|---|---|---|---|---|
| Isoguvacine | $P > 0.05$ | $P > 0.05$ | $P > 0.05$ | $P < 0.0001$ |

Chung surgery rats showed tactile allodynia 9 days after surgery. Isoguvacine showed significant analgesia effect at the 3 hour time point dose.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A method of reducing tactile dysfunction, anxiety, or social impairment in a human subject diagnosed with Autism Spectrum Disorder (ASD), Rett Syndrome (RTT), or Fragile X Syndrome, by administering to the subject a compound of Formula (I), or a pharmaceutically acceptable salt thereof:

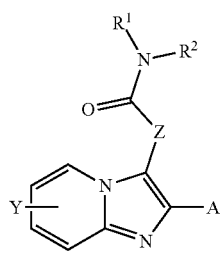

(I)

wherein
A is optionally substituted $C_{6-10}$ aryl or optionally substituted heteroaryl;
Y is hydrogen, deuterium, halogen, or optionally substituted $C_{1-4}$ alkyl;
Z is oxygen, $NR^3$, or $CR^3R^4$;
$R^1$ is optionally substituted alkylcarboxylic acid, optionally substituted alkylcarboxylic acid ester, optionally substituted alkylcarboxylic acid amide, optionally substituted heteroalkyl, optionally substituted $C_{1-6}$ alkylamino, or $C_{1-6}$ alkyl substituted with at least one $C_{3-7}$ heterocycle comprising 1-3 nitrogen atoms, 1-2 oxygen atoms, or combinations thereof;
$R^2$ is optionally substituted $C_{1-6}$ alkyl and
each of $R^3$ and $R^4$ is, independently, hydrogen, deuterium, or optionally substituted $C_{1-6}$ alkyl;
in an amount and for a duration sufficient to reduce the tactile dysfunction, anxiety, or social impairment.

2. The method of claim 1, wherein A is optionally substituted $C_{6-10}$ aryl.

3. The method of claim 1, wherein Y is halogen.

4. The method of claim 1, wherein Z is $CH_2$.

5. The method of claim 1, wherein $R^1$ is optionally substituted alkylcarboxylic acid.

6. The method of claim 1, wherein the compound has the structure of Formula (III), or a pharmaceutically acceptable salt thereof:

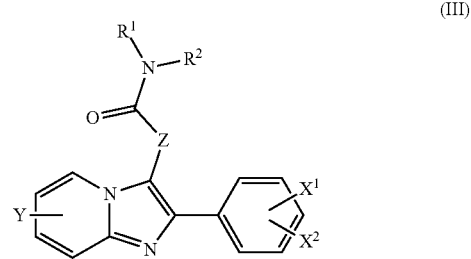

(III)

wherein
each of $X^1$ and $X^2$ is, independently, hydrogen, deuterium, halogen, $C_{1-4}$ alkoxy, $C_{1-6}$ alkyl, $CF_3$, $CH_3S$, $CH_3SO_2$, $NR^5R^6$, or $NO_2$; and
each of $R^5$ and $R^6$ is, independently, hydrogen, deuterium, optionally substituted $C_{1-6}$ alkyl, optionally substituted $C_{3-6}$ cycloalkyl, acyl, carbamate, sulfonamide, or urea.

7. The method of claim 6, wherein the compound has the structure of Formula (VII), or a pharmaceutically acceptable salt thereof:

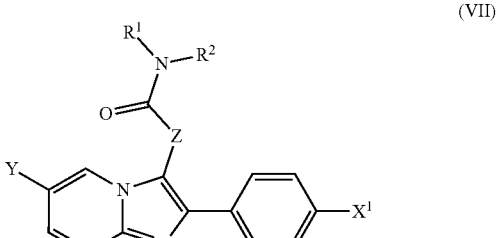

(VII)

wherein
$X^1$ is hydrogen, deuterium, halogen, $C_{1-4}$ alkoxy, $C_{1-6}$ alkyl, $CF_3$, $CH_3S$, $CH_3SO_2$, or $NO_2$;
Y is hydrogen, deuterium, halogen, or $C_{1-4}$ alkyl;
Z is oxygen, NH, or $CH_2$; and
$R^1$ is optionally substituted alkylcarboxylic acid.

8. The method of claim 7, wherein $X^1$ is halogen.

9. The method of claim 7, wherein Y is halogen.

10. The method of claim 7, wherein Z is CH$_2$.
11. The method of claim 7, wherein X$^1$ is halogen, Y is halogen, and Z is CH$_2$.
12. The method of claim 1, wherein the compound has the structure:
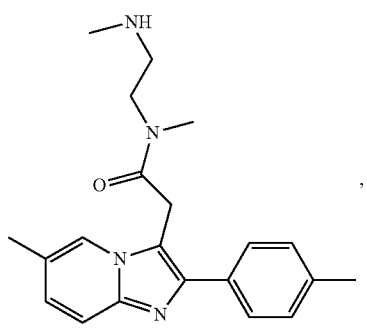
1
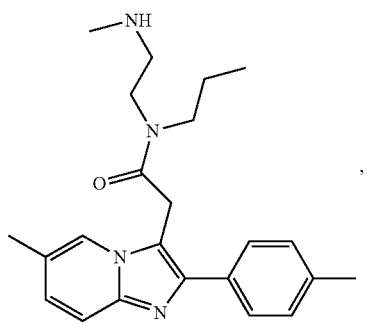
2
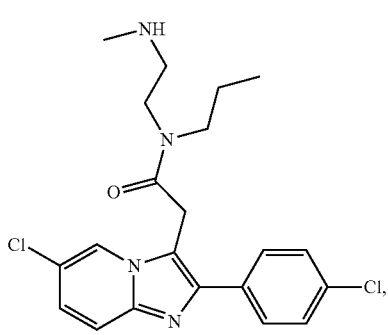
3
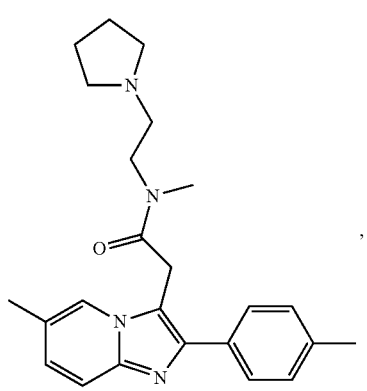
7
-continued
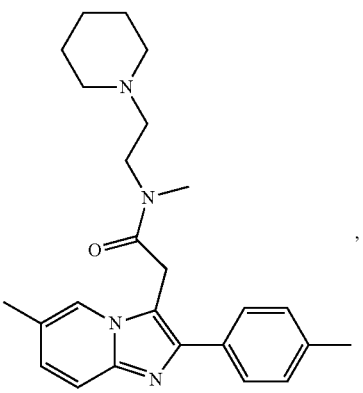
8
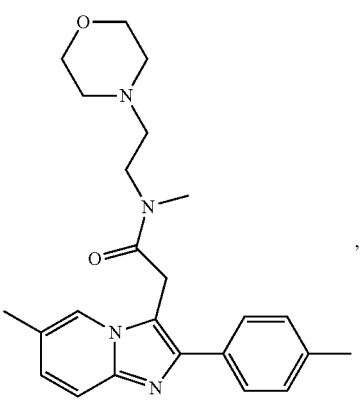
9
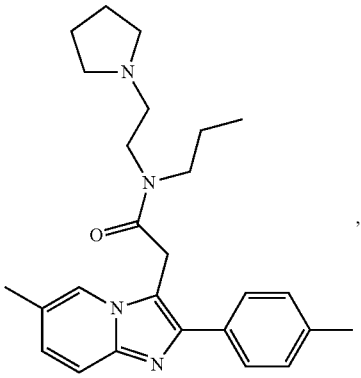
10
11

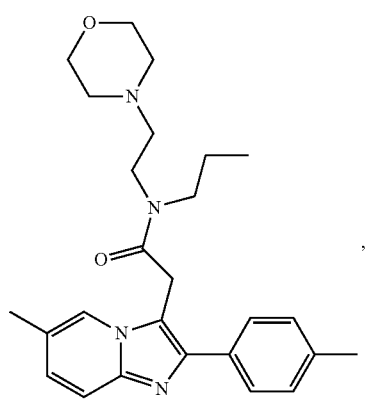
12
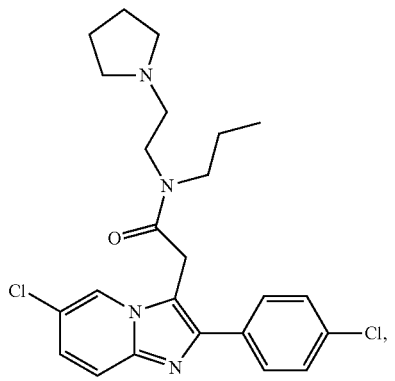
19
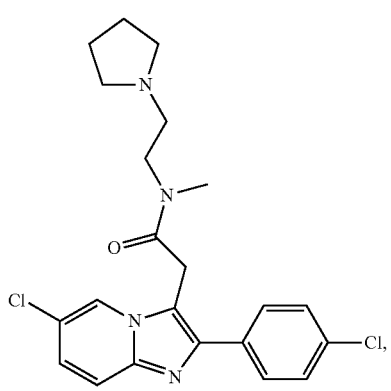
16
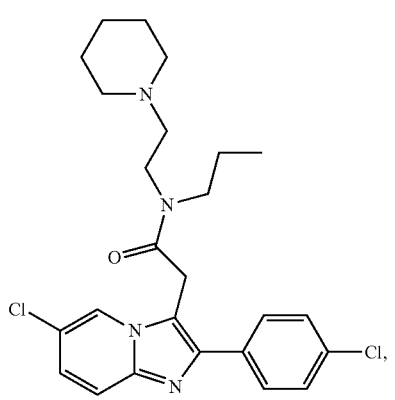
20
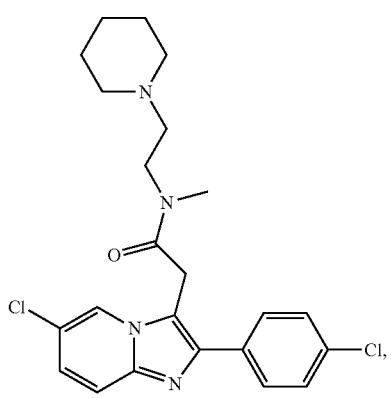
17
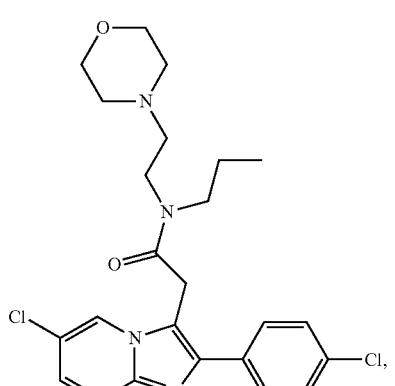
21
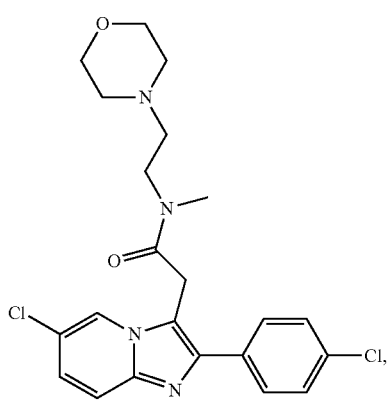
18
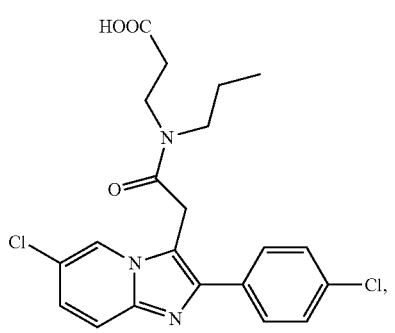
36

-continued

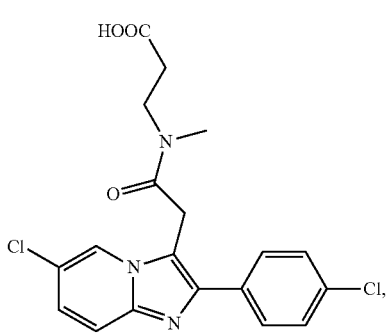

or a pharmaceutically acceptable salt thereof.

13. The method of claim 1, having the structure:

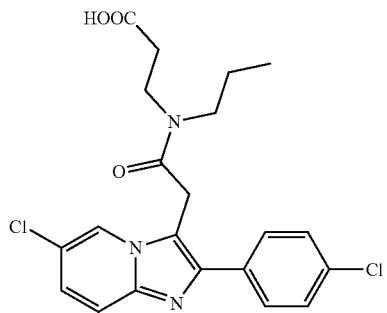

or a pharmaceutically acceptable salt thereof.

14. The method of claim 1, for reducing tactile dysfunction in the subject.

15. The method of claim 1, for reducing anxiety in the subject.

16. The method of claim 1, for reducing social impairment in the subject.

17. The method of claim 1, wherein the subject is a child.

18. A method of treating touch over-reactivity, pain, or mechanical allodynia in a human subject in need thereof, comprising administering to the subject a compound of Formula (I), or a pharmaceutically acceptable salt thereof:

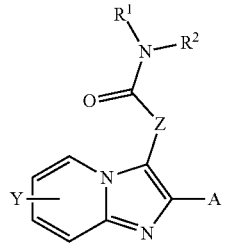

wherein
  A is optionally substituted $C_{6-10}$ aryl or optionally substituted heteroaryl;
  Y is hydrogen, deuterium, halogen, or optionally substituted $C_{1-4}$ alkyl;
  Z is oxygen, $NR^3$, or $CR^3R^4$;
  $R^1$ is optionally substituted alkylcarboxylic acid, optionally substituted alkylcarboxylic acid ester, optionally substituted alkylcarboxylic acid amide, optionally substituted heteroalkyl, optionally substituted $C_{1-6}$ alkylamino, or $C_{1-6}$ alkyl substituted with at least one $C_{3-7}$ heterocycle comprising 1-3 nitrogen atoms, 1-2 oxygen atoms, or combinations thereof;
  $R^2$ is optionally substituted $C_{1-6}$ alkyl and
  each of $R^3$ and $R^4$ is, independently, hydrogen, deuterium, or optionally substituted $C_{1-6}$ alkyl;
  in an amount and for a duration sufficient to reduce the touch over-reactivity, pain, or mechanical allodynia.

19. The method of claim 18, wherein the touch over-reactivity or pain is associated with Sensory Processing Disorder (SPD) or fibromyalgia.

20. The method of claim 18, wherein the mechanical allodynia is associated with nerve injury, shingles, diabetic neuropathy, chemotherapy-induced neuropathy, or a neuropathic pain state.

* * * * *